US010975409B2

(12) United States Patent
Khan et al.

(10) Patent No.: US 10,975,409 B2
(45) Date of Patent: Apr. 13, 2021

(54) METHOD FOR STABILIZING PROTEINS

(71) Applicant: LONZA LTD, Visp (CH)

(72) Inventors: Mohsan Waseem Khan, Watford (GB); Alison Porter, Charvil (GB)

(73) Assignee: LONZA LTD, Visp (CH)

( * ) Notice: Subject to any disclaimer, the term of this patent is extended or adjusted under 35 U.S.C. 154(b) by 680 days.

(21) Appl. No.: 15/619,876

(22) Filed: Jun. 12, 2017

(65) Prior Publication Data
US 2017/0356022 A1 Dec. 14, 2017

Related U.S. Application Data

(60) Provisional application No. 62/348,595, filed on Jun. 10, 2016.

(51) Int. Cl.
| C12P 21/00 | (2006.01) |
| C12P 21/02 | (2006.01) |
| C07K 1/14 | (2006.01) |
| C12M 1/06 | (2006.01) |
| C12M 1/00 | (2006.01) |
| C07K 16/00 | (2006.01) |
| C12M 1/34 | (2006.01) |
| A61K 38/00 | (2006.01) |

(52) U.S. Cl.
CPC .............. *C12P 21/00* (2013.01); *C07K 1/14* (2013.01); *C07K 16/00* (2013.01); *C12M 27/02* (2013.01); *C12M 29/00* (2013.01); *C12M 41/12* (2013.01); *C12M 41/28* (2013.01); *C12M 41/34* (2013.01); *C12M 47/10* (2013.01); *C12M 47/20* (2013.01); *C12P 21/02* (2013.01); *A61K 38/00* (2013.01); *C07K 2317/14* (2013.01); *C07K 2317/56* (2013.01)

(58) Field of Classification Search
CPC ............ C12P 21/00; C07K 1/14; C07K 16/00
See application file for complete search history.

(56) References Cited

U.S. PATENT DOCUMENTS

| 5,633,162 | A | 5/1997 | Keen et al. |
| 5,656,491 | A | 8/1997 | Cassani et al. |
| 7,629,167 | B2 | 12/2009 | Hodge et al. |
| 8,298,054 | B2 | 10/2012 | Hodge et al. |
| 2009/0305626 | A1 | 12/2009 | Hope |
| 2011/0280797 | A1 | 11/2011 | Mohtadi et al. |
| 2011/0312087 | A1 | 12/2011 | Khan |
| 2012/0077429 | A1 | 3/2012 | Wernimont et al. |
| 2013/0280797 | A1 | 10/2013 | Rao et al. |

FOREIGN PATENT DOCUMENTS

| EP | 1489188 A1 | 12/2004 |
| WO | 2013050034 A1 | 4/2013 |
| WO | 2017212071 A1 | 12/2017 |

OTHER PUBLICATIONS

Tang et al. "Recent development of temperature-responsive surfaces and their application for cell sheet engineering" (2014), Regenerative Biomaterials: 91-102. doi 10.1093/lrb/bu011. (Year: 2014).*
Banhegyi et al. "Stress on Redox" FEBS Letters (2007) vol. 581, pp. 3634-3640.
Chakravarthi et al. "The role of glutathione in disulphide bond formation and endoplasmic-reticulum-generated oxidative stress" EMBO Reports (2006) vol. 7, No. 3, pp. 271-275.
Flohe et al. "The fairytale of the GSSG/GSH redox potential" Biochimica et Biophysica Acta (2013) vol. 1830, pp. 3139-3142.
Ghezzi et al. "Oxidoreduction of protein thiols in redox regulation" Biochemical Society Transactions (2005) vol. 33, part 6, pp. 1378-1381.
Hanschmann et al. "Thioredoxins, Glutaredoxins, and Peroxiredoxins-Molecular Mechanisms and Health Significance: from Cofactors to Antioxidants to Redox Signaling" Antioxidants & Redox Signaling (2013) vol. 19, No. 13, pp. 1539-1605.
Hastings et al. "Disulfide Reduction in the Endocytic Pathway: Immunocological Functions of Gamma-Interferon-Inducible Lysosomal Thiol Reductase" Antioxidants & Redox Signaling (2011) vol. 15, No. 3, pp. 657-668.
Holmgren et al. "Thiol redox control via thioredoxin and glutaredoxin systems" Biochemical Society Treansactions (2005) vol. 33, part 6, pp. 1375-1377.
International Search Report and Written Opinion for International Application No. PCT/EP2017/064313 dated Oct. 20, 2017.
Ivarsson et al. "Redox Control of Exocytosis" Diabetes (2005) vol. 54, pp. 2132-2142.
Kojer et al. "Balancing oxidative protein folding: The influences of reducing pathways on disulfide bond formation" Biochimica et Biophysica Acta (2014) vol. 1844, pp. 1383-1390.
Leader et al. "Protein therapeutics: a summary and pharmacological classification" Nature Reviews Drug Discovery (2008) vol. 7, pp. 21-39.
May et al. "Reduction of Dehydroascorbate to Ascorbate by the Selenoenzyme Thioredoxin Reductase" The Journal of Biological Chemistry (1997) vol. 272, No. 36, pp. 22607-22610.
Molteni et al. "Glutathione Limits Ero1-dependent Oxidation in the Endoplasmic Reticulum" The Journal of Biological Chemistry (2004) vol. 279, No. 31, pp. 32667-32673.
Nordberg et al. "Reactive Oxygen Species, Antioxidants, and the Mammalian Thioredoxin System" Free Radical Biology & Medicine (2001) vol. 31, No. 11, pp. 1287-1312.
Rausch et al. "Diverse cellular and organismal functions of the lysosomal thiol reductase GILT" Molecular Immunology (2015) vol. 68, pp. 124-128.
Schwarzlander et al. "Dissecting Redox Biology Using Fluorescent Protein Sensors" Antioxidants & Redox Signaling (2016) vol. 24, No. 13, pp. 680-712.
Sen et al. "Redox Signaling and th (Continued)

*Primary Examiner* — Teresa E Knight
(74) *Attorney, Agent, or Firm* — Medler, Ferro, Woodhouse & Mills PLLC

(57) ABSTRACT

The present disclosure features methods and compositions for increasing the amount of products of cellular metabolism, e.g., proteins, by lowering the temperature of cells expressing the product at one or more steps while culturing the cells, expressing the product, and/or recovering the product.

48 Claims, 11 Drawing Sheets

(56) References Cited

OTHER PUBLICATIONS

Emerging Therapeutic Potential of Thiol Antioxidants" Biochemical Pharmacology (1998) vol. 55, pp. 1747-1758.

Winkler et al. "The Redox Couple Between Glutathione and Ascorbic Acid: A Chemical and Physiological Perspective" Free Radical Biology & Medicine (1994) vol. 17, No. 4, pp. 333-349.

Meneses-Acosta et al., "Control of redox potential in hybridoma cultures: effects on MAb production, metabolism, and apoptosis," J Ind Microbiol Biotechnol 39:1189-1198 (2012).

Mensses-Asosta et al., "Effect of controled redox potential and dissolved oxygen on the in vitro refeiding of *E. coli* alkaline phosphatase and chicken lysozyme," Enzyme and Microbial Techology 52:312-318 (2013).

* cited by examiner

FIGURE 4
NON-REDUCED GEL SDS PAGE
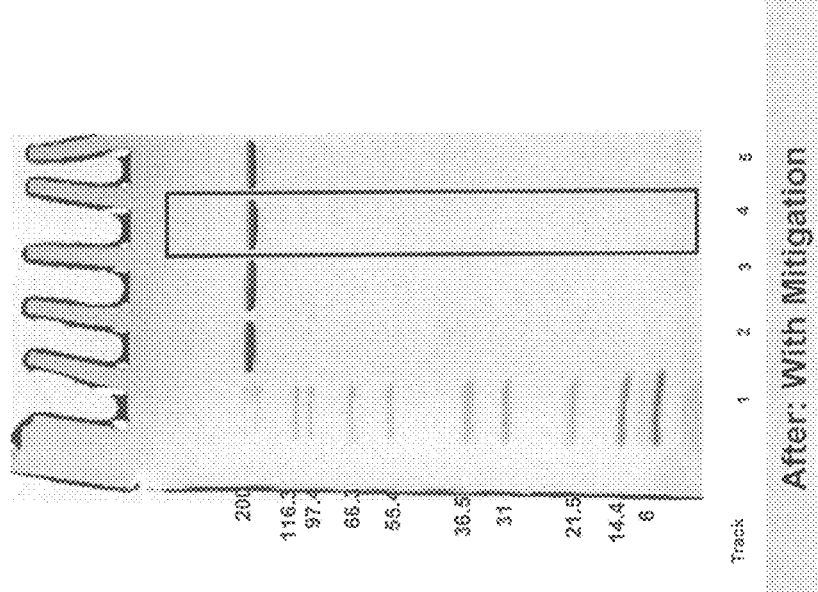
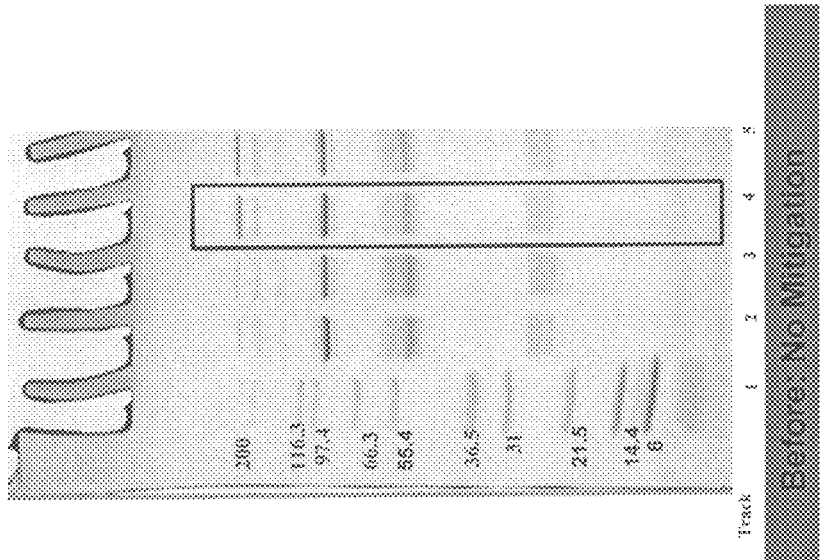

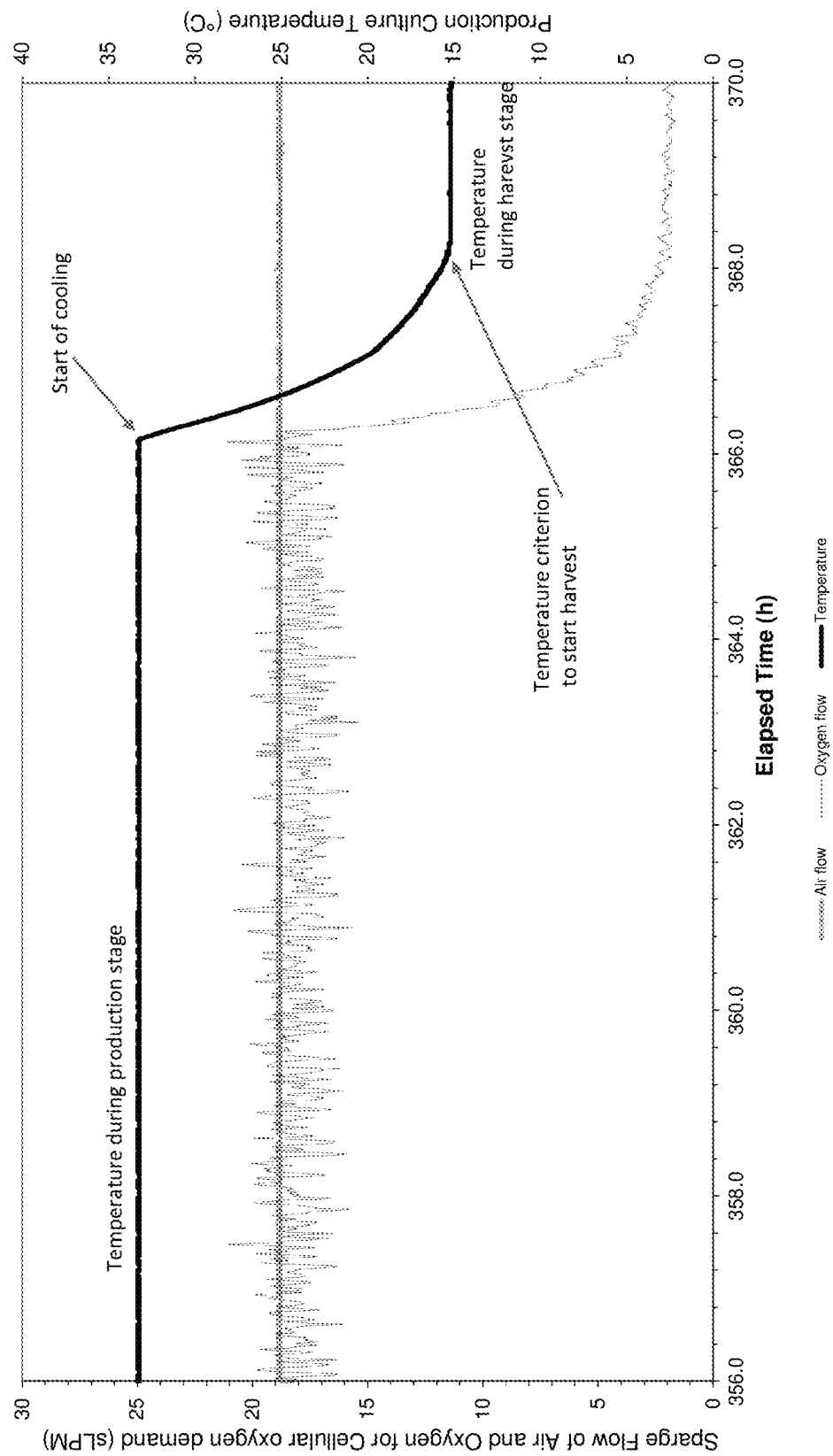

An example of Control Profiles When the Sparged Air and Oxygen are Fixed in the Production Culture during harvesting

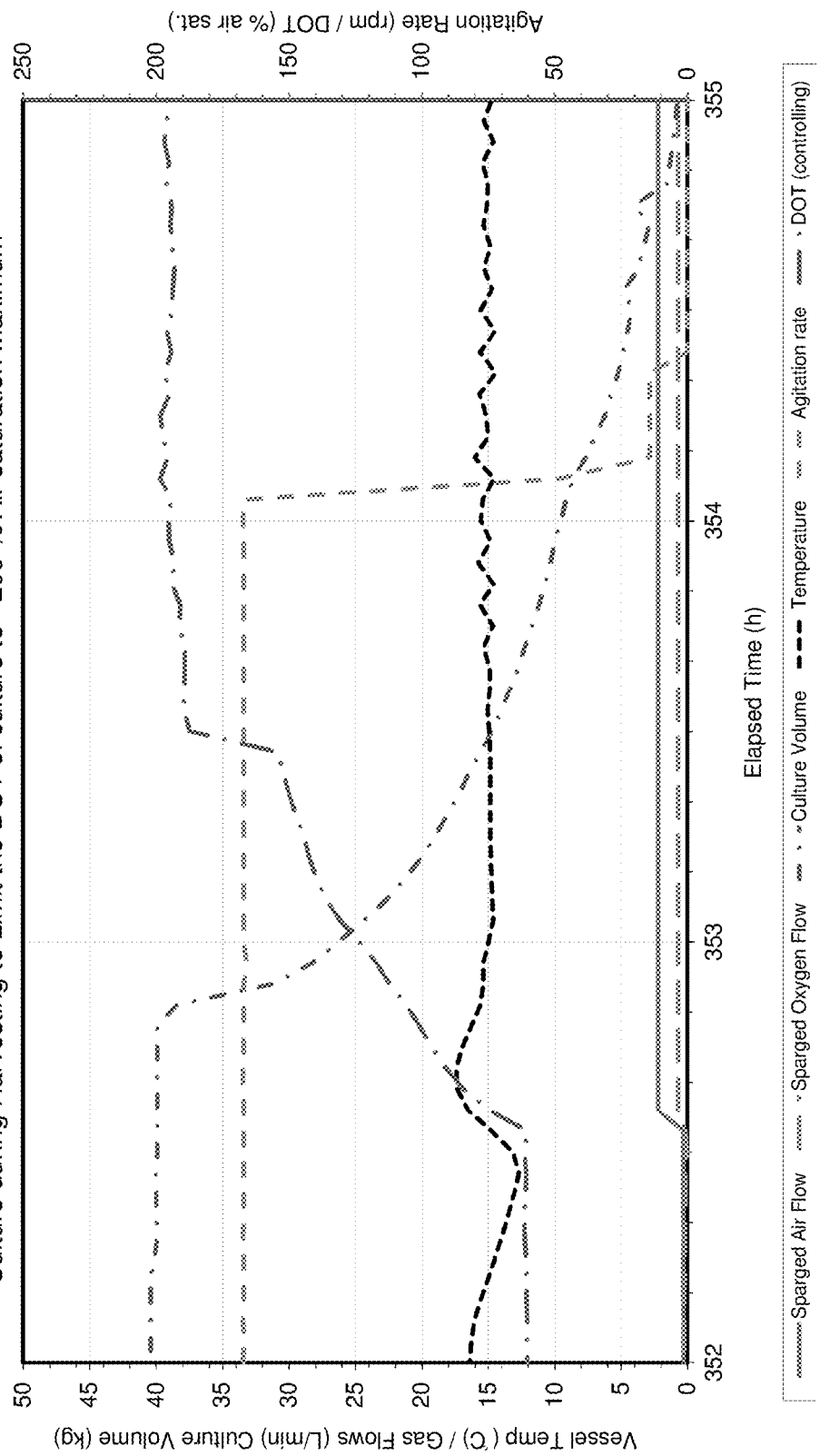

METHOD FOR STABILIZING PROTEINS

RELATED APPLICATIONS

This application claims priority to U.S. Ser. No. 62/348,595, filed Jun. 10, 2016, the entire contents of which is incorporated herein by reference in its entirety.

FIELD OF THE INVENTION

The disclosure relates to methods and compositions for inhibiting dissociation of cellular products, e.g., polypeptides, expressed in cultured cells.

BACKGROUND

Cellular products such as recombinant therapeutic proteins are commonly expressed in cell expression systems, e.g., mammalian cell expression systems. Hundreds of market approved biopharmaceuticals are expressed in mammalian cell lines. However, the high cost associated with their production contributes to increasing global health costs. Product dissociation events can result in lower than expected stability or activity of proteins or polypeptides expressed from cells grown in cell culture. These events are detected through non-reducing SDS electrophoresis assays that reveals presence of dissociation of the polypeptide product with low abundance of intact product. Other quality control tests do not reveal the polypeptide dissociation events.

Moreover, product dissociation events can impair the function and stability of the expressed proteins. Accordingly, there is a need to develop and produce methods for inhibiting the dissociation of polypeptides expressed in cultured cells.

SUMMARY

The present disclosure is based, in part, on the discovery that a number of measures identified below can inhibit dissociation of expressed products, e.g., polypeptides.

In one aspect, the invention features a method of producing a stabilized product, e.g., a stabilized protein, expressed in a recombinant host cell, comprising:

maintaining a redox potential difference in the range of −50 mV to −300 mV from a non-stabilized product to a stabilized product during separation of cells from production culture and collection of a supernatant, wherein separation of cells from a production culture and collection of supernatant is conducted without sparging or sufficiently little sparging that the sparging does not substantially alter the redox potential in the production culture and the supernatant, thereby producing a stabilized product, e.g., an isolated, stabilized protein.

In another aspect, the invention features a method of producing a stabilized product, e.g., a stabilized protein, expressed in a recombinant host cell, comprising:

providing, e.g., establishing, a redox potential difference in the range of −50 mV to −300 mV from a non-stabilized product to a stabilized product in a post-exponential growth culture phase of a production culture, and maintaining a redox potential difference in the range of −50 mV to −300 mV from a non-stabilized product to a stabilized product during separation of cells from production culture and collection of a supernatant, wherein separation of cells from a production culture and collection of supernatant is conducted without sparging or sufficiently little sparging that the sparging does not substantially alter the redox potential in the production culture and the supernatant, thereby producing a stabilized product, e.g., an isolated, stabilized protein.

In another aspect, the invention features a method of producing a stabilized product, e.g., a stabilized protein, expressed in a recombinant host cell, comprising:

providing, e.g., establishing a redox potential difference in the range of −50 mV to −300 mV from a non-stabilized product to a stabilized product in a post-exponential growth culture phase of the production culture, wherein dissolved oxygen tension (DOT) from start of the production phase to the end of the production phase is in a range of greater than 40% to 70% air saturation;

cooling the production culture at the end of production phase to a $T_{harvest}$ temperature, which is a temperature that is below the temperature at which the cell line was or is normally cultured;

increasing the DOT to a range of greater than 40% to less than 500% air saturation by sparging air or $O_2$ gas into the production culture until separation of cells from production culture and collection of supernatant; and maintaining a redox potential difference in the range of −50 mV to −300 mV from a non-stabilized product to a stabilized product during separation of cells from production culture and collection of a supernatant, wherein separation of cells from a production culture and collection of supernatant is conducted without sparging or sufficiently little sparging that the sparging does not substantially alter the redox potential in the production culture and the supernatant, thereby producing a stabilized product, e.g., an isolated, stabilized protein.

In another aspect, the invention features a method of producing a stabilized product, e.g., a stabilized protein, expressed in a recombinant host cell, comprising:

(i) providing, e.g., establishing, a production culture, e.g., a post-exponential growth culture, comprising a recombinant host cell expressing the product, e.g., a protein, at a redox potential difference in the range of −50 mV to −300 mV from a non-stabilized product to a stabilized product;

(ii) maintaining a redox potential difference in the range of −50 mV to −300 mV from a non-stabilized product to a stabilized product in a post-exponential growth culture phase; and (iii) maintaining a redox potential difference in the range of −50 mV to −300 mV from a non-stabilized product to a stabilized product during separation of cells from production culture and collection of a supernatant, wherein separation of cells from a production culture and collection of supernatant is conducted without sparging or sufficiently little sparging that the sparging does not substantially alter the redox potential in the production culture and the supernatant, wherein the method comprises:

a. cooling the production culture after exponential growth phase has occurred, to a temperature of 30° C. to 33° C., which is a temperature that is below the temperature at which the cell line was or is normally cultured;

b. oxygenating the production culture, to a dissolved oxygen tension (DOT) greater than 40% air saturation to less than or equal to 70% air saturation from start of the production phase to the end of the production phase;

c. providing, e.g., adding, transition metals in or to the production culture, wherein the transition metals ions are selected from $Zn^{2+}$, $Mn^{4+}$, $Cu^{2+}$, $Fe^{3+}$, $Co^{2+}$, $Cr^{3+}$, and/or $Ni^{2+}$;

d. providing, e.g., adding, dehydroascorbic acid or ascorbic acid, or a dehydroascorbic acid or ascorbic acid modifying component, to the production culture;

e. providing, e.g., adding glutathione, e.g., oxidized and/or reduced glutathione, or a glutathione modifying component, to the production culture; or f. cooling the production culture for separation of cells from production culture and collection of supernatant to a temperature $T_{harvest}$ of 12° C.-18° C., which is a temperature that is below $T_{production}$, thereby producing a stabilized product, e.g., an isolated, stabilized protein or a preparation of a stabilized product, e.g., a stabilized protein.

In another aspect, the invention features to a stabilized protein or preparation of stable protein produced by a method described herein.

In another aspect, the invention features a pharmaceutical composition comprising a stabilized protein or preparation of stabilized protein produced by a method described herein.

In another aspect, the invention features a bioreactor capable of producing a stabilized product, e.g., a stabilized protein, expressed in a recombinant host cell, wherein the bioreactor is capable of maintaining a redox potential difference in the range of −50 mV to −300 mV from a non-stabilized product to a stabilized product during separation of cells from production culture and collection of the supernatant, wherein separation of cells from a production culture and collection of the supernatant is conducted without sparging or sufficiently little sparging that the sparging does not substantially alter the redox potential in the production culture and the supernatant.

In another aspect, the invention features a bioreactor capable of producing a stabilized product, e.g., a stabilized protein, expressed in a recombinant host cell, wherein the bioreactor is capable of:

providing, e.g., establishing, a redox potential difference in the range of −50 mV to −300 mV from a non-stabilized product to a stabilized product in a post-exponential growth phase of a production culture, and maintaining a redox potential difference in the range of −50 mV to −300 mV from a non-stabilized product to a stabilized product during separation of cells from production culture and collection of the supernatant, wherein separation of cells from a production culture and collection of supernatant is conducted without sparging or sufficiently little sparging that the sparging does not substantially alter the redox potential in the production culture and the supernatant.

In another aspect, the invention features a bioreactor capable of producing a stabilized product, e.g., a stabilized protein, expressed in a recombinant host cell, wherein the bioreactor is capable of:

providing, e.g., establishing a redox potential difference in the range of −50 mV to −300 mV from a non-stabilized product to a stabilized product in a post-exponential growth phase of the production culture, wherein dissolved oxygen tension (DOT) from start of the production phase to the end of the production phase is in a range of greater than 40% air saturation to 70% air saturation;

cooling the production culture at the end of production phase to a $T_{harvest}$ temperature, which is a temperature that is below the temperature at which the cell line was or is normally cultured;

increasing the DOT to a range of greater than 40% air saturation to less than 500% air saturation by sparging air or $O_2$ gas into the production culture until removal of the production culture from the bioreactor; and maintaining a redox potential difference in the range of −50 mV to −300 mV from a non-stabilized product to a stabilized product during separation of cells from production culture and collection of a supernatant, wherein separation of cells from a production culture and collection of supernatant is conducted without sparging or sufficiently little sparging that the sparging does not substantially alter the redox potential in the production culture and the supernatant.

In another aspect, the invention features a bioreactor capable of producing a stabilized product, e.g., a stabilized protein, expressed in a recombinant host cell, wherein the bioreactor is capable of:

(i) providing, e.g., establishing, a production culture, e.g., a post-exponential growth culture, comprising a recombinant host cell expressing the product, e.g., a protein, at a redox potential difference in the range of −50 mV to −300 mV from a non-stabilized product to a stabilized product;

(ii) maintaining a redox potential difference in the range of −50 mV to −300 mV from a non-stabilized product to a stabilized product in a post-exponential growth phase; and (iii) maintaining a redox potential difference in the range of −50 mV to −300 mV from a non-stabilized product to a stabilized product during separation of cells from production culture and collection of the supernatant, wherein separation of cells from a production culture and collection of supernatant is conducted without sparging or sufficiently little sparging that the sparging does not substantially alter the redox potential in the production culture and the supernatant, wherein the bioreactor is further capable of:

a. cooling the production culture after exponential growth phase has occurred, to a temperature of 30° C. to 33° C., which is a temperature that is below the temperature at which the cell line was or is normally cultured;

b. oxygenating the production culture, to an dissolved oxygen tension (DOT) greater than 40% to less than or equal to 70% air saturation from start of the production phase to the end of the production phase;

c. providing, e.g., adding, transition metal ions in or to the production culture, wherein the transition metal ions are selected from $Zn^{2+}$, $Mn^{4+}$, $Cu^{2+}$, $Fe^{3+}$, $Co^{2+}$, $Cr^{3+}$, and/or $Ni^{2+}$;

d. providing, e.g., adding, dehydroascorbic acid or ascorbic acid, or a dehydroascorbic acid or ascorbic acid modifying component, to the production culture;

e. providing, e.g., adding glutathione, e.g., oxidized and/or reduced glutathione, or a glutathione modifying component, to the production culture;

f. cooling the production culture for separation of cells from production culture and collection of supernatant to a temperature $T_{harvest}$ of 12° C.-18° C., which is a temperature that is below $T_{production}$.

In an embodiment, methods disclosed herein include and bioreactors disclosed herein are capable of maintaining any of a number of conditions, e.g., the presence of feeds/supplements or a physicochemical condition, to promote a more favorable redox potential in the production culture, e.g. during a growth phase, e.g., during an exponential growth phase. Typically, the condition is maintained, e.g., at least partially, in later stages, e.g., at harvest or post-harvest stage. By way of example, a condition is maintained, at a level which optimizes production of stabilized product, e.g., stabilized protein, when the cells enter into the harvest stage and the post-harvest stages and optionally, maintained until the product is isolated from the background process and cellular impurities.

In an embodiment, a feed or supplement comprises, $Zn^{2+}$, $Mn^{2+}$ and $Cu^{2+}$ salts, e.g., at a level that provides a residual concentration of $Zn^{2+}$ ions ranging from 200 to 400 µM and a residual concentration of $Mn^{2+}$ and $Cu^{2+}$ ions ranging from 10 to 100 µM in the production culture respectively.

In an embodiment, the dissolved oxygen tension (DOT) of the production culture is maintained between at least 40% and 70% of air saturation.

In an embodiment, the production culture is initially maintained at a first temperature, e.g., 36° C. to 37° C., and is shifted, e.g., at a predetermined point, e.g., once production begins to exit growth phase, at a second, typically lower, temperature, e.g., 30° C. to 33° C. In an embodiment the temperature of the production culture is controlled initially at 36° C. to 37° C. but then temperature is controlled at 30° C. to 33° C. once production culture begins to exit the growth phase, typically day 5 to day 7 of 15 day production duration.

In an embodiment, the method comprises or the bioreactor is capable of maintaining the redox potential of the production culture towards a relatively more oxidative potential, e.g., an oxidative potential that increases the production of stabilized product, e.g., by at least, 5, 10, 15, 20, 25, 30, 35, 40, 45, 50, 55, 60, 65, 70, 75, 80, 85, 90, 95, or 100%, through using one or more conditions described above. Alternative means may also be used to modify the redox potential toward a more oxidative potential and these include other redox potential affecting medium components or alteration of cellular metabolism to elevate pro-oxidant metabolites, such as dehydroascorbic acid/ascorbic acid, glutathione/glutathione-SH, and cysteine/cystine in combination with temperature and DOT.

In an embodiment, the method comprises or the bioreactor is capable of using redox potential-indicating labels, e.g., dyes or molecular probes, to sense the change in the redox potential of cells within production culture to affect appropriate process change to prevent the subsequent product expressed by the cells from being dissociated. In an embodiment, the method comprises or the bioreactor is capable of using redox potential in-line monitoring probes, e.g., Mettler Toledo probe as described herein.

In an embodiment, the method comprises using analytical methods to probe enzymatic activity (e.g., glutathione reductase, thioredoxin, thioredoxin reductase) and/or the abundance of cofactors and associated metabolic products (e.g., cofactors and associated metabolic products associated with the pentose phosphate pathway, e.g., glucose-6-phosphate, NADPH, NADP+, 6-phosphonoglucolactone, 6-phosphogluconate, or ribulose-5-phosphate) involved in product dissociation reactions and expressed by cell lines. In one embodiment, probing enzymatic activity and the abundance of cofactors and associated metabolic products is used to select cell lines and clones which have reduced or desirable level of cellular factors that do not promote product dissociation during further processing.

In an embodiment, the method comprises or the bioreactor is capable of cooling cultured cells to 15±3° C. before separating them from the product-containing supernatant using depth filtration or centrifugation and depth filtration steps.

In an embodiment, once the production culture have reached the target temperature to initiate the harvest step, the method comprises or the bioreactor is capable of ensuring all elements that are likely to antagonize the oxygenation of the production culture are minimized, e.g., through process controls. In embodiments, the method comprises or the bioreactor is capable of: inhibiting sparged nitrogen gas flow if active, inhibiting on demand alkali control if active, inhibiting on demand CO2 gas flow control if active, or inhibiting feed application if active.

In an embodiment, once the production culture has reached the target temperature to initiate the harvest step, the method comprises or the bioreactor is capable of ensuring all elements that are likely to promote the oxygenation of the production culture are maximized and/or activated, e.g., through process controls. In embodiments, the method comprises or the bioreactor is capable of one or more of: activating sparged air gas flow if not active; activating sparged oxygen gas flow if not active; activating head space pressure if not active; activating head space air and/or oxygen flow if not active; ensuring the cell culture remains well mixed and aerated whilst it is drained out during the harvesting operation; ensuring the bioreactor harvest lines are designed with respect to internal bore size and wall strength to resist collapsing and impeding the desired flow rate during harvest operation; optimizing depth filter area to avoid blockage and fouling of the filters during the filter clarification step and thereby increasing the residence time of the cell culture within the filter housings; and ensuring the cell-free supernatant is collected in well aerated and mixed collection vessel (steel or single-use). In embodiments, a harvest vessel for use in a method is designed to ensure it promote good surface oxygenation through one or both of: impinging collected filtrate onto the vessel wall surface by designing internal nozzle directed towards the vessel wall that force the filtrate to cascade down vessel walls; and ability to fill the collection vessel before filtrate collection with a gaseous environment composed of air or any given blend of air and oxygen to promote oxygenation of the collected filtrate to greater than >40% air saturation and ≤500% air saturation.

In embodiments, it is proposed that the flow path between the bioreactor and cell clarification step and between the cell clarification step and supernatant collection vessel, e.g., harvest vessel, are monitored with Redox, DOT and pH sensors. Additionally, parameters in the bioreactor may be adjusted to alter the redox, DOT and pH within the two flow paths or supernatant collection vessel, e.g., harvest vessel.

In one aspect, the disclosure features a method for producing a product, e.g., a polypeptide, e.g., a recombinant polypeptide, by a cell, comprising providing a cell line comprising the cell and comprising a polynucleotide sequence encoding the polypeptide. The production culture is cultured under conditions allowing for expression of the product, e.g., polypeptide, the production culture is cooled to 30° C. to 33° C., which is a temperature that is below the temperature at which the cell line was, or is normally cultured, to thereby make the product, e.g., polypeptide. Further cooling of the production culture to a $T_{harvest}$ temperature, e.g., 15° C., occurs at the end of production phase.

In embodiments, the product is a polypeptide that comprises more than one cysteine residue, e.g., a first, second, third and fourth or more cysteine residue. In embodiments, the polypeptide in native form comprises a sulfhydryl bond between the first and a second cysteine residue. In embodiments, the polypeptide comprises a sulfhydryl bond between the third and a fourth cysteine residue. In embodiments, $T_{harvest}$ is sufficiently low to decrease consumption of dissolved oxygen in culture such that sufficient dissolved oxygen is available in the supernatant to prevent the activation of cellular factors (both enzymatic and metabolites) and inhibit dissociation of the disulphide bonds. In embodiments, $T_{harvest}$ is sufficiently low to prevent dissociation of the disulphide bond, by at least 10, 20, 30, 40, 50, 60, 70, 80, or 90%, as compared with a reference, e.g., the level of dissociation obtained from an otherwise similar process but that was not cooled to $T_{harvest}$.

In embodiments, the method comprises separating the expressed polypeptide, from the cultured cells at $T_{harvest}$.

In embodiments, the method comprises purifying the expressed polypeptide when the cell line expressing the polypeptide is cooled to $T_{harvest}$.

In embodiments, the cell line is cultured at a first temperature, $T_{culture}$ and subsequently cooled to a temperature $T_{production}$ (e.g., 30° C. to 33° C.) after exponential growth phase, and further cooled at the end of the production phase to a harvest temperature $T_{harvest}$ (e.g., 12° C.-18° C.). In embodiments, $T_{culture}$ is greater than $T_{production}$ In embodiments, $T_{production}$ is greater than $T_{harvest}$.

In embodiments, cells typically cultured at $T_{culture}$ of 37° C. are placed at $T_{production}$ of less than 35° C., 34° C., 33° C., 32° C., 31° C., or 30° C. In embodiments, culture is further cooled to $T_{harvest}$ of 29° C., 28° C., 27° C., 26° C., 25° C., 24° C., 23° C., 22° C., 21° C., 20° C., 19° C., 18° C., 17° C., 16° C., 15° C., 14° C., 13° C., 12° C., 11° C., 10° C., 9° C., 8° C., 7° C., 5° C., or 4° C., or less than 15° C., less than ambient temperature, and/or less than room temperature. In embodiments, $T_{harvest}$ is less than 6-24° C. In an embodiment, $T_{harvest}$ is 15+/−3° C.

For example, in embodiments, $T_{production}$ is at least 1° C., 3° C., or 6° C. below $T_{culture}$.

For example, in embodiments, $T_{harvest}$ is at least 2° C., 5° C., or 8° C. below $T_{production}$.

In embodiments, the cultured cells are separated from supernatant at $T_{harvest}$.

In embodiments, a separation step is performed that separates the polypeptide from another component of the supernatant at $T_{harvest}$.

In embodiments, a polypeptide, e.g., as a component of supernatant, is applied to a filter at $T_{harvest}$.

In embodiments, the contents of the bioreactor are cooled to $T_{harvest}$.

In embodiments, the cell culture is cooled by contact with a member, e.g., a cooling jacket, comprising a fluid, e.g., water, at a temperature suitable for bring the cell culture to $T_{harvest}$.

In embodiments, the method further comprising providing a nutrient or oxygen during $T_{culture}$, $T_{production}$ and/or $T_{harvest}$.

In embodiments, a cell culture is agitated during $T_{culture}$, $T_{production}$ and/or $T_{harvest}$.

In embodiments, the method comprises recovering the expressed polypeptide.

In embodiments, cells or their products are in a harvest vessel at $T_{harvest}$.

In embodiments, a polypeptide is one of the polypeptides provided in Table 1 and 2, or variants thereof.

In embodiments, the polypeptide is an antibody, e.g., a monoclonal antibody, e.g., an IgG1 antibody, or a polynucleotide encoding the antibody. In embodiments, one or more cysteines in the antibody-encoded polynucleotide is replaced with another amino acid. In some embodiments, the one or more cysteines are replaced with one or more serine residues.

In embodiments, the cell line is derived from a mammalian cell.

In one aspect, the present disclosure features a method for producing a product described herein in a cell. In an embodiment, the product is a polypeptide, e.g., a recombinant polypeptide.

Examples of products that can be produced using any of the methods or compositions described herein include recombinant products, or products in which at least one portion or moiety is a result of genetic engineering. Recombinant products described herein are useful for diagnostic or therapeutic purposes. In one embodiment, a product comprises a polypeptide, such as an antibody molecule (e.g., a bispecific or multiformat antibody molecule), a fusion protein, or a protein-conjugate. The methods and compositions described herein may be particularly useful for products that are difficult to produce, e.g., in high quantities or with sufficient quality for commercial or therapeutic use, such as next generation biologics (e.g., fusion proteins, bispecific or multiformat antibody molecules, multimeric proteins, and glycosylated proteins). In one embodiment, a cell as described herein, e.g., for producing the product, expresses the product. In one embodiment, the cell comprises an exogenous nucleic acid that encodes a product described herein, e.g., a polypeptide selected from Tables 1, 2, 3, or 4. Additional examples of products are described in the section titled "Products".

In such embodiments, the increase or decrease of any of the aforementioned characteristics of the cell can be determined by comparison with a cell not having a modification.

The methods and bioreactors described herein result in increased production of the product as compared to a cell not subjected to the lowered temperature. An increase in production can be characterized by increased amounts, yields, or quantities of product produced by the cell and/or increased rate of production, where the rate of production is equivalent to the amount of product over time. In one embodiment, production of the product, e.g., a recombinant polypeptide, is increased by 1-fold, 2-fold, 5-fold, 10-fold, 20-fold, 50-fold, 100-fold, e.g., as compared to the production of by a cell not subjected to lowered temperature.

The methods and bioreactors described herein also can result in improved quality of the product as compared to a cell not subjected to lowered temperature. Improvements in the quality of the product can be characterized by one or more of: dissociation (e.g., a decrease in the dissociation of a polypeptide into a less active form); aggregation (e.g., a decrease in aggregates or aggregation); proper folding or assembly (e.g., a decrease in misfolded or unfolded products; or partially assembled or disassembled products); post-translation modification (e.g., increase or decrease in glycosylation heterogeneity, higher percentage of desired or predetermined post-translational modifications); fragmentation (e.g., a decrease in fragmentation); disulfide bond scrambling (e.g., a decrease in undesired isoforms or structures due to disulfide bond scrambling). In one embodiment, the quality of the product, e.g., recombinant polypeptide, is increased, e.g., by 1-fold, 2-fold, 5-fold, 10-fold, 20-fold, 50-fold, 100-fold, e.g., as compared to the quality of product produced by a cell not subjected to lowered temperature.

In embodiments, the method for producing a product as described herein can be performed with one or more additional steps to enhance stability or activity of a polypeptide. These include, but are not limited to: introducing a modification to the cell that improves ER processing capacity (ER expansion) or secretion; obtaining the product from the cell, or a descendent of the cell, or from the medium conditioned by the cell, or a descendent of the cell; separating the product from at least one cellular or medium component; and/or analyzing the product, e.g., for activity or for the presence of a structural moiety. In one embodiment, the method further comprises a step for improving ER processing capacity (or ER expansion) by introducing a nucleic acid encoding PD1, BiP, ERO, or XBP1. In one embodiment, the method further comprises an additional step for improving secretory capacity or rate of secretion by modulating SNARE machinery or other machinery involved in the secretory pathway, e.g., by introducing a nucleic acid encoding a SNARE component.

Products

Products suitable for the methods described herein include polypeptides, e.g., recombinant proteins; nucleic acid molecules, e.g., DNA or RNA molecules; multimeric proteins or complexes; lipid-encapsulated particles, e.g., virus-like particles, vesicles, or exosomes; or other molecules. In an embodiment, the product is a polypeptide, e.g., a recombinant polypeptide. For example, the recombinant polypeptide can be a difficult to express protein or a protein having complex and/or non-natural structures, such as a next generation biologic, e.g., a bispecific antibody molecule, a fusion protein, or a glycosylated protein.

In any of the methods described herein, the method for producing a product further comprises introducing to the cell an exogenous nucleic acid encoding the product, e.g., polypeptide, e.g., recombinant polypeptide.

In any of the compositions, preparations, bioreactors, or methods described herein, the product, e.g., recombinant polypeptide, is a therapeutic polypeptide or an antibody molecule, e.g., an antibody or an antibody fragment thereof. In one embodiment, the antibody molecule is a monoclonal antibody. In one embodiment, the antibody molecule is a bispecific antibody molecule, e.g., a BiTE (Bispecific T cell Engager), a DART (Dual Affinity Re-Targeting or Redirected T cell).

In one embodiment, the product, e.g., recombinant polypeptide, is selected from Table 1, Table 2, Table 3, or Table 4.

In embodiments, the product is stably expressed by the cell. In one embodiment, the exogenous nucleic acid encoding the product, e.g., recombinant polypeptide, is integrated into the chromosomal genome of the cell. Alternatively, the product is transiently expressed by the cell. In one embodiment, the exogenous nucleic acid encoding the product, e.g., the recombinant polypeptide, is not integrated into the chromosomal genome of the cell.

Host Cells

Provided herein are cells for producing the products described herein and methods of engineering such cells.

In any of the compositions, preparations, or methods described herein, the cell is a eukaryotic cell. In one embodiment, the cell is a mammalian cell, a yeast cell, an insect cell, an algae cell, or a plant cell. In one embodiment, the cell is a rodent cell. In one embodiment, the cell is a CHO cell. Examples of CHO cells include, but are not limited to, CHOK1, CHOK1SV, Potelligent CHOK1SV, CHO GS knockout, CHOK1SV GS-KO, CHOS, CHO DG44, CHO DXB11, CHOZN, or a CHO-derived cell.

In any of the compositions, preparations, or methods described herein, the cell is selected from the group consisting of HeLa, HEK293, H9, HepG2, MCF7, Jurkat, NIH3T3, PC12, PER.C6, BHK, VERO, SP2/0, NS0, YB2/0, EB66, C127, L cell, COS, e.g., COS1 and COST, QC1-3, CHOK1, CHOK1SV, Potelligent CHOK1SV, CHO GS knockout, CHOK1SV GS-KO, CHOS, CHO DG44, CHO DXB11, and CHOZN.

In one embodiment, the cell is a eukaryotic cell other than a mammalian cell, e.g., an insect, a plant, a yeast, or an algae cell. In one embodiment, the cell is a prokaryotic cell.

In any of the methods or cells, e.g., engineered cells, described herein, the cell expresses or comprises a product, e.g., a recombinant product, e.g., a next generation biologic selected from a group consisting of a bispecific antibody, a fusion protein, or a glycosylated protein.

In any of the methods or cells, e.g., engineered cells described herein, the cell is a CHO cell selected from the group consisting of CHOK1, CHOK1SV, Potelligent CHOK1SV, CHO GS knockout, CHOK1SV GS-KO, CHOS, CHO DG44, CHO DXB11, CHOZN, or a CHO-derived cell.

Compositions and Preparations

In one aspect, the present disclosure also features a preparation of a product described herein made by a method described herein. In one embodiment, at least 70, 80, 90, 95, 98 or 99%, by weight or number, of the products in the preparation are properly folded or assembled. In one embodiment, less than 50%, 40%, 30%, 25%, 20%, 15%, 10%, or 5%, by weight or number, of the products in the preparation are aggregated. In one embodiment, less than 50%, 40%, 30%, 25%, 20%, 15%, 10%, or 5%, by weight or number, of the products in the preparation are fragments of the product.

In one aspect, the present disclosure features a mixture comprising a cell described herein, e.g., a cell and a product produced by the cell. In one embodiment, the mixture comprises the product at a higher concentration, e.g., at least, 1, 2, 3, 4, 5, 6, 7, 8, 9, 10, 20, or 30% higher concentration, by weight or number, of product than would be seen without the disclosed process parameters. In one embodiment, at least 70, 80, 90, 95, 98 or 99%, by weight or number, of the products in the mixture are properly folded or assembled. In one embodiment, less than 50%, 40%, 30%, 25%, 20%, 15%, 10%, or 5%, by weight or number, of the products in the mixture are aggregated. In one embodiment, less than 50%, 40%, 30%, 25%, 20%, 15%, 10%, or 5%, by weight or number, of the products in the mixture are fragments of the product.

In one aspect, the present disclosure features a preparation of medium conditioned by culture of a cell subjected to the temperature-lowering modifications described herein. In one embodiment, the product is present in the preparation at a higher concentration, e.g., at least, 1, 2, 3, 4, 5, 6, 7, 8, 9, 10, 20, or 30% 100% higher concentration, by weight or number, than would be seen without the modification. In one embodiment, at least 70, 80, 90, 95, 98 or 99%, by weight or number, of the product in the preparation are properly folded or assembled. In one embodiment, less than 50%, 40%, 30%, 25%, 20%, 15%, 10%, or 5%, by weight or number, of the products in the preparation are aggregated. In one embodiment, less than 50%, 40%, 30%, 25%, 20%, 15%, 10%, or 5%, by weight or number, of the products in the preparation are fragments of the product.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and are not intended to be limiting. Headings, sub-headings or numbered or lettered elements, e.g., (a), (b), (i) etc, are presented merely for ease of reading. The use of headings or numbered or lettered elements in this document does not require the steps or elements be performed in alphabetical order or that the steps or elements are necessarily discrete from one another. Other features, objects, and advantages of the invention will be apparent from the description and drawings, and from the claims.

BRIEF DESCRIPTION OF THE DRAWINGS

FIG. 4 is a representation of non-reduced SDS polyacrylamide gel samples prepared without mitigation (left panel) and with mitigation (right panel) for an IgG1 monoclonal antibody.

FIG. 6 shows a graph of sparge flow of air and oxygen for cellular oxygen demand (sLPM) and production culture temperature over elapsed time, labelling stages and transition points.

FIGS. 7A and 7B show example control profiles of cultures when the sparged air and oxygen are fixed in the production culture during harvesting (FIG. 7A) and when the sparged air and oxygen are fixed in the production culture during harvesting to limit DOT of culture to ~200% air saturation maximum (FIG. 7B).

DETAILED DESCRIPTION

Figure 1:
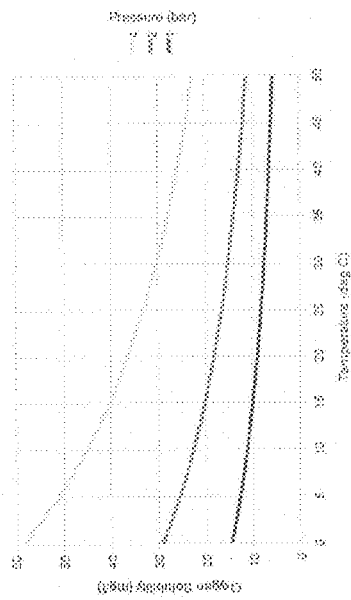
FIG. 1 shows the interrelationship of temperature, oxygen solubility, and the oxygen utilization rate. (OUR).

The present disclosure features methods and compositions for obtaining higher yields of a product by cooling the cell culture. Thus, cells show improved quality as compared to the yield and quality obtained from current production methods. The methods and compositions described herein are also useful for engineering cells or cell lines with improved productivity, product quality, robustness, and/or culture viability, as compared to the cell expression systems currently used to produce recombinant products.

The methods are suitable for producing next generation biologics. As these methods continue to gain therapeutic utility in patients, the demand for large quantities of next generation biologic products having a high grade of quality for therapeutic use, as well as efficient means for production and efficient development of production cell lines will escalate. Furthermore, many next generation biologics are difficult to express and produce in conventional cell lines using conventional expression techniques known in the art. The current methods are not sufficient to produce these products in the large quantities and at the high grade of quality required for clinical use. The cooling methods described herein overcome these obstacles.

Definitions

Unless defined otherwise, all technical and scientific terms used herein have the same meaning as commonly understood by one of ordinary skill in the art to which the invention pertains. Although any methods and materials similar or equivalent to those described herein can be used in the practice of and/or for the testing of the present invention, the preferred materials and methods are described herein. In describing and claiming the present invention, the following terminology will be used according to how it is defined, where a definition is provided.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "a cell" can mean one cell or more than one cell.

"Dissociation", as used herein, refers to cleavage or dissociation of disulfide bonds, via reduction between cysteine residues within a polypeptide and between polypeptides.

"Endogenous", as used herein, refers to any material from or naturally produced inside an organism, cell, tissue or system.

"Exogenous", as used herein, refers to any material introduced to or produced outside of an organism, cell, tissue or system. Accordingly, "exogenous nucleic acid" refers to a nucleic acid that is introduced to or produced outside of an organism, cell, tissue or system. In an embodiment, sequences of the exogenous nucleic acid are not naturally produced, or cannot be naturally found, inside the organism, cell, tissue, or system that the exogenous nucleic acid is introduced into. In embodiments, non-naturally occurring products, or products containing portions that are non-naturally occurring are exogenous materials with respect to the host cells described herein.

"Heterologous", as used herein, refers to any material from one species, when introduced to an organism, cell, tissue or system from a different species. In embodiments, a heterologous material also encompasses a material that includes portions from one or multiple species or portions that are non-naturally occurring. By way of example, in an embodiment, a nucleic acid encoding a fusion protein wherein a portion of the fusion protein is human, a portion of the fusion protein is bacteria, and a portion of the fusion protein is non-naturally occurring, and the nucleic acid is introduced to a human cell, the nucleic acid is a heterologous nucleic acid.

"Peptide," "polypeptide," and "protein", as used interchangeably herein, refer to a compound comprised of amino acid residues covalently linked by peptide bonds, or by means other than peptide bonds. A protein or peptide must contain at least two amino acids, and no limitation is placed on the maximum number of amino acids that can comprise a protein's or peptide's sequence. In one embodiment, a protein may comprise of more than one, e.g., two, three, four, five, or more, polypeptides, in which each polypeptide is associated to another by either covalent or non-covalent bonds/interactions. Polypeptides include any peptide or protein comprising two or more amino acids joined to each other by peptide bonds or by means other than peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others.

"Recombinant product" refers to a product that can be produced by a cell or a cell-free system. The product can be a molecule, a nucleic acid, a polypeptide, or any hybrid thereof. A recombinant product is one for at which at least one component of the product or at least one nucleotide of a sequence which controls the production or expression of the product, was formed by genetic engineering. Genetic engineering as used herein to generate a recombinant product or a construct that encodes a recombinant product encompasses recombinant DNA expression techniques known in the art (e.g., as described in Current Protocols in Molecular Biology); site-directed, scanning, or random mutagenesis; CRISPR strategies; and zinc finger nuclease (ZFN) strategies. In one embodiment, the recombinant product is a recombinant polypeptide. In one embodiment, the recombinant product is a naturally occurring product. In one embodiment, the recombinant product is a non-naturally occurring product, e.g., a synthetic product. In one embodiment, a portion of the recombinant product is naturally occurring, while another portion of the recombinant product is non-naturally occurring. In another embodiment, a first portion of the recombinant product is one naturally occurring molecule, while another portion of the recombinant product is another naturally occurring molecule that is different from the first portion. In some embodiments, a recombinant product (e.g., recombinant polypeptide) is a stabilized product. A stabilized product is a product produced by a cell, e.g., a recombinant host cell, under conditions that increase the likelihood of proper folding and bond arrangement, e.g., correctly paired disulphide bonds, and decrease the likelihood of dissociation of multi-subunit polypeptides. In some embodiments, a stabilized product is a stabilized protein. A stabilized protein is a protein produced by a cell under conditions that increase the likelihood of proper protein folding and bond arrangement, e.g., proper disulfide bond arrangement, and decrease the likelihood of dissociation of multi-subunit polypeptides. For example, a stabilized protein may be produced at temperatures and oxygenation levels that produce an oxidizing environment relative to the temperatures and oxygenation levels used to produce a non-stabilized protein, increasing the likelihood of retaining correct disulfide bonds and decreasing the likelihood that multi-subunit polypeptides can dissociate from one another. Stabilized products, e.g., stabilized proteins, may also be isolated, e.g., purified by a series of separation/chromatographic steps, from a cell or cell culture under conditions that promote proper folding and bond arrangement. A preparation of stabilized product, e.g., stabilized protein, is a preparation prepared, e.g., from a cell, e.g., a recombinant host cell, under conditions that increase the likelihood of proper folding and bond arrangement, and decrease the likelihood of dissociation of multi-subunit polypeptides. For example, a preparation of stabilized product, e.g., stabilized protein, is more likely to comprise product, e.g., protein, with correct disulfide bonds and less likely to comprise dissociated product, e.g., protein, e.g., dissociated subunits of multi-subunit polypeptides. See, e.g., Wal Keen Chung et. al 2017, Michael W Handlogten et. al 2017, and Brian Mullan et. al 2011 for a greater in depth discussion on the subject of dissociation of product, e.g., antibodies.

"Recombinant polypeptide" refers to a polypeptide that can be produced by a cell described herein. A recombinant polypeptide is one for which at least one nucleotide of the sequence encoding the polypeptide, or at least one nucleotide of a sequence which controls the expression of the polypeptide, was formed by genetic engineering or manipulation (of the cell or of a precursor cell). E.g., at least one nucleotide was altered, e.g., it was introduced into the cell or it is the product of a genetically engineered rearrangement. In an embodiment, the sequence of a recombinant polypeptide does not differ from a naturally or non-naturally occurring isoform of the polypeptide or protein. In an embodiment, the amino acid sequence of the recombinant polypeptide differs from the sequence of a naturally occurring or a non-naturally isoform of the polypeptide or protein. In an embodiment, the recombinant polypeptide and the cell are from the same species. In an embodiment, the amino acid sequence of the recombinant polypeptide is the same as or is substantially the same as, or differs by no more than 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 99% from, a polypeptide encoded by the endogenous genome of the cell. In an embodiment, the recombinant polypeptide and the cell are from the same species, e.g., the recombinant polypeptide is a human polypeptide and the cell is a human cell. In an embodiment, the recombinant polypeptide and the cell are from different species, e.g., the recombinant polypeptide is a human polypeptide and the cell is a non-human, e.g., a rodent, e.g., a CHO, other mammalian cell, an insect cell, a plant, a fungi or a bacterial cell. In an embodiment, the recombinant polypeptide is exogenous to the cell, in other words, the cell is from a first species and the recombinant polypeptide is from a second species. In one embodiment, the polypeptide is a synthetic polypeptide. In one embodiment, the polypeptide is derived from a non-naturally occurring source. In an embodiment, the recombinant polypeptide is a human polypeptide or protein which does not differ in amino acid sequence from a naturally or non-naturally occurring isoform of the human polypeptide or protein. In an embodiment, the recombinant polypeptide differs from a naturally or non-naturally occurring isoform of the human polypeptide or protein at no more than 1, 2, 3, 4, 5, 10, 15 or 20 amino acid residues. In an embodiment, the recombinant polypeptide differs from a naturally occurring isoform of the human polypeptide at no more than 1%, 2%, 3%, 4%, 5%, 6%, 7%, 8%, 9%, 10%, or 15% of its amino acid residues. In embodiments where a portion of the recombinant polypeptide comprises a sequence derived from a portion of a naturally or non-naturally occurring isoform of a human polypeptide, the portion of the recombinant polypeptide differs from the corresponding portion of the naturally or non-naturally occurring isoform by no more than 1, 2, 3, 4, 5, 10, 15, or 20 amino acid residues, or 1%, 2%, 3%, 4%, 5%, 6%, 7%, 8%, 9%, 10%, or 15% of its amino acid residues.

Oxygenation level and level of oxygenation are used interchangeably, and as used herein refer to a level of dissolved oxygen in a volume of liquid or gas, e.g., in a culture. Oxygenation level can be described in units of dissolved oxygen tension (DOT), e.g., in terms of percentage of air saturation (e.g., the percentage of the level of oxygen in air).

A production culture, as used herein, refers to a mixture of growth media and cells (e.g., at least one cell), e.g., recombinant cells, e.g., recombinant host cells expressing a product, e.g., protein, cellular factor, e.g., enzymes and metabolites. In some embodiments, a production culture progresses through one or more culture phases (e.g., sequential and/or overlapping culture phases) comprising cell growth/division characteristics. In some embodiments, treatment of a production culture changes as described herein as the production culture progresses through different phases. Production phase, as used herein, refers to a phase of a production culture starting at inoculation and ending upon reaching a specific criteria (e.g., end of a process or time period, e.g., 10-30 days, e.g., 15-20 days) or upon reaching a specific cell viability criteria (e.g., less than 90, 80, 70, 60, 50, 40, 30, 20, or 10% viability, e.g., less than 50% viability). Production phase may include an exponential growth phase in which cell growth and/or division is exponential. Production phase may include a post-growth phase that follows exponential growth phase, in which cell growth and/or division is in the linear phase of a growth curve, e.g., the rate of cell growth and/or division has decreased relative to exponential growth phase. In some embodiments, separation of cells from the production supernatant, e.g., harvest, and further separation or purification steps, e.g., post-harvest, are phases that follow the end of production phase.

Redox potential difference, as used herein, describes a comparison of the redox potentials of two or more compounds, e.g., products, e.g., stabilized or non-stabilized products, e.g., stabilized or non-stabilized proteins. For example, a stabilized product may have a redox potential A, whereas a non-stabilized product may have a redox potential B; there would then be a redox potential difference of A–B (A minus B) from a stabilized product to a non-stabilized product, or a redox potential difference of B–A (B–A) from a non-stabilized product to a stabilized product. E.g. a higher the absolute negative redox potential the more reductive the environment and the goal of the present invention is to create a more oxidative environment by methods disclosed herein thereby reducing the absolute negative redox potential toward a positive redox potential.

Operably coupled, as used herein, describes a relationship between vessels. In an embodiment, culture media or production culture can be transmitted between operably coupled vessels. In an embodiment, flow of culture between operably coupled vessels occurs in a controlled manner, e.g., making use of pumps, filters, sensors, means for maintaining or altering culture conditions, and/or means for monitoring flow of liquid.

In some embodiments, a method of the disclosure comprises or a bioreactor of the disclosure is capable of maintaining a production culture, cells of the production culture, or supernatant from the production culture, at different temperatures throughout different phases. $T_{culture}$, as used herein, is the temperature at which the cells of a production culture are grown, e.g., in growth medium, from the start of inoculation to the end of production phase to produce a production culture in which a protein is produced. In some embodiments, $T_{culture}$ is 30° C.-38° C. $T_{production}$, as used herein, is the first temperature to which the production culture is cooled after post-exponential growth phase. In some embodiments, $T_{production}$ is less than 35° C., 34° C., 33° C., 32° C., 31° C., or 30° C., e.g., 30° C.-33° C. $T_{harvest}$, as used herein, is the second temperature to which the production culture is cooled prior to harvest (e.g., the separation of cells from supernatant). In some embodiments, $T_{harvest}$ is 29° C., 28° C., 27° C., 26° C., 25° C., 24° C., 23° C., 22° C., 21° C., 20° C., 19° C., 18° C., 17° C., 16° C., 15° C., 14° C., 13° C., 12° C., 11° C., 10° C., 9° C., 8° C., 7° C., 6° C., 5° C., or 4° C. In one embodiment, $T_{harvest}$ is 12° C.-18° C., e.g., 15° C. In one embodiment, $T_{harvest}$ is less than 6° C., 7° C., 8° C., 9° C., 10° C., 11° C., 12° C., 13° C., 14° C., 15° C., 16° C., 17° C., 18° C., 19° C., 20° C., 21° C., 22° C., 23° C. or 24° C. In one embodiment, $T_{harvest}$ is 15° C.±3° C.

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

Products

Provided herein are methods and compositions for engineering or making a cell or a cell-free expression system capable of producing high yields of a product and/or improved product quality (e.g., stabilized product, e.g., stabilized protein) by lowering the temperature at which the cell is expressed. Products described herein include polypeptides, e.g., recombinant proteins; multimeric proteins or complexes; lipid-encapsulated particles, e.g., virus-like particles, vesicles, or exosomes; or other molecules. In an embodiment, the product is a polypeptide, e.g., a recombinant polypeptide. In an embodiment, the product is an exosome. For example, the recombinant polypeptide can be a difficult to express protein or a protein having complex and/or non-natural structures, such as a next generation biologic, e.g., a bispecific antibody molecule, a fusion protein, or a glycosylated protein.

In embodiments, the cell or cell line generated by the methods or compositions described herein produces a product, e.g., a recombinant polypeptide, e.g., a stabilized protein, useful in the treatment of a medical condition, disorder or disease. Examples of medical conditions, disorders or diseases include, but are not limited to, metabolic disease or disorders (e.g., metabolic enzyme deficiencies), endocrine disorders (e.g., hormone deficiencies), dysregulation of hemostasis, thrombosis, hematopoietic disorders, pulmonary disorders, gastro-intestinal disorders, autoimmune diseases, immuno-dysregulation (e.g., immunodeficiency), infertility, transplantation, cancer, and infectious diseases.

In embodiments, the product is an exogenous protein, e.g., a protein that is not naturally expressed by the cell. In one embodiment, the protein is from one species while the cell is from a different species. In another embodiment, the protein is a non-naturally occurring protein.

In other embodiments, the product is a protein that is endogenously expressed by the cell. In one embodiment, the product is a protein that is endogenously expressed by the cell at endogenous or natural levels. The present methods and compositions described herein are used to increase the production and quality of the endogenous product, e.g., a naturally occurring product that is naturally produced by the cell. In another embodiment, an exogenous nucleic acid encoding the product, e.g., protein, is introduced to and expressed by the cell. In another embodiment, an exogenous nucleic acid that increases the expression of a product that is endogenously expressed by the cell is introduced into the cell. By way of example, the exogenous nucleic acid comprises a sequence that activates the promoter that controls the expression of an endogenous product of the cell.

The recombinant product can be a therapeutic product or a diagnostic product, e.g., useful for drug screening. The therapeutic or diagnostic product can include, but is not limited to, an antibody molecule, e.g., an antibody or an antibody fragment, a fusion protein, a hormone, a cytokine, a growth factor, an enzyme, a glycoprotein, a lipoprotein, a reporter protein, a therapeutic peptide, or a structural and/or functional fragment or hybrid of any of these. In other embodiments, the therapeutic or diagnostic product is a synthetic polypeptide, e.g., wherein the entire polypeptide or portions thereof is not derived from or has any sequence or structural similarity to any naturally occurring polypeptide, e.g., a naturally occurring polypeptide described above.

In one embodiment, the recombinant product is an antibody molecule. In one embodiment, the recombinant product is a therapeutic antibody molecule. In another embodiment, the recombinant product is a diagnostic antibody molecule, e.g., a monoclonal antibody useful for imaging techniques or diagnostic tests.

An antibody molecule, as used herein, is a protein, or polypeptide sequence derived from an immunoglobulin molecule which specifically binds with an antigen. In an embodiment, the antibody molecule is a full-length antibody or an antibody fragment. Antibodies and multiformat proteins can be polyclonal or monoclonal, multiple or single chain, or intact immunoglobulins, and may be derived from natural sources or from recombinant sources. Antibodies can be tetramers of immunoglobulin molecules. In an embodiment, the antibody is a monoclonal antibody. The antibody may be a human or humanized antibody. In one embodiment, the antibody is an IgA, IgG, IgD, or IgE antibody. In one embodiment, the antibody is an IgG1, IgG2, IgG3, or IgG4 antibody.

"Antibody fragment" refers to at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', F(ab')$_2$, and Fv fragments, scFv antibody fragments, linear antibodies, single domain antibodies such as sdAb (either VL or VH), camelid VHH domains, and multi-specific antibodies formed from antibody fragments such as a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (Fn3)(see U.S. Pat. No. 6,703,199, which describes fibronectin polypeptide minibodies).

In embodiments, the polypeptide is, e.g., BOTOX, Myobloc, Neurobloc, Dysport (or other serotypes of botulinum neurotoxins), alglucosidase alpha, daptomycin, YH-16, choriogonadotropin alpha, filgrastim, cetrorelix, interleukin-2, aldesleukin, teceleulin, denileukin diftitox, interferon alpha-n3 (injection), interferon alpha-nl, DL-8234, interferon, Suntory (gamma-1a), interferon gamma, thymosin alpha 1, tasonermin, DigiFab, ViperaTAb, EchiTAb, CroFab, nesiritide, abatacept, alefacept, Rebif, eptoterminalfa, teriparatide, calcitonin, etanercept, hemoglobin glutamer 250 (bovine), drotrecogin alpha, collagenase, carperitide, recombinant human epidermal growth factor, DWP401, darbepoetin alpha, epoetin omega, epoetin beta, epoetin alpha, desirudin, lepirudin, bivalirudin, nonacog alpha, Mononine, eptacog alpha (activated), recombinant Factor VIII+VWF, Recombinate, recombinant Factor VIII, Factor VIII (recombinant), Alphnmate, octocog alpha, Factor VIII, palifermin, Indikinase, tenecteplase, alteplase, pamiteplase, reteplase, nateplase, monteplase, follitropin alpha, rFSH, hpFSH, micafungin, pegfilgrastim, lenograstim, nartograstim, sermorelin, glucagon, exenatide, pramlintide, iniglucerase, galsulfase, Leucotropin, molgramostim, triptorelin acetate, histrelin (Hydron), deslorelin, histrelin, nafarelin, leuprolide (ATRIGEL), leuprolide (DUROS), goserelin, Eutropin, somatropin, mecasermin, enlfavirtide, Org-33408, insulin glargine, insulin glulisine, insulin (inhaled), insulin lispro, insulin deternir, insulin (RapidMist), mecasermin rinfabate, anakinra, celmoleukin, 99 mTc-apcitide, myelopid, Betaseron, glatiramer acetate, Gepon, sargramostim, oprelvekin, human leukocyte-derived alpha interferons, Bilive, insulin (recombinant), recombinant human insulin, insulin aspart, mecasenin, Roferon-A, interferon-alpha 2, Alfaferone, interferon alfacon-1, interferon alpha, Avonex' recombinant human luteinizing hormone, dornase alpha, trafermin, ziconotide, taltirelin, diboterminalfa, atosiban, becaplermin, eptifibatide, Zemaira, CTC-111, Shanvac-B, octreotide, lanreotide, ancestirn, agalsidase beta, agalsidase alpha, laronidase, prezatide copper acetate, rasburicase, ranibizumab, Actimmune, PEG-Intron, Tricomin, recombinant human parathyroid hormone (PTH) 1-84, epoetin delta, transgenic antithrombin III, Granditropin, Vitrase, recombinant insulin, interferon-alpha, GEM-21S, vapreotide, idursulfase, omnapatrilat, recombinant serum albumin, certolizumab pegol, glucarpidase, human recombinant C1 esterase inhibitor, lanoteplase, recombinant human growth hormone, enfuvirtide, VGV-1, interferon (alpha), lucinactant, aviptadil, icatibant, ecallantide, omiganan, Aurograb, pexigananacetate, ADI-PEG-20, LDI-200, degarelix, cintredelinbesudotox, Favld, MDX-1379, ISAtx-247, liraglutide, teriparatide, tifacogin, AA4500, T4N5 liposome lotion, catumaxomab, DWP413, ART-123, Chrysalin, desmoteplase, amediplase, corifollitropinalpha, TH-9507, teduglutide, Diamyd, DWP-412, growth hormone, recombinant G-CSF, insulin, insulin (Technosphere), insulin (AERx), RGN-303, DiaPep277, interferon beta, interferon alpha-n3, belatacept, transdermal insulin patches, AMG-531, MBP-8298, Xerecept, opebacan, AIDSVAX, GV-1001, LymphoScan, ranpirnase, Lipoxysan, lusupultide, MP52, sipuleucel-T, CTP-37, Insegia, vitespen, human thrombin, thrombin, TransMID, alfimeprase, Puricase, terlipressin, EUR-1008M, recombinant FGF-I, BDM-E, rotigaptide, ETC-216, P-113, MBI-594AN, duramycin, SCV-07, OPI-45, Endostatin, Angiostatin, ABT-510, Bowman Birk Inhibitor, XMP-629, 99 mTc-Hynic-Annexin V, kahalalide F, CTCE-9908, teverelix, ozarelix, rornidepsin, BAY-504798, interleukin4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DMI, SB-249553, Oncovax-CL, OncoVax-P, BLP-25, CerVax-16, MART-1, gp100, tyrosinase, nemifitide, rAAT, CGRP, pegsunercept, thymosin-beta4, plitidepsin, GTP-200, ramoplanin, GRASPA, OBI-1, AC-100, salmon calcitonin (eligen), examorelin, capromorelin, Cardeva, velafermin, 131I-TM-601, KK-220, T-10, ularitide, depelestat, hematide, Chrysalin, rNAPc2, recombinant Factor V111 (PEGylated liposomal), bFGF, PEGylated recombinant staphylokinase variant, V-10153, SonoLysis Prolyse, NeuroVax, CZEN-002, rGLP-1, BIM-51077, LY-548806, exenatide (controlled release, Medisorb), AVE-0010, GA-GCB, avorelin, ACM-9604, linaclotid eacetate, CETi-1, Hemospan, VAL, fast-acting insulin (injectable, Viadel), insulin (eligen), recombinant methionyl human leptin, pitrakinra, Multikine, RG-1068, MM-093, NBI-6024, AT-001, PI-0824, Org-39141, Cpn10, talactoferrin, rEV-131, rEV-131, recombinant human insulin, RPI-78M, oprelvekin, CYT-99007 CTLA4-Ig, DTY-001, valategrast, interferon alpha-n3, IRX-3, RDP-58, Tauferon, bile salt stimulated lipase, Merispase, alaline phosphatase, EP-2104R, Melanotan-II, bremelanotide, ATL-104, recombinant human microplasmin, AX-200, SEMAX, ACV-1, Xen-2174, CJC-1008, dynorphin A, SI-6603, LAB GHRH, AER-002, BGC-728, ALTU-135, recombinant neuraminidase, Vacc-5q, Vacc-4x, Tat Toxoid, YSPSL, CHS-13340, PTH(1-34) (Novasome), Ostabolin-C, PTH analog, MBRI-93.02, MTB72F, MVA-Ag85A, FARA04, BA-210, recombinant plague FIV, AG-702, OxSODrol, rBetV1, Der-p1/Der-p2/Der-p7, PR1 peptide antigen, mutant ras vaccine, HPV-16 E7 lipopeptide vaccine, labyrinthin, WT1-peptide, IDD-5, CDX-110, Pentrys, Norelin, CytoFab, P-9808, VT-111, icrocaptide, telbermin, rupintrivir, reticulose, rGRF, HA, alpha-galactosidase A, ACE-011, ALTU-140, CGX-1160, angiotensin, D-4F, ETC-642, APP-018, rhMBL, SCV-07, DRF-7295, ABT-828, ErbB2-specific immunotoxin, DT3SSIL-3, TST-10088, PRO-1762, Combotox, cholecystokinin-B/gastrin-receptor binding peptides, 111In-hEGF, AE-37, trasnizumab-DM1, Antagonist G, IL-12, PM-02734, IMP-321, rhIGF-BP3, BLX-883, CUV-1647, L-19 based ra, Re-188-P-2045, AMG-386, DC/1540/KLH, VX-001, AVE-9633, AC-9301, NY-ESO-1 (peptides), NA17.A2 peptides, CBP-501, recombinant human lactoferrin, FX-06, AP-214, WAP-8294A, ACP—HIP, SUN-11031, peptide YY [3-36], FGLL, atacicept, BR3-Fc, BN-003, BA-058, human parathyroid hormone 1-34, F-18-CCR1, AT-1100, JPD-003, PTH (7-34) (Novasome), duramycin, CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix, EP-51216, hGH, OGP-I, sifuvirtide, TV4710, ALG-889, Org-41259, rhCC10, F-991, thymopentin, r(m)CRP, hepatoselective insulin, subalin, L19-IL-2 fusion protein, elafin, NMK-150, ALTU-139, EN-122004, rhTPO, thrombopoietin receptor agonist, AL-108, AL-208, nerve growth factor antagonists, SLV-317, CGX-1007, INNO-105, teriparatide (eligen), GEM-OS1, AC-162352, PRX-302, LFn-p24 fusion, EP-1043, gpE1, gpE2, MF-59, hPTH(1-34), 768974, SYN-101, PGN-0052, aviscumnine, BIM-23190, multi-epitope tyrosinase peptide, enkastim, APC-8024, GI-5005, ACC-001, TTS-CD3, vascular-targeted TNF, desmopressin, onercept, and TP-9201.

In some embodiments, the polypeptide is adalimumab (HUMIRA), infliximab (REMICADE™), rituximab (RITUXAN™/MAB THERA™) etanercept (ENBREL™) bevacizumab (AVASTIN™), trastuzumab (HERCEPTIN™), pegrilgrastim (NEULASTA™), or any other suitable polypeptide including biosimilars and biobetters.

Other suitable polypeptides are those listed below and in Table 1 of US2016/0097074:

TABLE I

| Protein Product | Reference Listed Drug |
| --- | --- |
| interferon gamma-1b | Actimmune ® |
| alteplase; tissue plasminogen activator | Activase ®/Cathflo ® |
| Recombinant antihemophilic factor | Advate |
| human albumin | Albutein ® |
| Laronidase | Aldurazyme ® |
| interferon alfa-N3, human leukocyte derived | Alferon N ® |
| human antihemophilic factor | Alphanate ® |
| virus-filtered human coagulation factor IX | AlphaNine ® SD |

TABLE I-continued

| Protein Product | Reference Listed Drug |
| --- | --- |
| Alefacept; recombinant dimeric fusion protein LFA3-Ig | Amevive ® |
| Bivalirudin | Angiomax ® |
| darbepoetin alfa | Aranesp ™ |
| Bevacizumab | Avastin ™ |
| interferon beta-1a; recombinant | Avonex ® |
| coagulation factor IX | BeneFix ™ |
| Interferon beta-1b | Betaseron ® |
| Tositumomab | BEXXAR ® |
| antihemophilic factor | Bioclate ™ |
| human growth hormone | BioTropin ™ |
| botulinum toxin type A | BOTOX ® |
| Alemtuzumab | Campath ® |
| acritumornab; technetium-99 labeled | CEA-Scan ® |
| alglucerase; modified form of beta-glucocerebrosidase | Ceredase ® |
| imiglucerase; recombinant form of beta-glucocerebrosidase | Cerezyme ® |
| crotalidae polyvalent immune Fab, ovine | CroFab ™ |
| digoxin immune fab [ovine] | DigiFab ™ |
| Rasburicase | Elitek ® |
| Etanercept | ENBREL ® |
| epoietin alfa | Epogen ® |
| Cetuximab | Erbitux ™ |
| algasidase beta | Fabrazyme ® |
| Urofollitropin | Fertinex ™ |
| follitropin beta | Follistim ™ |
| Teriparatide | FORTEO ® |
| human somatropin | GenoTropin ® |
| Glucagon | GlucaGen ® |
| follitropin alfa | Gonal-F ® |
| antihemophilic factor | Helixate ® |
| Antihemophilic Factor; Factor XIII | HEMOFIL |
| adefovir dipivoxil | Hepsera ™ |
| Trastuzumab | Herceptin ® |
| Insulin | Humalog ® |
| antihemophilic factor/von Willebrand factor complex-human | Humate-P ® |
| Somatotropin | Humatrope ® |
| Adalimumab | HUMIRA ™ |
| human insulin | Humulin ® |
| recombinant human hyaluronidase | Hylenex ™ |
| interferon alfacon-1 | Infergen ® |
| eptifibatide | Integrilin ™ |
| alpha-interferon | Intron A ® |
| Palifermin | Kepivance |
| Anakinra | Kineret ™ |
| antihemophilic factor | Kogenate ® FS |
| insulin glargine | Lantus ® |
| granulocyte macrophage colony-stimulating factor | Leukine ®/Leukine ® Liquid |
| lutropin alfa for injection | Luveris |
| OspA lipoprotein | LYMErix ™ |
| Ranibizumab | LUCENTIS ® |
| gemtuzumab ozogamicin | Mylotarg ™ |
| Galsulfase | Naglazyme ™ |
| Nesiritide | Natrecor ® |
| Pegfilgrastim | Neulasta ™ |
| Oprelvekin | Neumega ® |
| Filgrastim | Neupogen ® |
| Fanolesomab | NeutroSpec ™ (formerly LeuTech ®) |
| somatropin [rDNA] | Norditropin ®/Norditropin Nordiflex ® |
| Mitoxantrone | Novantrone ® |
| insulin; zinc suspension; | Novolin L ® |
| insulin; isophane suspension | Novolin N ® |
| insulin, regular; | Novolin R ® |
| Insulin | Novolin ® |
| coagulation factor VIIa | NovoSeven ® |
| Somatropin | Nutropin ® |
| immunoglobulin intravenous | Octagam ® |
| PEG-L-asparaginase | Oncaspar ® |
| abatacept, fully human soluable fusion protein | Orencia ™ |
| muromomab-CD3 | Orthoclone OKT3 ® |
| high molecular weight hyaluronan | Orthovisc ® |
| human chorionic gonadotropin | Ovidrel ® |
| live attenuated Bacillus Calmette-Guerin | Pacis ® |

TABLE I-continued

| Protein Product | Reference Listed Drug |
|---|---|
| peginterferon alfa-2a | Pegasys ® |
| pegylated version of interferon alfa-2b | PEG-Intron ™ |
| Abarelix (injectable suspension); gonadotropin-releasing hormone antagonist | Plenaxis ™ |
| epoietin alfa | Procrit ® |
| Aldesleukin | Proleukin, IL-2 ® |
| Somatrem | Protropin ® |
| dornase alfa | Pulmozyme ® |
| Efalizumab; selective reversible T-cell blocker | RAPTIVA ™ |
| combination of ribavirin and alpha interferon | Rebetron ™ |
| Interferon beta 1a | Rebif ® |
| antihemophilic factor | Recombinate ® rAHF/ |
| antihemophilic factor | ReFacto ® |
| Lepirudin | Refludan ® |
| Infliximab | REMICADE ® |
| Abciximab | ReoPro ™ |
| Reteplase | Retavase ™ |
| Rituxima | Rituxan ™ |
| interferon alfa-2$^a$ | Roferon-A ® |
| Somatropin | Saizen ® |
| synthetic porcine secretin | SecreFlo ™ |
| Basiliximab | Simulect ® |
| Eculizumab | SOLARIS (R) |
| Pegvisomant | SOMAVERT ® |

TABLE I-continued

| Protein Product | Reference Listed Drug |
|---|---|
| Palivizumab; recombinantly produced, humanized mAb | Synagis ™ |
| thyrotropin alfa | Thyrogen ® |
| Tenecteplase | TNKase ™ |
| Natalizumab | TYSABRI ® |
| human immune globulin intravenous 5% and 10% solutions | Venogiobulin-S ® |
| interferon alfa-n1, lymphoblastoid | Wellferon ® |
| drotrecogin alfa | Xigris ™ |
| Omalizumab; recombinant DNA-derived humanized monoclonal antibody targeting immunoglobulin-E | Xolair ® |
| Daclizumab | Zenapax ® |
| ibritumomab tiuxetan | Zevalin ™ |
| Somatotropin | Zorbtive ™ (Serostim ®) |

In embodiments, the polypeptide is a hormone, blood clotting/coagulation factor, cytokine/growth factor, antibody molecule, fusion protein, protein vaccine, or peptide as shown in Table 2.

Exemplary recombinant products that can be produced using the methods described herein include, but are not limited to, those provided in the tables below.

TABLE 2

Exemplary Products

| Therapeutic Product type | Product | Trade Name |
|---|---|---|
| Hormone | Erythropoietin, Epoein-α | Epogen, Procrit |
| | Darbepoetin-α | Aranesp |
| | Growth hormone (GH), somatotropin | Genotropin, Humatrope, Norditropin, NovIVitropin, Nutropin, Omnitrope, Protropin, Siazen, Serostim, Valtropin |
| | Human follicle-stimulating hormone (FSH) | Gonal-F, Follistim |
| | Human chorionic gonadotropin | Ovidrel |
| | Lutropin-α | Luveris |
| | Glucagon | GlcaGen |
| | Growth hormone releasing hormone (GHRH) | Geref |
| | Secretin | ChiRhoStim (human peptide), SecreFlo (porcine peptide) |
| | Thyroid stimulating hormone (TSH), thyrotropin | Thyrogen |
| Blood Clotting/Coagulation Factors | Factor VIIa | NovoSeven |
| | Factor VIII | Bioclate, Helixate, Kogenate, Recombinate, ReFacto |
| | Factor IX | Benefix |
| | Antithrombin III (AT-III) | Thrombate III |
| | Protein C concentrate | Ceprotin |
| Cytokine/Growth factor | Type I alpha-interferon | Infergen |
| | Interferon-αn3 (IFNαn3) | Alferon N |
| | Interferon-β1a (rIFN-β) | Avonex, Rebif |
| | Interferon-β1b (rIFN-β) | Betaseron |
| | Interferon-γ1b (IFN γ) | Actimmune |
| | Aldesleukin (interleukin 2(IL2), epidermal theymocyte activating factor; ETAF | Proleukin |
| | Palifermin (keratinocyte growth factor; KGF) | Kepivance |
| | Becaplemin (platelet-derived growth factor; PDGF) | Regranex |
| | Anakinra (recombinant IL1 antagonist) | Anril, Kineret |
| Antibody molecules | Bevacizumab (VEGFA mAb) | Avastin |
| | Cetuximab (EGFR mAb) | Erbitux |
| | Panitumumab (EGFR mAb) | Vectibix |
| | Alemtuzumab (CD52 mAb) | Campath |
| | Rituximab (CD20 chimeric Ab) | Rituxan |
| | Trastuzumab (HER2/Neu mAb) | Herceptin |
| | Abatacept (CTLA Ab/Fc fusion) | Orencia |
| | | Humira |
| | | Enbrel |
| | | Remicade |

TABLE 2-continued

Exemplary Products

| Therapeutic Product type | Product | Trade Name |
|---|---|---|
| | Adalimumab (TNFα mAb) | Amevive |
| | Etanercept (TNF receptor/Fc fusion) | Raptiva |
| | Infliximab (TNFα chimeric mAb) | Tysabri |
| | Alefacept (CD2 fusion protein) | Soliris |
| | Efalizumab (CD11a mAb) | Orthoclone, OKT3 |
| | Natalizumab (integrin α4 subunit mAb) | |
| | Eculizumab (C5mAb) | |
| | Muromonab-CD3 | |
| Other: Fusion proteins/Protein vaccines/Peptides | Insulin | Humulin, Novolin |
| | Hepatitis B surface antigen (HBsAg) | Engerix, Recombivax HB |
| | HPV vaccine | Gardasil |
| | OspA | LYMErix |
| | Anti-Rhesus(Rh) immunoglobulin G | Rhophylac |
| | Enfuvirtide | Fuzeon |
| | Spider silk, e.g., fibrion | QMONOS |

In embodiments, the protein is a multispecific protein, e.g., a bispecific antibody as shown in Table 3.

TABLE 3

Bispecific Formats

| Name (other names, sponsoring organizations) | BsAb format | Targets | Proposed mechanisms of action | Development stages | Diseases (or healthy volunteers) |
|---|---|---|---|---|---|
| Catumaxomab (Removab ®, Fresenius Biotech, Trion Pharma, Neopharm) | BsIgG: Triomab | CD3, EpCAM | Retargeting of T cells to tumor, Fc mediated effector functions | Approved in EU | Malignant ascites in EpCAM positive tumors |
| Ertumaxomab (Neovii Biotech, Fresenius Biotech) | BsIgG: Triomab | CD3, HER2 | Retargeting of T cells to tumor | Phase I/II | Advanced solid tumors |
| Blinatumomab (Blincyto ®, AMG 103, MT 103, MEDI 538, Amgen) | BiTE | CD3, CD19 | Retargeting of T cells to tumor | Approved in USA Phase II and III Phase II Phase I | Precursor B-cell ALL ALL DLBCL NHL |
| REGN1979 (Regeneron) | BsAb | CD3, CD20 | | | |
| Solitomab (AMG 110, MT110, Amgen) | BiTE | CD3, EpCAM | Retargeting of T cells to tumor | Phase I | Solid tumors |
| MEDI 565 (AMG 211, MedImmune, Amgen) | BiTE | CD3, CEA | Retargeting of T cells to tumor | Phase I | Gastrointestinal adenocancinoma |
| RO6958688 (Roche) | BsAb | CD3, CEA | | | |
| BAY2010112 (AMG 212, Bayer; Amgen) | BiTE | CD3, PSMA | Retargeting of T cells to tumor | Phase I | Prostate cancer |
| MGD006 (Macrogenics) | DART | CD3, CD123 | Retargeting of T cells to tumor | Phase I | AML |
| MGD007 (Macrogenics) | DART | CD3, gpA33 | Retargeting of T cells to tumor | Phase I | Colorectal cancer |
| MGD011 (Macrogenics) | DART | CD19, CD3 | | | |
| SCORPION (Emergent Biosolutions, Trubion) | BsAb | CD3, CD19 | Retargeting of T cells to tumor | | |
| AFM11 (Affimed Therapeutics) | TandAb | CD3, CD19 | Retargeting of T cells to tumor | Phase I | NHL and ALL |

TABLE 3-continued

| Bispecific Formats | | | | | |
|---|---|---|---|---|---|
| Name (other names, sponsoring organizations) | BsAb format | Targets | Proposed mechanisms of action | Development stages | Diseases (or healthy volunteers) |
| AFM12 (Affimed Therapeutics) | TandAb | CD19, CD16 | Retargeting of NK cells to tumor cells | | |
| AFM13 (Affimed Therapeutics) | TandAb | CD30, CD16A | Retargeting of NK cells to tumor cells | Phase II | Hodgkin's Lymphoma |
| GD2 (Barbara Ann Karmanos Cancer Institute) | T cells preloaded with BsAb | CD3, GD2 | Retargeting of T cells to tumor | Phase I/II | Neuroblastoma and osteosarcoma |
| pGD2 (Barbara Ann Karmanos Cancer Institute) | T cells preloaded with BsAb | CD3, Her2 | Retargeting of T cells to tumor | Phase II | Metastatic breast cancer |
| EGFRBi-armed autologous activated T cells (Roger Williams Medical Center) | T cells preloaded with BsAb | CD3, EGFR | Autologous activated T cells to EGFR-positive tumor | Phase I | Lung and other solid tumors |
| Anti-EGFR-armed activated T cells (Barbara Ann Karmanos Cancer Institute) | T cells preloaded with BsAb | CD3, EGFR | Autologous activated T-cells to EGFR-positive tumor | Phase I | Colon and pancreatic cancers |
| rM28 (University Hospital Tübingen) | Tandem scFv | CD28, MAPG | Retargeting of T cells to tumor | Phase II | Metastatic melanoma |
| IMCgp100 (Immunocore) | ImmTAC | CD3, peptide MHC | Retargeting of T cells to tumor | Phase I/II | Metastatic melanoma |
| DT2219ARL (NCI, University of Minnesota) | 2 scFv linked to diphtheria toxin | CD19, CD22 | Targeting of protein toxin to tumor | Phase I | B cell leukemia or lymphoma |
| XmAb5871 (Xencor) | BsAb | CD19, CD32b | | | |
| NI-1701 (NovImmune) | BsAb | CD47, CD19 | | | |
| MM-111 (Merrimack) | BsAb | ErbB2, ErbB3 | | | |
| MM-141 (Merrimack) | BsAb | IGF-1R, ErbB3 | | | |
| NA (Merus) | BsAb | HER2, HER3 | | | |
| NA (Merus) | BsAb | CD3, CLEC12A | | | |
| NA (Merus) | BsAb | EGFR, HER3 | | | |
| NA (Merus) | BsAb | PD1, undisclosed | | | |
| NA (Merus) | BsAb | CD3, undisclosed | | | |
| Duligotuzumab (MEHD7945A, Genentech, Roche) | DAF | EGFR, HER3 | Blockade of 2 receptors, ADCC | Phase I and II Phase II | Head and neck cancer Colorectal cancer |
| LY3164530 (Eli Lily) | Not disclosed | EGFR, MET | Blockade of 2 receptors | Phase I | Advanced or metastatic cancer |
| MM-111 (Merrimack Pharmaceuticals) | HSA body | HER2, HER3 | Blockade of 2 receptors | Phase II Phase I | Gastric and esophageal cancers Breast cancer |
| MM-141, (Merrimack Pharmaceuticals) | IgG-scFv | IGF-1R, HER3 | Blockade of 2 receptors | Phase I | Advanced solid tumors |
| RG7221 (RO5520985, Roche) | CrossMab | Ang2, VEGF A | Blockade of 2 proangiogenics | Phase I | Solid tumors |
| RG7716 (Roche) | CrossMab | Ang2, VEGF A | Blockade of 2 proangiogenics | Phase I | Wet AMD |
| OMP-305B83 (OncoMed) | BsAb | DLL4/VEGF | | | |
| TF2 (Immunomedics) | Dock and lock | CEA, HSG | Pretargeting tumor for PET or radioimaging | Phase II | Colorectal, breast and lung cancers |
| ABT-981 (AbbVie) | DVD-Ig | IL-1α, IL-β | Blockade of 2 proinflammatory cytokines | Phase II | Osteoarthritis |

TABLE 3-continued

Bispecific Formats

| Name (other names, sponsoring organizations) | BsAb format | Targets | Proposed mechanisms of action | Development stages | Diseases (or healthy volunteers) |
|---|---|---|---|---|---|
| ABT-122 (AbbVie) | DVD-Ig | TNF, IL-17A | Blockade of 2 proinflammatory cytokines | Phase II | Rheumatoid arthritis |
| COVA322 | IgG-fynomer | TNF, IL17A | Blockade of 2 proinflammatory cytokines | Phase I/II | Plaque psoriasis |
| SAR156597 (Sanofi) | Tetravalent bispecific tandem IgG | IL-13, IL-4 | Blockade of 2 proinflammatory cytokines | Phase I | Idiopathic pulmonary fibrosis |
| GSK2434735 (GSK) | Dual-targeting domain | IL-13, IL-4 | Blockade of 2 proinflammatory cytokines | Phase I | (Healthy volunteers) |
| Ozoralizumab (ATN103, Ablynx) | Nanobody | TNF, HSA | Blockade of proinflammatory cytokine, binds to HSA to increase half-life | Phase II | Rheumatoid arthritis |
| ALX-0761 (Merck Serono, Ablynx) | Nanobody | IL-17A/F, HSA | Blockade of 2 proinflammatory cytokines, binds to HSA to increase half-life | Phase I | (Healthy volunteers) |
| ALX-0061 (AbbVie, Ablynx; | Nanobody | IL-6R, HSA | Blockade of proinflammatory cytokine, binds to HSA to increase half-life | Phase I/II | Rheumatoid arthritis |
| ALX-0141 (Ablynx, Eddingpharm) | Nanobody | RANKL, HSA | Blockade of bone resorption, binds to HSA to increase half-life | Phase I | Postmenopausal bone loss |
| RG6013/ACE910 (Chugai, Roche) | ART-Ig | Factor IXa, factor X | Plasma coagulation | Phase II | Hemophilia |

In embodiments, the product is a polypeptide listed in Table 4.

TABLE 4

| Protein Product | Reference Listed Drug |
|---|---|
| interferon gamma-1b | Actimmune ® |
| alteplase; tissue plasminogen activator | Activase ®/Cathflo ® |
| Recombinant antihemophilic factor | Advate |
| human albumin | Albutein ® |
| Laronidase | Aldurazyme ® |
| Interferon alfa-N3, human leukocyte derived | Alferon N ® |
| human antihemophilic factor | Alphanate ® |
| virus-filtered human coagulation factor IX | AlphaNine ® SD |
| Alefacept; recombinant, dimeric fusion protein LFA3-Ig | Amevive ® |
| Bivalirudin | Angiomax ® |
| darbepoetin alfa | Aranesp ™ |
| Bevacizumab | Avastin ™ |
| interferon beta-1a; recombinant | Avonex ® |
| coagulation factor IX | BeneFix ™ |
| Interferon beta-1b | Betaseron ® |
| Tositumomab | BEXXAR ® |
| antihemophilic factor | Bioclate ™ |
| human growth hormone | BioTropin ™ |
| botulinum toxin type A | BOTOX ® |
| Alemtuzumab | Campath ® |
| acritumomab; technetium-99 labeled | CEA-Scan ® |
| alglucerase; modified form of beta-glucocerebrosidase | Ceredase ® |
| imiglucerase; recombinant form of beta-glucocerebrosidase | Cerezyme ® |
| crotalidae polyvalent immune Fab, ovine | CroFab ™ |
| digoxin immune fab [ovine] | DigiFab ™ |
| Rasburicase | Elitek ® |
| Etanercept | ENBREL ® |
| epoietin alfa | Epogen ® |
| Cetuximab | Erbitux ™ |
| algasidase beta | Fabrazyme ® |
| Urofollitropin | Fertinex ™ |
| follitropin beta | Follistim ™ |
| Teriparatide | FORTEO ® |
| human somatropin | GenoTropin ® |
| Glucagon | GlucaGen ® |
| follitropin alfa | Gonal-F ® |
| antihemophilic factor | Helixate ® |
| Antihemophilic Factor; Factor XIII | HEMOFIL |
| adefovir dipivoxil | Hepsera ™ |
| Trastuzumab | Herceptin ® |
| Insulin | Humalog ® |
| antihemophilic factor/von Willebrand factor complex-human | Humate-P ® |
| Somatotropin | Humatrope ® |
| Adalimumab | HUMIRA ™ |
| human insulin | Humulin ® |
| recombinant human hyaluronidase | Hylenex ™ |
| interferon alfacon-1 | Infergen ® |
| Eptifibatide | Integrilin ™ |
| alpha-interferon | Intron A ® |
| Palifermin | Kepivance |
| Anakinra | Kineret ™ |
| antihemophilic factor | Kogenate ® FS |
| insulin glargine | Lantus ® |
| granulocyte macrophage colony-stimulating factor | Leukine ®/Leukine ® Liquid |
| lutropin alfa for injection | Luveris |
| OspA lipoprotein | LYMErix ™ |

TABLE 4-continued

| Protein Product | Reference Listed Drug |
| --- | --- |
| Ranibizumab | LUCENTIS ® |
| gemtuzumab ozogamicin | Mylotarg ™ |
| Galsulfase | Naglazyme ™ |
| Nesiritide | Natrecor ® |
| Pegfilgrastim | Neulasta ™ |
| Oprelvekin | Neumega ® |
| Filgrastim | Neupogen ® |
| Fanolesomab | NeutroSpec ™ (formerly LeuTech ®) |
| somatropin [rDNA] | Norditropin ®/Norditropin Nordiflex ® |
| Mitoxantrone | Novantrone ® |
| insulin; zinc suspension; | Novolin L ® |
| insulin; isophane suspension | Novolin N ® |
| insulin, regular; | Novolin R ® |
| Insulin | Novolin ® |
| coagulation factor VIIa | NovoSeven ® |
| Somatropin | Nutropin ® |
| immunoglobulin intravenous | Octagam ® |
| PEG-L-asparaginase | Oncaspar ® |
| abatacept, fully human soluable fusion protein | Orencia ™ |
| muromomab-CD3 | Orthoclone OKT3 ® |
| high-molecular weight hyaluronan | Orthovisc ® |
| human chorionic gonadotropin | Ovidrel ® |
| live attenuated *Bacillus* Calmette-Guerin | Pacis ® |
| peginterferon alfa-2a | Pegasys ® |
| pegylated version of interferon alfa-2b | PEG-Intron ™ |
| Abarelix (injectable suspension); gonadotropin-releasing hormone Antagonist | Plenaxis ™ |
| epoietin alfa | Procrit ® |
| Aldesleukin | Proleukin, IL-2 ® |
| Somatrem | Protropin ® |
| dornase alfa | Pulmozyme ® |
| Efalizumab; selective, reversible T-cell blocker | RAPTIVA ™ |
| combination of ribavirin and alpha interferon | Rebetron ™ |
| Interferon beta 1a | Rebif ® |
| antihemophilic factor | Recombinate ® rAHF/ |
| antihemophilic factor | ReFacto ® |
| Lepirudin | Refludan ® |
| Infliximab | REMICADE ® |
| Abciximab | ReoPro ™ |
| Reteplase | Retavase ™ |
| Rituxima | Rituxan ™ |
| interferon alfa-2$^a$ | Roferon-A ® |
| Somatropin | Saizen ® |
| synthetic porcine secretin | SecreFlo ™ |
| Basiliximab | Simulect ® |
| Eculizumab | SOLIRIS (R) |
| Pegvisomant | SOMAVERT ® |
| Palivizumab; recombinantly produced, humanized mAb | Synagis ™ |
| thyrotropin alfa | Thyrogen ® |
| Tenecteplase | TNKase ™ |
| Natalizumab | TYSABRI ® |
| human immune globulin intravenous 5% and 10% solutions | Venoglobulin-S ® |
| interferon alfa-n1, lymphoblastoid | Wellferon ® |
| drotrecogin alfa | Xigris ™ |
| Omalizumab; recombinant DNA-derived humanized monoclonal antibody targeting immunoglobulin-E | Xolair ® |
| Daclizumab | Zenapax ® |
| ibritumomab tiuxetan | Zevalin ™ |
| Somatotropin | Zorbtive ™ (Serostim ®) |

In some embodiments, the polypeptide is an antigen expressed by a cancer cell. In some embodiments the recombinant or therapeutic polypeptide is a tumor-associated antigen or a tumor-specific antigen. In some embodiments, the recombinant or therapeutic polypeptide is selected from HER2, CD20, 9-O-acetyl-GD3, βhCG, A33 antigen, CA19-9 marker, CA-125 marker, calreticulin, carboanhydrase IX (MN/CA IX), CCR5, CCR8, CD19, CD22, CD25, CD27, CD30, CD33, CD38, CD44v6, CD63, CD70, CC123, CD138, carcinoma embryonic antigen (CEA; CD66e), desmoglein 4, E-cadherin neoepitope, endosialin, ephrin A2 (EphA2), epidermal growth factor receptor (EGFR), epithelial cell adhesion molecule (EpCAM), ErbB2, fetal acetylcholine receptor, fibroblast activation antigen (FAP), fucosyl GM1, GD2, GD3, GM2, ganglioside GD3, Globo H, glycoprotein 100, HER2/neu, HER3, HER4, insulin-like growth factor receptor 1, Lewis-Y, LG, Ly-6, melanoma-specific chondroitin-sulfate proteoglycan (MCSCP), mesothelin, MUC1, MUC2, MUC3, MUC4, MUC5$_{AC}$, MUC5$_B$, MUC7, MUC16, Mullerian inhibitory substance (MIS) receptor type II, plasma cell antigen, poly SA, PSCA, PSMA, sonic hedgehog (SHH), SAS, STEAP, sTn antigen, TNF-alpha precursor, and combinations thereof.

In some embodiments, the polypeptide is an activating receptor and is selected from 2B4 (CD244), α$_4$β$_1$ integrin, β$_2$ integrins, CD2, CD16, CD27, CD38, CD96, CD1OO, CD160, CD137, CEACAM1 (CD66), CRTAM, CS1 (CD319), DNAM-1 (CD226), GITR (TNFRSF18), activating forms of KIR, NKG2C, NKG2D, NKG2E, one or more natural cytotoxicity receptors, NTB-A, PEN-5, and combinations thereof, optionally wherein the β$_2$ integrins comprise CD11a-CD 18, CD11 b-CD 18, or CD11c-CD 18, optionally wherein the activating forms of KIR comprise KIR2DS1, KIR2DS4, or KIR-S, and optionally wherein the natural cytotoxicity receptors comprise NKp30, NKp44, NKp46, or NKp80.

In some embodiments, the polypeptide is an inhibitory receptor and is selected from KIR, ILT2/LIR-1/CD85j, inhibitory forms of KIR, KLRG1, LAIR-1, NKG2A, NKR-P1A, Siglec-3, Siglec-7, Siglec-9, and combinations thereof, optionally wherein the inhibitory forms of KIR comprise KIR2DL1, KIR2DL2, KIR2DL3, KIR3DL1, KIR3DL2, or KIR-L.

In some embodiments, the polypeptide is an activating receptor and is selected from CD3, CD2 (LFA2, OX34), CD5, CD27 (TNFRSF7), CD28, CD30 (TNFRSF8), CD40L, CD84 (SLAMF5), CD137 (4-1BB), CD226, CD229 (Ly9, SLAMF3), CD244 (2B4, SLAMF4), CD319 (CRACC, BLAME), CD352 (Ly108, NTBA, SLAMF6), CRTAM (CD355), DR3 (TNFRSF25), GITR (CD357), HVEM (CD270), ICOS, LIGHT, LTβR (TNFRSF3), OX40 (CD134), NKG2D, SLAM (CD150, SLAMF1), TCRα, TCRβ, TCRδγ, TIM1 (HAVCR, KIM1), and combinations thereof.

In some embodiments, the polypeptide is an inhibitory receptor and is selected from PD-1 (CD279), 2B4 (CD244, SLAMF4), B71 (CD80), B7H1 (CD274, PD-L1), BTLA (CD272), CD160 (BY55, NK28), CD352 (Ly108, NTBA, SLAMF6), CD358 (DR6), CTLA-4 (CD152), LAG3, LAIR1, PD-1H (VISTA), TIGIT (VSIG9, VSTM3), TIM2 (TIMD2), TIM3 (HAVCR2, KIM3), and combinations thereof.

Other exemplary proteins include, but are not limited to any protein described in Tables 1-10 of Leader et al., "Protein therapeutics: a summary and pharmacological classification", Nature Reviews Drug Discovery, 2008, 7:21-39 (incorporated herein by reference); or any conjugate, variant, analog, or functional fragment of the recombinant polypeptides described herein.

Other recombinant protein products include non-antibody scaffolds or alternative protein scaffolds, such as, but not limited to: DARPins, affibodies and adnectins. Such non-antibody scaffolds or alternative protein scaffolds can be engineered to recognize or bind to one or two, or more, e.g., 1, 2, 3, 4, or 5 or more, different targets or antigens.

In one embodiment, the vector comprising a nucleic acid sequence encoding a product, e.g., a polypeptide, e.g, a recombinant polypeptide, described herein further comprises a nucleic acid sequence that encodes a selection marker. In one embodiment, the selectable marker comprises glutamine synthetase (GS); dihydrofolate reductase (DHFR) e.g., an enzyme which confers resistance to methotrexate (MTX); proline, or an antibiotic marker, e.g., an enzyme that confers resistance to an antibiotic such as: hygromycin, neomycin (G418), zeocin, puromycin, or blasticidin. In another embodiment, the selection marker comprises or is compatible with the Selexis selection system (e.g., SUREtechnology Platform™ and Selexis Genetic Elements™ commercially available from Selexis SA) or the Catalant selection system.

In one embodiment, the vector comprising a nucleic acid sequence encoding a recombinant product described herein comprises a selection marker that is useful in identifying a cell or cells comprise the nucleic acid encoding a recombinant product described herein. In another embodiment, the selection marker is useful in identifying a cell or cells that comprise the integration of the nucleic acid sequence encoding the recombinant product into the genome, as described herein. The identification of a cell or cells that have integrated the nucleic acid sequence encoding the recombinant protein can be useful for the selection and engineering of a cell or cell line that stably expresses the product.

In one embodiment, the product differs from a polypeptide from Tables 1-4 at no more than 1, 2, 3, 4, 5, 10, 15, 20, 25, 30, 35, 40, 45, or 50 amino acid residues. In another embodiment, the product differs from a polypeptide from Table 2 or 3 at no more than 1%, 2%, 3%, 4%, 5%, 6%, 7%, 8%, 9%, 10%, or 15% of its amino acid residues. Methods for determining percent identity are discussed above.

Other recombinant products include non-antibody scaffolds or alternative protein scaffolds, such as, but not limited to: DARPins, affibodies and adnectins.

Other exemplary therapeutic or diagnostic proteins include, but are not limited to any protein described in Tables 1-10 of Leader et al., "Protein therapeutics: a summary and pharmacological classification", Nature Reviews Drug Discovery, 2008, 7:21-39 and as described in Walsh, "Biopharmaceutical benchmarks 2014", Nature Biotechnology, 2014, 32:992-1000 (each incorporated herein by reference); or any conjugate, variant, analog, or functional fragment of the recombinant polypeptides described herein.

Reduction and Oxidation

Reduction and oxidation reactions (redox reactions), in which electrons are donated or removed from a compound, are common in biological systems. The tendency to give up electrons or gain electrons in a redox reaction under a set of conditions can be described by the redox potential of a compound. Redox potential ($\Delta E$) is measured in volts (V) or millivolts (mV). Redox potential can be calculated for individual compounds, e.g., a protein, in which case the redox potential describes the affinity of the compound for electrons; the more positive the redox potential, the greater the tendency to gain electrons, the more negative the redox potential, the greater the tendency to give up electrons. In addition to compounds, solutions, organelles, and cells can also have their tendencies to gain or lose electrons represented as a redox potential.

Cells use several systems to regulate their redox potential. The thioredoxin system in humans comprises two proteins, Trx1 and Trx2. The Trx proteins have low redox potential and reduce protein disulfide bonds; this reduction reaction is catalyzed by thioredoxin reductase (TrxR) using electrons from NADPH.

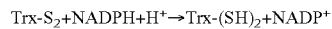
Trx-S$_2$+NADPH+H$^+$→Trx-(SH)$_2$+NADP$^+$

Protein-S$_2$+Trx-(SH)$_2$→protein-(SH)$_2$+Trx-S$_2$ The glutaredoxin system consists of glutaredoxin, glutathione, and NADPH dependent glutathione reductase. The glutaredoxin system reduces protein disulphide bonds using glutathione, which is returned to its reduced state with the consumption of NADPH. Glutaredoxin reduces protein thiol groups by either a dithiol mechanism,

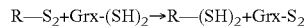
R—S$_2$+Grx-(SH)$_2$→R—(SH)$_2$+Grx-S$_2$

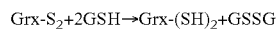
Grx-S$_2$+2GSH→Grx-(SH)$_2$+GSSG or a monothiol mechanism,

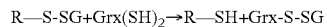
R—S-SG+Grx(SH)$_2$→R—SH+Grx-S-SG

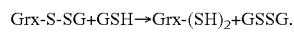
Grx-S-SG+GSH→Grx-(SH)$_2$+GSSG.

For further information on redox reactions, potentials, and methods of regulating or control redox reactions/potentials, see, e.g., Holmgren et al. Biochem Soc Trans. 2005 December; 33 (Pt 6):1375-7; Nordberg and Amer. Free Radic Biol Med. 2001 Dec. 1; 31(11):1287-312; Ghezzi P. Biochem Soc Trans. 2005 December; 33(Pt 6):1378-81; Ivarsson et al. Diabetes. 2005 July; 54(7):2132-42; Sen, C K. Biochem Pharmacol 55 (11), 1747-1758. 1998 Jun. 1; and May et al. J Biol Chem. 1997 Sep. 5; 272(36):22607-10; Molteni, S. N., et al. (2004). "Glutathione limits Ero1-dependent oxidation in the endoplasmic reticulum." Journal of Biological Chemistry 279(31): 32667-32673; Kojer, K. and J. Riemer (2014). "Balancing oxidative protein folding: The influences of reducing pathways on disulfide bond formation." Biochimica et Biophysica Acta—Proteins and Proteomics 1844(8): 1383-1390; Hanschmann, E.-M., et al. (2013). "Thioredoxins, Glutaredoxins, and Peroxiredoxins—Molecular Mechanisms and Health Significance: from Cofactors to Antioxidants to Redox Signaling." Antioxidants & Redox Signaling 19(13): 1539-1605; Chakravarthi, S., et al. (2006). "The role of glutathione in disulphide bond formation and endoplasmic-reticulum-generated oxidative stress." EMBO Reports 7(3): 271-275; Flohé, L. (2013). "The fairytale of the GSSG/GSH redox potential." Biochimica et Biophysica Acta—General Subjects 1830(5): 3139-3142; and Bánhegyi, G., et al. (2007). "Stress on redox." FEBS Letters 581(19): 3634-3640, each of which is hereby incorporated by reference in its entirety.

Redox potential can be adjusted independent of the redox regulating systems employed by cells. For example, by adjusting the level of oxygen in a solution, the redox potential of a compound, e.g., a product, e.g., a protein, can be adjusted. Increasing the level of oxygen in a solution, e.g., making the solution favor oxidation, increases the redox potential of a product, e.g., a protein. Increasing the redox potential of a product, e.g., a protein, can decrease the likelihood that the disulfide bonds of the product, e.g., the protein, will be reduced relative to the product, e.g., protein, at a lower redox potential.

Production Applications

The methods of preparation of products, e.g., product variants, disclosed herein can be used to produce a variety of products, evaluate various cell lines, or to evaluate the production of various cell lines for use in a bioreactor or processing vessel or tank, or, more generally with any feed source. The devices, facilities and methods described herein are suitable for culturing any desired cell line including prokaryotic and/or eukaryotic cell lines. Further, in embodiments, the devices, facilities and methods are suitable for culturing suspension cells or anchorage-dependent (adherent) cells and are suitable for production operations configured for production of pharmaceutical and biopharmaceutical products—such as polypeptide products or cells and/or viruses such as those used in cellular and/or viral therapies.

As mentioned, in embodiments, devices, facilities and methods allow for the production of eukaryotic cells, e.g., mammalian cells or lower eukaryotic cells such as for example yeast cells or filamentous fungi cells, or prokaryotic cells such as Gram-positive or Gram-negative cells and/or products of the eukaryotic or prokaryotic cells, e.g., proteins, peptides, antibiotics, amino acids, synthesised by the eukaryotic cells in a large-scale manner. Unless stated otherwise herein, the devices, facilities, and methods can include any desired volume or production capacity including but not limited to bench-scale, pilot-scale, and full production scale capacities.

Moreover and unless stated otherwise herein, the devices, facilities, and methods can include any suitable reactor(s) including but not limited to stirred tank, airlift, fiber, microfiber, hollow fiber, ceramic matrix, fluidized bed, fixed bed, and/or spouted bed bioreactors. As used herein, "reactor" or "bioreactor" can include a fermentor or fermentation unit, or any other reaction vessel and the terms "reactor" and "bioreactor" are used interchangeably with "fermentor." For example, in some aspects, a bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and CO2 levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reactors within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316L or any other suitable stainless steel) and Inconel, plastics, and/or glass. In some embodiments, suitable reactors can be round, e.g., cylindrical. In some embodiments, suitable reactors can be square, e.g., rectangular. Square reactors may in some cases provide benefits over round reactors such as ease of use (e.g., loading and setup by skilled persons), greater mixing and homogeneity of reactor contents, and lower floor footprint.

In embodiments and unless stated otherwise herein, the devices, facilities, and methods described herein for use with methods of making a preparation can also include any suitable unit operation and/or equipment not otherwise mentioned, such as operations and/or equipment for separation, purification, and isolation of such products. Any suitable facility and environment can be used, such as traditional stick-built facilities, modular, mobile and temporary facilities, or any other suitable construction, facility, and/or layout. For example, in some embodiments modular cleanrooms can be used. Additionally and unless otherwise stated, the devices, systems, and methods described herein can be housed and/or performed in a single location or facility or alternatively be housed and/or performed at separate or multiple locations and/or facilities.

By way of non-limiting examples and without limitation, U.S. Publication Nos. 2013/0280797; 2012/0077429; 2011/0280797; 2009/0305626; and U.S. Pat. Nos. 8,298,054; 7,629,167; and 5,656,491, which are hereby incorporated by reference in their entirety, describe example facilities, equipment, and/or systems that may be suitable.

Bioreactor Setup and Conditions

In one aspect, a bioreactor of the disclosure or a bioreactor utilized by a method of the disclosure is a single-use bioreactor.

The single-use bioreactor may include a bioprocess container, a shell, at least one agitator, at least one sparger, at least one gas filter inlet port for the sparger(s) and headspace overlay, at least one fill port, at least one harvest port, at least one sample port, and at least one probe.

In one embodiment, the present disclosure is directed to a bioreactor comprising a bioprocess container. The bioprocess container is made from a liquid impermeable and flexible shape-conforming material. For instance, the bioprocess container can be made from a flexible film, such as a multi-layer film. In one embodiment, for instance, the film is comprised of a polyethylene polymer, such as a low density polyethylene that has been modified to form a hydrophilic surface. The hydrophilic surface is for contact with cell cultures within the bioreactor and improves wettability. In one embodiment, the polyethylene polymer is modified by being subjected to irradiation, photo or plasma induction, or oxidation.

The bioprocess container can have a top, a bottom, and at least one side wall therebetween. The bioprocess chamber can define a hollow enclosure for receiving a culture media. The hollow enclosure can have any suitable volume, such as 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters.

The bioreactor can include at least one inlet port for feeding materials into the hollow enclosure of the bioprocess container. A mixing device comprising a rotatable shaft coupled to at least one agitator can extend into the hollow enclosure of the bioprocess container. In one embodiment, the rotatable shaft can be collapsible. For instance, the rotatable shaft can include at least one impeller made from a hydrophilic polymer material that is collapsible or foldable towards the rotatable shaft.

The bioreactor can also include at least one baffle configured to extend adjacent to the side wall of the bioprocess container in a longitudinal direction. The baffle can have a shape that extends radially inward from the side wall an amount sufficient to affect fluid flow in the hollow enclosure during mixing of a culture media by the mixing device. The baffle can be collapsible and/or foldable. In one embodiment, for instance, the baffle can define an inflatable fluid bladder making the baffle capable of being inflated and deflated. The baffle can be integral with the bioprocess container meaning that the baffle is formed into the flexible shape-forming material. Alternatively, the baffle can be separate from the bioprocess container. The baffle can be configured to be placed inside the hollow enclosure or can be placed outside the hollow enclosure. When placed outside the hollow enclosure, the side wall of the bioprocess container conforms around the shape of the baffle. For example, in one embodiment, the baffle can be removably attached to an outer metallic shell. The bioprocess container can be placed in the metallic shell for conforming around the shape of the baffle. The bioreactor, in one embodiment, can include from about two to about six baffles that are spaced around a circumference of the hollow enclosure of the bioprocess container.

In one embodiment, the bioprocess container has a diameter and the one or more baffles extend radially inward a distance of from about 3% to about 20%, such as from about 5% to about 15% of the diameter of the bioprocess container.

The bioreactor can further include at least one sparger. The sparger, for instance, may comprise a ballast sparger that comprises a gas tube having a longitudinal portion and a lateral portion. The longitudinal portion can extend vertically into the hollow enclosure of the bioprocess container. The lateral portion, on the other hand, can be located at an end of the longitudinal portion below the agitator. The lateral portion can define a plurality of holes for releasing a gas into a culture media contained within the bioprocess container. In one embodiment, the plurality of holes are drilled. The lateral portion can have any suitable shape. In one embodiment, the lateral portion can be configured to engage the rotatable shaft of the mixing device for stabilizing the shaft. The rotatable shaft may extend through the lateral portion or can be housed within a shaft receiving member formed into the lateral portion.

In one embodiment, the bioreactor includes a first subsurface sparger and a second supersurface sparger. The plurality of holes in the subsurface sparger can be larger or smaller than the plurality of holes on the supersurface sparger. In one embodiment, the plurality of holes are drilled.

In one embodiment, the bioreactor can include at least one feed line that extends into the hollow enclosure for feeding fluids into the bioprocess container. The feed line can include a subsurface fluid outlet positioned adjacent the agitator. The fluid outlet can be associated with a fluid control device that only permits fluid to flow out of the fluid outlet and prevents fluid flow in an opposite direction. For instance, the fluid control device may comprise a one-way valve.

In another embodiment, the bioreactor can include a feed line positioned at the top of the bioprocess container. The feed line can include a supersurface fluid discharge positioned above a volume of culture media residing in the bioprocess container. The supersurface fluid discharge can be located such that a fluid flowing through the fluid discharge makes direct contact with a culture media contained within the bioprocess container. In one embodiment, the agitator can form a circumference when rotated and the supersurface fluid discharge of the feed line can be positioned above the circumference of the agitator such that fluids flowing through the fluid discharge contact the culture media within the circumference.

The bioreactor can be placed in operative association with a load cell for indicating a mass of a culture media contained within the hollow enclosure. The bottom of the bioprocess container can have a dome-shape for facilitating drainage. For instance, the bioprocess container can include a drain line located at the bottom of the bioprocess container. A fluid collecting device can be positioned inbetween the hollow enclosure of the bioprocess container and the drain line. The fluid collecting device can have a shape configured to induce a vortex flow of fluids from the bioprocess container into the drain line. In one embodiment, the drain line has a cross-sectional area that is proportional to the volume of the hollow enclosure. For example, for exemplary purposes, the drain line can have a cross-sectional area of from about 0.3 $mm^2$ to about 0.7 $mm^2$, such as from about 0.4 $mm^2$ to about 0.6 $mm^2$ per liter of volume of the hollow enclosure.

In one embodiment, the bioprocess container can include a plurality of ports for connecting to a plurality of supply lines for feeding fluids to the bioprocess container. Each port and corresponding supply line can include matching indicators for assisting a user in connecting the supply lines to the respective ports. The matching indicators, for instance, may comprise color such that each port and corresponding supply line are color-coded. Matching indicia can also be applied to feed lines and any corresponding ports and to spargers and any corresponding connectors.

In one embodiment, the bioprocess container can include ports that comprise universal connectors. The ports can have a first end and a second end. The first end can be for forming a reconnectable attachment to a respective supply line. Each supply line can include a fluid filter positioned upstream from the corresponding ports.

The present disclosure is also directed to a bioreactor system. The bioreactor system can include a bioprocess container made from a liquid impermeable and flexible shape-conforming material. The bioprocess container can have a top, a bottom, and at least one side wall therebetween. The bioprocess chamber can define a hollow enclosure for receiving a culture media. The bioprocess container can also include a plurality of inlet ports for feeding materials into the hollow enclosure. A drain line can be positioned at the bottom of the bioprocess container for draining fluids. A mixing device can extend into the hollow enclosure of the bioprocess container and can comprise a rotatable shaft coupled to at least one agitator.

The bioreactor system can further include at least one sensor in operative association with the bioprocess container for monitoring at least one parameter within the hollow enclosure. The at least one sensor can comprise a pH sensor, a dissolved carbon dioxide sensor, a dissolved oxygen sensor, redox sensor, a load cell, a temperature sensor, or a tachometer. A controller can be placed in communication with the at least one sensor. The controller can be configured to receive information from the at least one sensor and, based on the information, to control a fluid supply for varying a flow rate of a fluid from the fluid supply into the hollow enclosure of the bioprocess container for maintaining the at least one parameter of a culture media contained within the hollow enclosure within preset limits.

For example, in one embodiment, the bioreactor system can include a carbon dioxide gas supply in fluid communication with the bioprocess container and a liquid alkali supply also in fluid communication with the bioprocess container. The at least one sensor can comprise a pH sensor and the controller can be configured to regulate pH levels of a culture media within the preset limits by adding amounts of carbon dioxide gas from the carbon dioxide gas supply for selectively lowering the pH or by adding amounts of an alkali from the liquid alkali supply for selectively increasing the pH. In one embodiment, the system can include a first pH sensor and a second pH sensor both in communication with the controller.

In yet another embodiment, the bioreactor system can include an oxygen gas supply and the at least one sensor can comprise a dissolved oxygen sensor. The controller can regulate dissolved oxygen levels within a culture media within preset limits by periodically adding amounts of oxygen gas from the oxygen gas supply to a culture media based on information received from the dissolved oxygen sensor.

In still another embodiment, the bioreactor system can include a carbon dioxide gas supply and wherein the at least one sensor comprises a dissolved carbon dioxide sensor. The controller can be configured to regulate dissolved carbon dioxide levels within a culture media within preset limits by periodically adding amounts of carbon dioxide gas from the carbon dioxide gas supply to a culture media based upon information received from the dissolved carbon dioxide sensor.

In still another embodiment, the bioreactor system can include a thermal jacket surrounding the bioprocess container. The thermal jacket can be in fluid communication with at least one of a heated fluid or a chilled fluid. The bioreactor system can further include a temperature sensor for sensing a temperature of a culture media contained within the bioprocess container. The temperature sensor can be in communication with the controller. The controller can be configured to receive information from the temperature sensor, and, based on the information, control flow of a fluid into the thermal jacket for increasing or decreasing the temperature of a culture media contained in the bioprocess container for maintaining a culture media within preset temperature limits.

In another embodiment, the bioreactor system can further include a tachometer for monitoring a rotational speed of the rotatable shaft coupled to the at least one agitator. The tachometer can be in communication with the controller. The controller can be in communication with a motor that rotates the shaft. The controller can be configured to control the motor in a manner that rotates the shaft at a predetermined speed based upon information received from the tachometer.

The controller may comprise one or more microprocessors.

In one embodiment, the controller can be configured to receive information from multiple sensors in order to control multiple parameters within the bioreactor.

In one embodiment, one or more of the sensors described above can be integrated into the bioprocess container and can be disposable with the bioprocess container.

The present disclosure is also directed to a bioreactor comprising a bioprocess container made from a liquid impermeable and flexible shape-conforming material. The bioprocess container can have a top, a bottom, and at least one side wall therebetween. The bioprocess chamber can define a hollow enclosure for receiving a culture media. At least one feed line can extend into the hollow enclosure for feeding a fluid into the bioprocess container.

In one embodiment, the feed line includes a subsurface fluid outlet positioned adjacent to an agitator. The fluid outlet can be associated with a fluid control device that only permits fluid to flow out of the fluid outlet and prevents fluid flow in an opposite direction.

In an alternative embodiment, the feed line can comprise a supersurface fluid discharge positioned above a volume of a culture media residing in the bioprocess container. The supersurface fluid discharge can be located such that a fluid flowing through the fluid discharge makes direct contact with a culture media contained within the bioprocess container without contacting the side wall.

In one embodiment, the bioreactor can include a first feed line that includes the subsurface fluid outlet and a second feed line including the supersurface fluid discharge. In one embodiment, the bioreactor can contain from about one to about five, such as from about two to about three feed lines that have a supersurface fluid discharge.

In yet another embodiment, the present disclosure is directed to a method for producing a single use bioreactor. The method includes the steps of constructing a bioprocess container from a liquid impermeable and flexible shape-conforming material. The bioprocess container having a top, a bottom, and at least one side wall therebetween. The bioprocess chamber defines a hollow enclosure for receiving a culture media. The hollow enclosure can have a volume of from about of 1-250 milliliters, 250 milliliters to 50 liters, 50 to 800 liters, or 800-200,000 liters. The bioprocess container includes a plurality of inlet ports for feeding materials into the hollow enclosure of the bioprocess container. Each inlet port has a diameter.

A mixing device is inserted into the hollow enclosure. The mixing device comprises a rotatable shaft coupled to at least one agitator. At least one sparger is also inserted into the hollow enclosure of the bioprocess container. The sparger comprises a gas tube that has a longitudinal portion and a lateral portion. The longitudinal portion extends vertically into the hollow enclosure. The lateral portion is located at an end of the longitudinal portion below the agitator. The lateral portion defines a plurality of holes for releasing a gas into a culture media contained within the bioprocess container. The plurality of holes have a diameter.

A drain line is connected to the bottom of the bioprocess container. The drain line has a cross-sectional area.

In accordance with the present disclosure, the diameter of the inlet ports, the diameter of the plurality of holes on the sparger, and the cross-sectional area of the drain line are proportional to the volume of the hollow enclosure. The drain line, for instance, can have a cross-sectional area of from about 0.3 mm$^2$ to about 0.7 mm$^2$ per liter of volume of the hollow enclosure.

The present disclosure is also directed to a bioreactor comprising a bioprocess container made from a liquid impermeable and flexible shape-conforming material. The bioprocess chamber can define a hollow enclosure for receiving a culture media and can include at least one inlet port. A mixing device comprising a rotatable shaft coupled to a plurality of agitators can extend into the hollow enclosure of the bioprocess container.

In accordance with the present disclosure, the bioreactor can further include a [ ]cell retention chamber in fluid communication with the hollow enclosure of the bioprocess container. A filtrate outlet can be placed in fluid communication with the cell retention chamber. The filtrate outlet includes a biofilter that is permeable to liquids but impermeable to biological materials contained in a culture media. The filtrate outlet is for removing liquids from the cell retention chamber continuously or periodically. A flow regulator is configured to alternate flow of a culture media between the hollow enclosure of the bioprocess container and the cell retention chamber for carrying out a perfusion process.

The flow regulator, for instance, can be in communication with a pressurized gas source and a vacuum source. The flow regulator can be configured to alternatively apply a vacuum or a gas pressure to a fluid contained in the cell retention chamber for recycling fluids back and forth between the hollow enclosure of the bioprocess container and the cell retention chamber.

In one embodiment, the flow regulator can include a reciprocating diaphragm that alternates between applying pressure and applying a suction force to the fluid contained in the cell retention chamber.

The present disclosure is also directed to a bioreactor comprising a bioprocess container made from a liquid impermeable and flexible shape-conforming material. The bioprocess container defines a hollow enclosure for receiving a culture media. A mixing device comprising a rotatable shaft coupled to at least one agitator can extend into the hollow enclosure of the bioprocess container. In accordance with the present disclosure, the agitator can be collapsible onto the rotating shaft. For instance, the agitator can comprise an impeller comprising at least one blade element. The blade element can be foldable towards the rotatable shaft. In one embodiment, the rotatable shaft is coupled to a first impeller and a second impeller and both impellers can include at least one blade element that is foldable. A retaining ring can be positioned on the shaft. The retaining ring can include an agitator engaging position and an agitator disengaging position for holding the agitator in an upright position during mixing or in a collapsed and folded position respectively.

In one embodiment, the rotatable shaft comprises a metallic reinforcing rod surrounded by a shaft sleeve. The metallic reinforcing rod, which can be made from stainless steel, can be made from multiple pieces that are attached together. The top of the reinforcing rod can include a magnetic member for magnetically engaging a motor. The shaft sleeve can be comprised of a polymeric material. The agitator on the shaft can also be made from a polymeric material, such as a hydrophilic polymer. For example, the shaft sleeve and the agitator can comprise a polyethylene polymer that has been modified by being subjected to irradiation, photo or plasma induction, or oxidation.

In one embodiment, a single use bioreactor system according to the instant disclosure comprises: a single use cell culture bioprocess container ("SUB"), a reusable shell in which the SUB is held during operation, and a controller that controls the operation of the SUB and associated sub-systems and processes. Associated sub-systems include an agitation system, a baffle system, a sparger system, a feeding system, a harvesting system, a monitoring system, control system(s), and a fill system.

In one embodiment, each of cell culture contacting and process fluid contacting surface of the SUB are preferably animal derived component free.

According to one aspect of the disclosure, a single-use bioreactor is provided. The single-use bioreactor may include a bioprocess container, a shell, at least one agitator, at least one sparger, at least one gas filter inlet port for the sparger(s) and headspace overlay, at least one fill port, at least one harvest port, at least one sample port, and at least one probe.

A single use bioreactor of the disclosure may also be used with a single use bioreactor (SUB) system. The system may include a flexible bioreactor bioprocess container that is for single use and disposable, a SUB shell configured to hold the flexible bioreactor bioprocess container, an agitator, a sparger, a plurality of ports, and at least one controller configured to control a plurality of parameters associated with the SUB system such that the SUB system produces biomaterial corresponding to biomaterial capable of being produced in a similarly sized stainless steel bioreactor.

In accordance with the present disclosure, the rotatable shaft can be coupled to a top impeller and to a bottom impeller. Both the top impeller and the bottom impeller can be made from a polymer material. For instance, in one embodiment, the impellers may be 3-D printed. The top impeller and the bottom impeller can both define a hydrophilic surface. For instance, the polymer material used to form the impellers can comprise a hydrophilic polymer or can comprise a polymer that has been surface modified so as to render the surface hydrophilic.

In one embodiment, for instance, the top impeller and bottom impeller are made from a polyolefin polymer, such as polyethylene or polypropylene. In one embodiment, low density polyethylene can be used. The low density polyethylene can be modified by being subjected to irradiation, photo or plasma induction, or oxidation to form a hydrophilic surface.

The top impeller can comprise a hydrofoil impeller. The bottom impeller, on the other hand, can comprise a four pitched-bladed high solidity impeller. The impeller to tank diameter ratio can be from about 0.35 to about 0.55, such as from about 0.44 to about 0.46. The top impeller and the bottom impeller can have power numbers ($N_p$) of from about 0.1 to about 0.9 and can have flow numbers ($N_q$) of from about 0.4 to about 0.9.

In some embodiments, a bioreactor of the disclosure is a bioreactor as described in U.S. Pat. No. 9,670,446, the content of which is hereby incorporated by reference in its entirety. In some embodiments, a bioreactor of the disclosure comprises a part or feature of a bioreactor described in U.S. Pat. No. 9,670,446.

In one embodiment, a bioreactor can be operably coupled to a harvest vessel, e.g., harvest vessel. The harvest vessel may comprise a means to mix culture and gas (e.g., to aerate culture), e.g., to ensure adequate oxygenation of culture. In an embodiment, the harvest vessel comprises a supernatant having been deposited in the harvest vessel, e.g., from the bioreactor), and a head space comprising gas, e.g., air, oxygen, or a mixture of air and oxygen. In an embodiment, the harvest vessel uses surface aeration to oxygenate culture supernatant with the headspace gas e.g. air or oxygen or air and oxygen gas mixture. Surface aeration involves cascading or flowing supernatant from the J-tube inlet port down the harvest vessel wall and from the supernatant liquid surface in contact with the headspace In some embodiments, travel or cascade results in an increase in oxygenation level of the culture.

The harvest vessel may include at least one mixer, at least one gas filter inlet ports for the headspace overlay, at least one fill port with an internal J-tube directed towards the vessel wall, at least one harvest port, at least one sample port, at least one temperature probe, at least one redox probe, at least one DOT probe, and at least one pH probe, at least one temperature control, at least one gas flow, e.g., at least one air flow control and at least one O2 flow control. In one embodiment, the harvest vessel comprises a head space gas mixture of air/$O_2$ that maintains a DOT in a range greater than 40% air saturation to less than or equal to 500% air saturation In an embodiment, a bioreactor or harvest vessel comprises a redox probe, e.g., an in-line redox probe, e.g., a Mettler Toledo in-line redox probe.

In some embodiments, a method comprises a bioreactor or harvest vessel is capable of providing, e.g., adding, or regulating, e.g., increasing or decreasing activity/abundance of, components of the thioredoxin or glutathione/glutaredoxin systems to provide or maintain a redox potential in a culture or cells of a culture or culture supernatant. The thioredoxin and glutathione/glutaredoxin systems and their components are known in the art. See, e.g., Holmgren et al. Biochem Soc Trans. 2005 December; 33(Pt 6):1375-7; Nordberg and Amer. Free Radic Biol Med. 2001 Dec. 1; 31(11):1287-312; Ghezzi P. Biochem Soc Trans. 2005 December; 33(Pt 6):1378-81; Ivarsson et al. Diabetes. 2005 July; 54(7):2132-42; Sen, C K. Biochem Pharmacol 55 (11), 1747-1758. 1998 Jun. 1; and May et al. J Biol Chem. 1997 Sep. 5; 272(36):22607-10, the contents of which are hereby incorporated by reference in their entirety.

In an embodiment, a method comprises or a bioreactor or harvest vessel is capable of providing, e.g., adding, or regulating, e.g., increasing or decreasing activity/abundance of, GILT (gamma-interferon-inducible lysosomal thiol reductase). See, e.g., Rausch and Hastings. Mol Immunol. 2015 December; 68(2 Pt A):124-8. doi: 10.1016/j.molimm.2015.06.008. Epub 2015 Jun. 23; and Hastings and Cresswell. Antioxid Redox Signal. 2011 Aug. 1; 15(3): 657-668, the contents of which are hereby incorporated by reference in their entirety. In an embodiment, a method comprises or a bioreactor or harvest vessel is capable of providing, e.g., adding, ascorbic acid, dehydroascorbic acid, or an ascorbic acid or dehydroascorbic acid modifying component to the growth culture. The redox potential regulating properties of ascorbic acid and dehydroascorbic acid are known in the art. See, e.g., Winkler et al. Free Radic Biol Med. 1994 October; 17(4):333-49, which is hereby incorporated by reference in its entirety.

In an embodiment, a method comprises or a bioreactor is capable of providing intracellular agents, e.g., adding redox potential-indicating labels, e.g., redox-sensitive dyes or molecular probes, to the production culture. Such redox potential-indicating labels may be useful for monitoring the redox potential of the culture or cells within the culture. Redox potential-indicating labels include, but are not limited to: 2,2'-bipyridine (Ru complex), Nitrophenanthroline (Fe complex), N-Phenylanthranilic acid, 1,10-Phenanthroline iron(II) sulfate complex (Ferroin), N-Ethoxychrysoidine, 2,2'-Bipyridine (Fe complex), 5,6-Dimethylphenanthroline (Fe complex), o-Dianisidine, Sodium diphenylamine sulfonate, Diphenylbenzidine, Diphenylamine, Viologen, Sodium 2,6-Dibromophenol-indophenol, Sodium 2,6-Dichlorophenol-indophenol, Sodium o-Cresol indophenol, Thionine (Lauth's violet), Methylene blue, Indigotetrasulfonic acid, Indigotrisulfonic acid, Indigo carmine (Indigodisulfonic acid), Indigomono sulfonic acid, Phenosafranin, Safranin, Neutral red, labels disclosed in any document incorporated herein, and labels disclosed in Schwarzländer M et al, Antioxid Redox Signal. 2016 May 1; 24(13):680-712, which is hereby incorporated by reference in its entirety.

In another embodiment, a method comprises or a bioreactor or harvest vessel is capable of providing extracellular agents, e.g., metabolites, transition state metal ion as described herein, to the production culture.

In some embodiments, a bioreactor or bioreactor for use in a method of the disclosure can be set up according to the following principles:

The functional set up of the bioreactor while the production cultures is harvested is important in ensuring the culture exiting the bioreactor is well oxygenated and carries dissolved oxygen into the subsequent processing steps. Once cell culture has reached the target temperature to initiate the harvest step ensure all process controls that are likely to antagonize the oxygenation of the production culture are inhibited. These may include inhibition of sparged nitrogen gas flow if active, inhibition of on demand $CO_2$ gas flow control if active, inhibition of on demand alkali control if active, and inhibition of feed application if active.

The nitrogen sparge gas flow is normally used as a ballast to control dissolved oxygen tension (DOT) to a set point when the cellular demand for oxygen is low, however this may be kept actively flowing during the course of the production stage. Nitrogen is also used in airlift bioreactors as carrier ballast to maintaining mixing in these vessels. However where nitrogen sparge gas is used it must be inhibited to prevent diluting the oxygen composition of sparged gases used for aerating the production culture during the harvest step as this will prevent the dissolved oxygen, DOT in the culture from reaching 100% air saturation (if air only sparge is used) or the maximum DOT expected (if a blend of air and oxygen is used). Sparged nitrogen therefore limits the maximum dissolved oxygen concentration expected for a given sparge of air alone or sparge of air-oxygen mixture. The $CO_2$ gas flow is sparged into the production culture in response to process pH rising above control range. When the $CO_2$ gas flow sparge is active it also dilutes the oxygen composition of the sparge gas which in turn limits the maximum dissolved oxygen concentration expected for a given sparge of air alone or sparge of air-oxygen mixture. Therefore its inactivation during the harvesting of production culture prevents the dilution of the aerating sparge gas.

Addition of alkali solution to the production culture in response to the process pH falling below the control range is needed for tight pH control during the cultivation of the production culture. However there are potential risks of greater cell damage and cell death with application of alkali solution while the production culture is being harvested due to a continually decrease operating volume and overdosing of the alkali solution. The application of feeds into the production culture is necessary while the culture is actively growing and metabolizing. However during the harvest the continually decreasing operating volume impacts the mixing behavior of the bioreactor and result in greater cell damage and cell death with application of feed solution due to the non-physiological nature of feeds (high osmolality and high or low pH) and micro-environments created in poorly mixed vessels.

Once production culture has reached the target temperature to initiate the harvest step ensure all process controls that are likely to promote the oxygenation of the production culture are activated. These may include activation of sparged air and/or oxygen gas flow if not active, activation of head-space air and/or oxygen flow, if not active, and finally activation of head-space pressure if not active. The on-demand air and or oxygen sparge flow may become very low or even stop once the production culture has stopped growing, or when it is cooled down, in readiness for harvest. The continued application of air and oxygen sparge at various continuous fixed flow rates is critical to oxygenating the production culture and in ensuring the production culture carries dissolved oxygen into the cell clarifying filter housings or centrifuge and flow paths between the bioreactor and filter housing or centrifuge and between the filter housing or centrifuge and supernatant collection vessel (e.g., harvest vessel). The head-space or overlay aeration is typically active during the cultivation of the production culture and ensures bioreactor head-space is continually purged of metabolic $CO_2$ gas. The continued overlay aeration of the production culture during harvest promotes surface oxygenation of the culture albeit more slowly than achieved with sparge gases but avoid production of foam while the production culture is draining out of the bioreactor.

For bioreactors capable of operating with head-space pressure and where pressure is used during the cultivation of production culture to aid greater solubility of gases into the liquid phase (culture) or to maintain a positive pressure within the bioreactor to prevent ingress of environmental contaminants across the vessel's sterile boundaries it is recommended that this is maintained during the harvest. In practice where the harvest is driven by pressure the culture oxygenation will be aided provided the gas used to pressurize the bioreactor is air or a mixed blend of air and oxygen. However if the harvest is driven by a pump, head-space pressure is not typically used. The use of head-space pressure, with an air or air/oxygen gas mixture, in such circumstances is beneficial in aiding culture oxygenation and resisting the harvest tubing from collapsing under the suction head upstream of the pump head when culture is flowing at required fast rates dependent on scale of operation needed during the harvesting operation.

For single use bioreactors the design of the harvest line with respect to internal bore size and wall strength to resist collapsing under suction produced upstream of the pump head at high flow rates is important in ensuring the harvest flow rate is not impeded through tube occlusion. The impact of tube occlusion is not only in restricting the harvest flow rate but may promote greater cell death and cell lysis and degassing of dissolved oxygen from the culture. The tube occlusion impacts have the potential to expose the cells and product to hypoxic/anoxia environment with the filter housing through increase the residence time in the housing at slower flow rate, promote the release of intracellular factors through greater cell death and cell lysis passing through a constricted opening and remove the dissolved oxygen from the culture by degassing within the suction zone and so lower amounts of the dissolved oxygen carried by the culture into the filter housings. In one embodiment, the methods disclosed herein avoid these negative impact on product stability.

The internal diameter of the harvest tubing and choice of pump used are selected to attain the required flow rate to achieve the process volumetric throughput (Litres of process supernatant per filter area, $L/m^2$) for the cell clarification step by depth filters or centrifuge coupled to depth filters. The material of construction of the harvest line needs to have the rigidity to resist collapsing in the suction head produced upstream of the pump head. It is proposed materials other the commonly-used platinum-cured silicon or C-flex be used in the construction of the harvest tubing. The use of braided tubing may be considered as an alternative to the commonly used materials.

In some embodiments, a method comprises or a bioreactor is capable of optimization of depth filter area to avoid fouling and blockage of the filters during the filter clarification step and thereby minimizing the residence time of the cell culture within the filter housings is integral step in ensuring the oxygenation of the production culture and the dissolved oxygen it carries out of the bioreactor is not exhausted while the culture flows into and resides in the filter housings before passing out as supernatant. Furthermore, the flow rate should be adequate to minimize the residence time of the supernatant between the clarification step (filter housing) and the c supernatant collection vessel (e.g., harvest vessel).

The cell clarification filter (primary, secondary and tertiary) areas are optimized to ensure the required process volumetric throughput is met without loss of flux (L/m2/h) or filtrate quality (through breakthrough of particulate) across the filters to the extent that it impacts the performance of secondary or Stage 2 and tertiary or Stage 3 filters downstream of the primary or Stage 1 filters. Additionally, the filter area and filter types selected for optimal cell clarification must avoid higher pressure differentials between the different filter stages which signifies filter fouling and imminent filter blockage. It is therefore expected that a decrease in the flux across the different serially-coupled filters would lead to increased residence time within the filter housings and leading to greater consumption/exhaustion of dissolved oxygen in the supernatant within the filter housing leading to hypoxia in the supernatant. The buildup of higher pressure differential between the primary and secondary stage filters is also problematic inasmuch it promotes higher cell lysis and release of cellular factors which when active destabilize the product.

In some embodiments, a method comprises or a bioreactor is capable of ensuring the cell-free supernatant is collected in well aerated and mixed harvest vessel (steel or single-use). The harvest vessel is designed to ensure it promote good surface oxygenation through: impinging collected filtrate onto the vessel wall surface by designing internal nozzle directed towards the vessel wall that force the filtrate to cascade down vessel walls; and/or
ability to fill the harvest vessel before filtrate collection with a gaseous environment composed of air or any given blend of air and oxygen to promote oxygenation of the collected filtrate to greater than >40% air saturation and ≤500% air saturation.

In one embodiment, the harvest vessel is stainless steel harvest vessel. The method of supernatant collection and the design of the harvest vessel is the final element of the approach to protect the product during the harvesting step. Currently the harvested supernatant is collected in jacketed stainless steel vessels with a mixer to continually mix the collected supernatant. The harvested supernatant is discharged into the harvest vessel through headspace ports with an internal T tube that directs the stream of supernatant onto the wall of the vessel from where it cascade down the walls to collect at the bottom of the tank. Additionally, these stainless steel vessels are filled with sterile air to keep the vessel pressurized above atmospheric pressure after they have been steam-in-place sterilized to prevent ingress of environmental contaminants across the vessel sterile boundaries. It is postulated that the harvest supernatant collected in these vessels is oxygenated as it cascades down the vessel wall under an atmosphere of pressurized air. Further oxygenation of the supernatant occurs through surface contact with the headspace above the collected supernatant.

In another embodiment, the harvest vessel is single use harvest vessel. The single use supernatant harvest vessels are gamma-irradiate and evacuated bag. During the supernatant collection the bag fills and displaces the vacuum with no gaseous headspace being formed above the collected supernatant. These bags do not have an agitator therefore collected supernatant cannot be mixed and the bags are installed into unjacketed plastic or stainless steel shells which cannot heat or cool the collected supernatant. Once the bags are filled with supernatant they are transferred into +5° C. storage for up to 14 days. The purification process may start with the primary capture step immediately after the harvest or within the 14 days hold period.

The approach to ensure the oxygenation of the production culture is maintained at a DOT in the range of greater than 40% air saturation to less than 500% air saturation during the harvesting step intends to 'load' the production culture with dissolved oxygen which is expected to be carried into and across the clarification step such that when the supernatant is collected it has sufficient dissolved oxygen to prevent the activation of cellular factors which may promote product dissociation. The harvest vessel is designed with to ensure the harvested supernatant continues to remain in a well oxygenated state while held under +5° C. storage for up to 14 days. This is achieved by a vessel design that ensures the supernatant continues to oxygenate while being collected and held under +5° C. storage, e.g., by surface aeration. In one embodiment, the harvest vessel design comprises the following features:

- The vessel or single-used bag has an agitator/mixer that provides sufficient axial bulk mixing to allow collected supernatant to oxygenate through surface aeration.
- The vessel or single use bag shell is jacketed with appropriately sized thermo-circulator to permit the temperature of vessel content to reach +5° C., e.g., within 4 h from room temperature and heat up to room temperature from +5° C. within similar duration.
- The vessel or single use bag shell is fitted with appropriately sized air and oxygen gas mass flow controllers to permit headspace aeration with air, oxygen or an oxygen-enriched gas.
- The vessel or single use bag and shell are fitted with an overlay gas filter (suitable for air and oxygen gases at flow rate appropriate for scale of operation and an exit gas vent filter suitable for air and oxygen gases at flow rate appropriate for scale of operation, to permit a continuous flow of air and oxygen across the headspace to fill the harvest vessel before supernatant filtrate collection with a gaseous environment composed of air or any given blend of air and oxygen to promote oxygenation of the supernatant filtrate to greater than >40% air saturation and ≤500% air saturation while supernatant filtrate collection and once collection is completed.
- The vessel or single use bag and shell are fitted with pressure sensor and safety interlock to stop headspace gases if pressure exceed safety limit for the scale of operation and vessel design.
- The vessel or single use bag and shell are fitted with process sensor ports for pH, DOT, Redox and temperature. The probe location within vessel or bag allows monitoring at the lowest operating volume appropriate for the scale of operation.
- The vessel or single use bags are fitted with addition ports on the top of the container with ports fitted with internal nozzles directing flow of liquid onto the vessel wall and promoting the liquid to cascade down the vessel wall.

Cells and Cell Culture

In one aspect, the present disclosure relates to methods and compositions for engineering or making a cell or cell line that produces a product, e.g., a recombinant product, e.g., a stabilized product, e.g., a stabilized protein, as described herein. In another aspect, the present disclosure relates to methods and compositions for engineering or making a cell or cell line with improved, e.g., decreased dissociation, increased productivity and/or product quality.

In embodiments, the cell is a mammalian or non-mammalian cell, e.g., an insect cell, a yeast cell, a fungal cell, a plant cell, an archaeal cell, e.g., a cell from a species of Archaea, or a bacterial cell. In an embodiment, the cell is from human, mouse, rat, Chinese hamster, Syrian hamster, monkey, ape, dog, duck, horse, parrot, ferret, fish or cat. In an embodiment, the cell is an animal cell. In embodiments, the cell is a mammalian cell, e.g., a human cell or a rodent cell, e.g., a hamster cell, a mouse cell, or a rat cell. In an embodiment, the cell is a prokaryotic cell, e.g., a bacterial cell. In an embodiment, the cell is a species of Actinobacteria, e.g., *Mycobacterium tuberculosis*).

In one embodiment, the cell is a Chinese hamster ovary (CHO) cell. In one embodiment, the cell is a CHO-K1 cell, a CHO-K1 SV cell, a DG44 CHO cell, a DUXB11 CHO cell, a CHOS, a CHO GS knock-out cell, a CHO FUT8 GS knock-out cell, a CHOZN, or a CHO-derived cell. The CHO GS knock-out cell (e.g., GSKO cell) is, for example, a CHO-K1 SV GS knockout cell. The CHO FUT8 knockout cell is, for example, the Potelligent® CHOK1 SV (Lonza Biologics, Inc.).

In another embodiment, the cell is a HeLa, HEK293, HT1080, H9, HepG2, MCF7, Jurkat, NIH3T3, PC12, PER.C6, BHK (baby hamster kidney cell), VERO, SP2/0, NS0, YB2/0, Y0, EB66, C127, L cell, COS, e.g., COS1 and COS7, QC1-3, CHO-K1, CHOK1SV, Potelligent CHOK1SV, CHO GS knockout, CHOK1SV GS-KO, CHOS, CHO DG44, CHO DUXB11, and CHOZN, or any cells derived therefrom. In one embodiment, the cell is a stem cell. In one embodiment, the cell is a differentiated form of any of the cells described herein. In one embodiment, the cell is a cell derived from any primary cell in culture.

In an embodiment, the cell is any one of the cells described herein that produces a product, e.g., a product as described herein. In an embodiment, the cell is any one of the cells described herein that comprises an exogenous nucleic acid encoding a recombinant polypeptide, e.g., expresses a recombinant polypeptide, e.g., a recombinant polypeptide selected from Table 2 or 3.

In an embodiment, the cell culture is carried out as a batch culture, fed-batch culture, draw and fill culture, or a continuous culture. In an embodiment, the cell culture is an adherent culture. In an embodiment, the cell culture is a suspension culture. In one embodiment, the cell or cell culture is placed in vivo for expression of the recombinant polypeptide, e.g., placed in a model organism or a human subject.

For example, the methods are performed in a large-scale bioreactor, e.g., a bioreactor having at least two impellers, large-scale bioreactor systems and methods for large-scale cultivation and propagation of mammalian cells. In an embodiment, the bioreactor is a bioreactor as described in 2011/0312087.

In an embodiment, the cells are cultured in a bioreactor as disclosed in U.S. Ser. No. 62/242,758, the contents of which are incorporated herein in their entirety. Disclosed therein is a system and method for control of at least one bioreactor, other cell cultivation-related equipment, and systems containing any combination of these. For example, the system and method for bioreactor control may include controlling a plurality of bioreactors and other types of cultivation-related equipment, such as equipment for fermenting, harvesting, equipment for microfiltration and purification (e.g., liquid chromatography skid system), buffer preparation, media preparation, etc. The plurality of bioreactors and the other types of cultivation-related equipment may be located in a plant, and the control of such equipment may be known as a Plant-Wide Control System ("PWCS").

In an embodiment, the method is performed in a manufacturing facility that provides both batch and continuous manufacturing using at least one piece of single-use disposable technology, e.g., whose described in U.S. Ser. No. 62/246,478, the contents of which are incorporated herein in their entirety. In an embodiment, the manufacturing facility is for the production of active pharmaceutical ingredients ("API").

Cooling can be effected using methods known in the art. For example, larger reactors will typically have a water jacket through which thermo-slatted water passes to control the culture temperature. In embodiments, a process chilled water supply is delivered into the jacket to get substantial and rapid cooling. In embodiments, a refrigeration unit is used to remove heat. Cooling can be performed at one or more desired times when culturing (i.e., causing the number of cells to increase, or induce production of a desired product from a cell culture) or cooling the production culture at the end of production phase, or when harvesting cells. Because organisms differ in the optimal temperature at which they are grown, the cooling temperature will be selected based on the relatively higher temperature of the step or steps preceding the cooling step. In embodiments, cooling of cultured cells is performed to reduce the cellular rate of oxygen consumption so that the harvest stream remains oxygenated through the harvesting process.

For mammalian cell lines, culture process temperature shifts are typically to 27-35° C. (e.g., 27, 28, 29, 30, 31 or, 32, 33, 34 or 35° C.). In some embodiments, the temperature is decreased to 30-33° C. after exponential growth phase. Without wishing to be bound by theory, it is believed that dropping the temperature to 12-18° C., e.g., 15° C., after production phase reduces the specific rate of oxygen consumption 10 fold.

In an embodiment, the culture medium is free of serum.

Other suitable media and culture methods for mammalian cell lines are well-known in the art, as described in U.S. Pat. No. 5,633,162, for instance. Examples of standard cell culture media for laboratory flask or low density cell culture and being adapted to the needs of particular cell types are for instance: Roswell Park Memorial Institute (RPMI) 1640 medium (Morre, G., The Journal of the American Medical Association, 199, p. 519 f. 1967), L-15 medium (Leibovitz, A. et al., Amer. J. of Hygiene, 78, 1 p. 173 ff, 1963), Dulbecco's modified Eagle's medium (DMEM), Eagle's minimal essential medium (MEM), Ham's F12 medium (Ham, R. et al., Proc. Natl. Acad. Sc. 53, p 288 ff. 1965) or Iscoves' modified DMEM lacking albumin, transferrin and lecithin (Iscoves et al., J. Exp. med. 1, p. 923 ff., 1978). For instance, Ham's F10 or F12 media were specially designed for CHO cell culture. Other media specially adapted to CHO cell culture are described in EP-481 791. Other suitable cultivation methods are known to the skilled artisan and may depend upon the recombinant polypeptide product and the host cell utilized. It is within the skill of an ordinarily skilled artisan to determine or optimize conditions suitable for the expression and production of the product, e.g., the recombinant polypeptide, to be expressed by the cell.

Assays for quantifying the amount, level, or quantity of product produced or secreted, e.g., secreted into the culture media, include protein quantification assays, such as the Bradford protein assay, SDS-PAGE analysis, immunoblotting, e.g., western blot, and automated means, e.g., using a nanodrop device. Other methods for measuring increased protein production are well-known to those skilled in the art. For example, an increase in recombinant protein production might be determined at small-scale by measuring the concentration in tissue culture medium by ELISA (Smales et al. 2004 Biotechnology Bioengineering 88:474-488). It can also be determined quantitatively by the ForteBio Octet, for example for high throughput determination of recombinant monoclonal antibody (mAb) concentration in medium (Mason et al. 2012 Biotechnology Progress 28:846-855) or at a larger-scale by protein A HPLC (Stansfield et al. 2007 Biotechnology Bioengineering 97:410-424). Other methods for determining production of a product, e.g., a recombinant polypeptide described herein, can refer to specific production rate (qP) of the product, in particular the recombinant polypeptide in the cell and/or to a time integral of viable cell concentration (IVC). In an embodiment, the method for determining production includes the combination of determining qP and IVC. Recombinant polypeptide production or productivity, being defined as concentration of the polypeptide in the culture medium, is a function of these two parameters (qP and IVC), calculated according to Porter et al. (Porter et al. 2010 Biotechnology Progress 26:1446-1455). Methods for measuring protein production are also described in further detail in the Examples provided herein.

In one embodiment, the methods described herein produce a cell with improved product quality. In one embodiment, improvement of the quality of the product results in the increase, e.g., a 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 99%, or more, increase in product quality; or a 1-fold, 2-fold, 3-fold, 4-fold, 5-fold, 6-fold, 7-fold, 8-fold, 9-fold, 10-fold, 20-fold, 50-fold, or 100-fold, or more increase, in product quality, e.g., as compared to the amount, level, or quantity of product produced by a cell not subjected to lower temperature. Such increases in product quality can be exemplified, for example, by one or more of the following:

i) an increase or decrease in disulfide bond scrambling (e.g., an increase or decrease the desired isoform or structure as a result to increased or decreased disulfide bond scrambling, e.g., for antibody molecule products).

ii) an increase in the amount or quantity of non-aggregated product (or a decrease in the amount or quantity of aggregated product);

iii) an increase in the amount or quantity of properly folded or assembled product (or a decrease in the amount or quantity of misfolded, unfolded, partially assembled, or non-assembled product), or an increase in the ratio of properly folded or assembled product to unfolded, misfolded, partially assembled, or non-assembled product;

iv) an increase in the amount or quantity of full-length product (or a decrease in fragmentation of the product);

v) an increase in the desired post-translational modifications (or a decrease in unmodified or incorrectly modified product);

vi) an increase or decrease in glycan heterogeneity (e.g., for glycosylated products);

vii) an increase in the amount or quantity of functional product (or a decrease in the amount or quantity of a nonfunctional or disfunctional product), or an increase in the ratio of function to nonfunctional or dysfunctional product; and/or Methods for measuring product quality, e.g., the improvement of the product quality, of a cell or cell line generated as described herein are known in the art. In one embodiment, methods for determining the fidelity of the primary sequence of the expressed recombinant polypeptide product are known in the art, e.g., mass spectrometry. An increase in the amount or concentration of properly folded product, e.g., expressed recombinant polypeptide, can be determined by circular dichroism or assessing the intrinsic fluorescence of the expressed recombinant polypeptide. An increase in the amount or concentration of functional product can be tested using various functional assays depending on the identity of the recombinant product, e.g., recombinant polypeptide. For example, antibodies can be tested by the ELISA or other immunoaffinity assay. Other methods for determining an increase in product quality, e.g., determining aggregation, post-translational modifications, disulfide bond scrambling, can be assessed by size exclusion chromatography, high performance liquid chromatography, dynamic light scattering (DLS) approaches, and protein electrophoresis (PAGE) methods.

In some embodiments, additional steps may be performed to improve the expression of the product, e.g., transcription, translation, and/or secretion of the product, or the quality of the product, e.g., proper folding and/or fidelity of the primary sequence. Such additional steps include introducing an agent that improves product expression or product quality. In an embodiment, an agent that improves product expression or product quality can be a small molecule, a polypeptide, or a nucleic acid that encodes a polypeptide that improves protein folding, e.g., a chaperone protein. In an embodiment, the agent that assists in protein folding comprises a nucleic acid that encodes a chaperone protein, e.g., BiP, PD1, or ERO1 (Chakravarthi & Bulleid 2004; Borth et al. 2005; Davis et al. 2000). Other additional steps to improve yield and quality of the product include overexpression of transcription factors such as XBP1 and ATF6 (Tigges & Fussenegger 2006; Cain et al. 2013; Ku et al. 2008) and of lectin binding chaperone proteins such as calnexin and calreticulin (Chung et al. 2004). Overexpression of the agents that assist or improve protein folding, product quality, and product yield described herein can be achieved by introduction of exogenous nucleic acids encoding the agent. In another embodiment, the agent that improves product expression or product quality is a small molecule that can be added to the cell culture to increase expression of the product or quality of the product, e.g., DMSO. In one embodiment, maintaining the cells at a lower temperature, e.g., 1° C., 2° C., 3° C., 4° C., 5° C., 6° C., 7° C., 8° C., 9° C., or 10° C. lower, than the temperature that the cells are normally grown can improve the quality of the product by reducing or eliminating dissociation of the product.

Any of the methods described herein can further include additional selection steps for identifying cells that have high productivity or produce high quality products. For example, FACs selection can be utilized to select specific cells with desired characteristics, e.g., higher expression of a protein folding proteins, e.g., chaperones.

In one aspect, the disclosure provides methods that include a step for recovering or retrieving the recombinant polypeptide product. In embodiments where the recombinant polypeptide is secreted from the cell, the methods can include a step for retrieving, collecting, or separating the recombinant polypeptide from the cell, cell population, or the culture medium in which the cells were cultured. In embodiments where the recombinant polypeptide is within the cell, the purification of the recombinant polypeptide product comprises separation of the recombinant polypeptide produced by the cell from one or more of any of the following: host cell proteins, host cell nucleic acids, host cell lipids, and/or other debris from the host cell.

In embodiments, the process described herein provides a substantially pure protein product. As used herein, "substantially pure" is meant substantially free of pyrogenic materials, substantially free of nucleic acids, and/or substantially free of endogenous cellular proteins enzymes and components from the host cell, such as polymerases, ribosomal proteins, and chaperone proteins. A substantially pure protein product contains, for example, less than 25%, 20%, 15%, 10%, 9%, 8%, 7%, 6%, 5%, 4%, 3%, 2%, or 1% of contaminating endogenous protein, nucleic acid, or other macromolecule from the host cell.

Methods for recovering and purification of a product, e.g., a recombinant polypeptide, are well established in the art. For recovering the recombinant polypeptide product, a physical or chemical or physical-chemical method is used. The physical or chemical or physical-chemical method can be a filtering method, a centrifugation method, an ultracentrifugation method, an extraction method, a lyophilization method, a precipitation method, a chromatography method or a combination of two or more methods thereof. In an embodiment, the chromatography method comprises one or more of size-exclusion chromatography (or gel filtration), ion exchange chromatography, e.g., anion or cation exchange chromatography, affinity chromatography, hydrophobic interaction chromatography, and/or multimodal chromatography.

In embodiments, reduction in temperature is combined with reducing temperature with reducing pH, thioredoxin inhibitors, e.g., metal ions. In embodiments, the combination treatment is performed in a bioreactor as described above.

NUMBERED EMBODIMENTS

The present invention may be defined in any of the following numbered paragraphs.

1. A method of producing a stabilized product, e.g., a stabilized protein, expressed in a recombinant host cell, comprising:

maintaining a redox potential difference in the range of −10 mV to −1000 mV, −20 mV to −800 mV, −30 mV to −700 mV, −40 mV to −600 mV, −50 mV to −500 mV, −50 mV to −400 mV, −50 mV to −300 mV, −50 mV to −200 mV, or −50 mV to −150 mV, e.g., −50 mV to −300 mV, from a non-stabilized product to a stabilized product during separation of cells from production culture and collection of a supernatant, wherein separation of cells from a production culture and collection of supernatant is conducted without sparging or sufficiently little sparging that the sparging does not substantially alter the redox potential in the production culture and the supernatant, thereby producing a stabilized product, e.g., an isolated, stabilized protein.

2. A method of producing a stabilized product, e.g., a stabilized protein, expressed in a recombinant host cell, comprising:

providing, e.g., establishing, a redox potential difference in the range of −10 mV to −1000 mV, −20 mV to −800 mV, −30 mV to −700 mV, −40 mV to −600 mV, −50 mV to −500 mV, −50 mV to −400 mV, −50 mV to −300 mV, −50 mV to −200 mV, or −50 mV to −150 mV, e.g., −50 mV to −300 mV, from a non-stabilized product to a stabilized product in a post-exponential growth culture phase of a production culture, and maintaining a redox potential difference in the range of −10 mV to −1000 mV, −20 mV to −800 mV, −30 mV to −700 mV, −40 mV to −600 mV, −50 mV to −500 mV, −50 mV to −400 mV, −50 mV to −300 mV, −50 mV to −200 mV, or −50 mV to −150 mV, e.g., −50 mV to −300 mV, from a non-stabilized product to a stabilized product during separation of cells from production culture and collection of a supernatant, wherein separation of cells from a production culture and collection of supernatant is conducted without sparging or sufficiently little sparging that the sparging does not substantially alter the redox potential in the production culture and the supernatant, thereby producing a stabilized product, e.g., an isolated, stabilized protein.

3. The method of either of paragraphs 1 or 2, wherein the method further comprises establishing a dissolved oxygen tension (DOT) in the range of greater than 10, 20, 30, 40, 50, or 60% to less than or equal to 70, 80, 90, 100, 150, 200, 250, 300, 350, 400, 450, or 500% air saturation, e.g., greater than 40% to less than or equal to 500%, during separation of cells from production culture.

4. A method of producing a stabilized product, e.g., a stabilized protein, expressed in a recombinant host cell, comprising:

providing, e.g., establishing a redox potential difference in the range of −10 mV to −1000 mV, −20 mV to −800 mV, −30 mV to −700 mV, −40 mV to −600 mV, −50 mV to −500 mV, −50 mV to −400 mV, −50 mV to −300 mV, −50 mV to −200 mV, or −50 mV to −150 mV, e.g., −50 mV to −300 mV, from a non-stabilized product to a stabilized product in a post-exponential growth culture phase of the production culture, wherein dissolved oxygen tension (DOT) from start of the production phase to the end of the production phase is in a range of greater than 40% to 70% air saturation;

cooling the production culture at the end of production phase to a $T_{harvest}$ temperature, which is a temperature that is below the temperature at which the cell line was or is normally cultured;

increasing the DOT to a range of greater than 10, 20, 30, 40, 50, or 60% to less than or equal to 70, 80, 90, 100, 150, 200, 250, 300, 350, 400, 450, or 500% air saturation, e.g., greater than 40% to less than or equal to 500% air saturation, by sparging air or $O_2$ gas into the production culture until separation of cells from production culture and collection of supernatant; and maintaining a redox potential difference in the range of −10 mV to −1000 mV, −20 mV to −800 mV, −30 mV to −700 mV, −40 mV to −600 mV, −50 mV to −500 mV, −50 mV to −400 mV, −50 mV to −300 mV, −50 mV to −200 mV, or −50 mV to −150 mV, e.g., −50 mV to −300 mV, from a non-stabilized product to a stabilized product during separation of cells from production culture and collection of a supernatant, wherein separation of cells from a production culture and collection of supernatant is conducted without sparging or sufficiently little sparging that the sparging does not substantially alter the redox potential in the production culture and the supernatant, thereby producing a stabilized product, e.g., an isolated, stabilized protein.

5. The method of any of paragraphs 1-4, wherein the method further comprises providing, e.g., adding, transition metals in or to the production culture, wherein the transition metal ions are selected from $Zn^{2+}$, $Mn^{4+}$, $Cu^{2+}$, $Fe^{3+}$, $Co^{2+}$, $Cr^{3+}$, and/or $Ni^{2+}$.

6. The method of any of paragraphs 1-5, wherein the DOT is further maintained by one or more actions selected from the group consisting of: inhibiting sparged nitrogen gas flow if active, inhibiting on demand alkali control if active, inhibiting on demand CO2 gas flow control if active, by inhibiting feed addition if active, activating head space pressure if not active, and activating head space flow of air/$O_2$ if not active.

7. A method of producing a stabilized product, e.g., a stabilized protein, expressed in a recombinant host cell, comprising:

(i) providing, e.g., establishing, a production culture, e.g., a post-exponential growth culture, comprising a recombinant host cell expressing the product, e.g., a protein, at a redox potential difference in the range of −10 mV to −1000 mV, −20 mV to −800 mV, −30 mV to −700 mV, −40 mV to −600 mV, −50 mV to −500 mV, −50 mV to −400 mV, −50 mV to −300 mV, −50 mV to −200 mV, or −50 mV to −150 mV, e.g., −50 mV to −300 mV, from a non-stabilized product to a stabilized product;

(ii) maintaining a redox potential difference in the range of −10 mV to −1000 mV, −20 mV to −800 mV, −30 mV to −700 mV, −40 mV to −600 mV, −50 mV to −500 mV, −50 mV to −400 mV, −50 mV to −300 mV, −50 mV to −200 mV, or −50 mV to −150 mV, e.g., −50 mV to −300 mV, from a non-stabilized product to a stabilized product in a post-growth culture phase; and (iii) maintaining a redox potential difference in the range of −10 mV to −1000 mV, −20 mV to −800 mV, −30 mV to −700 mV, −40 mV to −600 mV, −50 mV to −500 mV, −50 mV to −400 mV, −50 mV to −300 mV, −50 mV to −200 mV, or −50 mV to −150 mV, e.g., −50 mV to −300 mV, from a non-stabilized product to a stabilized product during separation of cells from production culture and collection of a supernatant, wherein separation of cells from a production culture and collection of supernatant is conducted without sparging or sufficiently little sparging that the sparging does not substantially alter the redox potential in the production culture and the supernatant, wherein the method comprises:

a. cooling the production culture after exponential growth phase has occurred, to a temperature of 30° C. to 33° C., which is a temperature that is below the temperature at which the cell line was or is normally cultured;

b. oxygenating the production culture, to an dissolved oxygen tension (DOT) greater than 40% to less than or equal to 70% air saturation from start of the production phase to the end of the production phase;

c. providing, e.g., adding, transition metals in or to the production culture, wherein the transition metals are selected from $Zn^{2+}$, $Mn^{4+}$, $Cu^{2+}$, $Fe^{3+}$, $Co^{2+}$, $Cr^{3+}$, and/or $Ni^{2+}$;

d. providing, e.g., adding, dehydroascorbic acid or ascorbic acid, or a dehydroascorbic acid or ascorbic acid modifying component, to the production culture;

e. providing, e.g., adding glutathione, e.g., oxidized and/ or reduced glutathione, or a glutathione modifying component, to the production culture; or f. cooling the production culture for separation of cells from production culture and collection of supernatant to a temperature $T_{harvest}$ of 12° C.-18° C., which is a temperature that is below $T_{production}$.

thereby producing a stabilized product, e.g., an isolated, stabilized protein or a preparation of a stabilized product, e.g., a stabilized protein.

8. The method of paragraph 7, wherein the method comprises a, b, and f.

9. The method of paragraph 7, wherein the method comprises a, c, and f.

10. The method of paragraph 7, wherein the method comprises b and c.

11. The method of paragraph 7, wherein the method comprises a, b, c, and f.

12. The method of any of paragraphs 1-11, wherein the production culture has an oxygenation level of at least 10%, at least 30%, or between 30% and 70% air saturation.

13. The method of paragraph 12 wherein the oxygenation level is greater than 40% to less than or equal to 70% air saturation.

14. The method of any of paragraphs 4-13, wherein the transition metals are $Zn^{2+}$, $Mn^{2+}$, and/or $Cu^{2+}$.

15. The method of any of paragraphs 4-14, wherein $Zn^{2+}$ is present at a concentration of 10, 20, 40, 60, 80, 100, 120, 140, 160, 180, 200, 220, or 250 to 300, 320, 340, 360, 380, 400, 420, 440, 460, 480, 500, 550, 600, 650, 700, or 1000 μM, e.g., 200-400 μM.

16. The method of any of paragraphs 4-15, wherein $Mn^{2+}$ is present at a concentration of 1, 2, 3, 4, 5, 6, 7, 8, 9, 10, 11, 12, 13, 14, 15, 20, 30, 40, or 50 to 60, 70, 80, 90, 100, 120, 140, 160, 180, or 200 μM, e.g., 10-100 μM.

17. The method of any of paragraphs 4-16, wherein $Cu^{2+}$ is present at a concentration of 1, 2, 3, 4, 5, 6, 7, 8, 9, 10, 11, 12, 13, 14, 15, 20, 30, 40, or 50 to 60, 70, 80, 90, 100, 120, 140, 160, 180, or 200 μM, e.g., 10-100 μM.

18. The method of any of paragraphs 4-17, wherein $Zn^{2+}$ is present at a concentration of 200 to 400 μM, $Mn^{2+}$ is present at a concentration of 10-100 μM, and $Cu^{2+}$ is present at a concentration of 10-100 μM.

19. The method of any of paragraphs 1-18, wherein the stabilized protein comprises an $N^{th}$ cysteine residue and an $N+1^{th}$ cysteine residue, wherein N=1, 2, 3, 4, 5, 6, 7, 8, 9, 10, 11, 12, 13, 14, 15, 16, 17, 18, 19, 20, 30, 40, 50, 60, 70, 80, 90, 100 or more, e.g., N=1 or N=3.

20. The method of paragraph 19, wherein, in native form, the stabilized protein comprises a disulfide bond between the $N^{th}$ cysteine residue and an $N+1^{th}$ cysteine residue.

21. The method of paragraph 20, wherein:
  i) N=1, and in native form, the polypeptide comprises a disulfide bond between a first cysteine residue and a second cysteine residue;
  ii) N=3, and in native form, the polypeptide comprises a disulfide bond between a third cysteine residue and a fourth cysteine residue; or
  iii) N=3, and in native form, the polypeptide comprises a disulfide bond between a first cysteine residue and a second cysteine residues and a disulfide bond between a third cysteine residue and a fourth cysteine residue.

22. The method of any of paragraphs 1-21, wherein at least 80, 85, 90, 95, 96, 97, 98, or 99% by weight of the stabilized product, e.g., stabilized protein, is in a predetermined state, e.g., native confirmation, e.g., as determined by size separation, e.g., by gel electrophoresis, e.g., by non-reducing gel electrophoresis.

23. The method of any of paragraphs 1-22, wherein the product is an antibody, and at least 80, 85, 90, 95, 96, 97, 98, or 99% by weight of the antibody is in a predetermined state, e.g., native confirmation, e.g., as determined by size separation, e.g., by gel electrophoresis, e.g., by non-reducing gel electrophoresis.

24. The method of any of paragraphs 1-23, wherein the product is an antibody, and at least 80, 85, 90, 95, 96, 97, 98, or 99% by weight of the antibody is a tetramer comprising two chains each comprising a light chain variable region and two chains each comprising a heavy chain variable region.

25. The method of any of paragraphs 4-24, wherein $T_{harvest}$ is sufficiently low to inhibit dissociation of the disulfide bond.

26. The method of any of paragraphs 4-25, comprising separating the cells, from the production culture at $T_{harvest}$.

27. The method of any of paragraphs 4-26, wherein the cell line is cultured at a first temperature, $T_{culture}$, and is harvested at $T_{harvest}$.

28. The method of paragraph 27, wherein $T_{harvest}$ is at least 19° to 25° C. below $T_{culture}$.

29. The method of any of paragraphs 4-28, wherein $T_{harvest}$ is 12° C.-18° C., e.g., 15° C.

30. The method of any of paragraphs 27-29, wherein $T_{culture}$ is 30° C.-38° C.

31. The method of any of paragraphs 4-30, wherein the protein, e.g., as a component of the supernatant, is applied to a filter at $T_{harvest}$.

32. The method of any of paragraphs 1-31, wherein the cells are cultured in a bioreactor.

33. The method of paragraph 32, wherein the contents of the bioreactor are cooled to $T_{harvest}$ after production phase.

34. The method of paragraph 32, wherein the cell culture is cooled by contact with a member, e.g., a cooling jacket, comprising a fluid, e.g., water, at a temperature suitable for bring the cell culture to $T_{harvest}$.

35. The method of any of paragraphs 32-34, wherein the bioreactor has a volume of 1-250 milliliters, 250 milliliters to 50 liters, 50 to 800 liters, or 800-200,000 liters.

36. The method of any of paragraphs 32-35, wherein the bioreactor is a single use bioreactor, e.g., a bioreactor designed to allow incubation of a cell culture and thereafter being disposed, e.g., as described herein.

37. The method of any of paragraphs 32-36, wherein the bioreactor comprises a bioprocess container, a shell, at least one agitator, at least one sparger, at least one gas filter inlet port for the sparger(s) and headspace overlay, at least one fill port, at least one harvest port, at least one sample port, and at least one probe.

38. The method of any of paragraphs 32-37, wherein the bioreactor comprises processes and probes for monitoring and maintaining one or more parameters, e.g., pH, dissolved oxygen tension (DOT), or temperature.

39. The method of any of paragraphs 32-37, wherein the bioreactor is a self-supporting biocompatible tank having a volume of at least 4000 L and at least one top impeller and at least one bottom impeller, and wherein the at least one top impeller is a hydrofoil impeller, and wherein an impeller spacing ($D_s$) between the top impeller and the bottom impeller is at least 1.229× the diameter of the bottom impeller ($D_{bottom}$) and at most 2×$D_{bottom}$, wherein a liquid height above the top impeller ($D_o$) is at least 0.3× the diameter of the top impeller ($D_{top}$) and at most 2.5×$D_{top}$, and wherein a bottom clearance ($D_c$) between the tank bottom and the center-line of the bottom impeller is at least 0.35× $D_{bottom}$.

40. The method of any of paragraphs 32-39, wherein the bioreactor is operably coupled to a harvest vessel.

41. The method of paragraph 40, wherein the harvest vessel is configured to comprise or provide a head space above the reservoir culture, e.g., wherein the head space comprises a gas, e.g., air or oxygen, or a mixture of gases, e.g., air or air and oxygen.

42. The method of paragraph 41, wherein the harvest vessel is configured to allow collection of supernatant though a J-tube port into the head space such that the supernatant travels or cascades down the wall(s) of the harvest vessel.

43. The method of paragraph 42, wherein supernatant is transmitted onto a surface of the harvest vessel, e.g., a wall, in the head space, and flows along the surface, back to the reservoir culture.

44. The method of paragraph 43, wherein supernatant travel or cascade in the harvest vessel results in an increase in oxygenation level of the supernatant.

45. The method of any of paragraphs 40-44, wherein the DOT of the supernatant is maintained at a range of greater than 10, 20, 30, 40, 50, or 60% to less than or equal to 70, 80, 90, 100, 150, 200, 250, 300, 350, 400, 450, or 500% air saturation, e.g., greater than 40% to less than or equal to 500%, air saturation, in the harvest vessel through surface aeration.

46. The method of any of paragraphs 40-45, wherein the harvest vessel comprises a cooling device and mechanism to further cool the reservoir culture to a temperature of 5° to 8° C.

47. The method of any of paragraphs 40-46, wherein the harvest vessel comprises a mixer device capable of axial mixing and an pH titrant addition port.

48. The method of any of paragraphs 40-47, wherein the harvest vessel comprises at least one head space gas inlet port and at least one gas outlet port.

49. The method of any of paragraphs 40-48, wherein the harvest vessel further comprises at least one air flow controller and at least one $O_2$ flow controller to provide an air and $O_2$ mix.

50. The method of any of paragraphs 40-49, wherein the harvest vessel comprises sensors that detect DOT, redox, temperature and pH of the supernatant.

51. The method of paragraph 50, wherein the DOT, redox, temperature and pH sensor output are used to effect change in the sparge rates, head space, and feed or supplement addition into the bioreactor production culture prior to separation; and addition of pH titrant into the harvest vessel.

52. The method of paragraph 50, wherein the DOT, redox, temperature and pH sensor output are used to effect change addition of pH titrant into the harvest vessel.

53. The method of any of paragraphs 40-52, wherein the bioreactor is connected to the harvest vessel using a tubing resistant to occlusion.

54. The method of paragraph 53, wherein the tubing resistant to occlusion is braided.

55. The method of any of paragraphs 40-54, wherein the flow path between the bioreactor and the harvest vessel comprises installations of DOT and redox sensors/probes.

56. The method of paragraph 55, wherein the DOT and redox sensors/probes output is used to effect change in the sparge rates, head space, and feed or supplement addition into the bioreactor production culture prior to harvest.

57. The method of any of paragraphs 40-56, wherein the bioreactor comprises an element, e.g., a line or nozzle, configured to deliver culture to a surface defining the headspace of the bioreactor.

58. The method of any of paragraphs 40-57, wherein the bioreactor comprises a second element, e.g., a line or nozzle, configured to deliver culture to a surface defining the headspace of the bioreactor.

59. The method of any of paragraphs 1-58, further comprising monitoring the redox potential of cells within the culture and while isolating the protein for the purpose of maintaining the redox potential.

60. The method of paragraph 59, wherein monitoring the redox potential comprises using in-line monitoring probes, e.g., Mettler Toledo as described herein.

61. The method of paragraph 58, wherein monitoring the redox potential comprises evaluating redox status of the cellular factors that impact product stability wherein the cellular factors may compromise an enzyme or metabolic cofactor of the glutathione/reduced glutathione pathway, thioredoxin/reduced thioredoxin pathway, or pentose phosphate pathways (e.g., glutathione reductase, thioredoxin, glucose-6-phosphate, NADPH, NADP+, 6-phosphonoglucolactone, 6-phosphogluconate, or ribulose-5-phosphate).

62. The method of any of paragraphs 1-61, wherein the recombinant host cell is a CHO-K1 cell, a CHO-K1 SV cell, a DG44 CHO cell, a DUXB11 CHO cell, a CHOS, a CHO GS knock-out cell, a CHO FUT8 GS knock-out cell, a CHOZN, or a CHO-derived cell. The CHO GS knock-out cell (e.g., GSKO cell) is, for example, a CHO-K1SV GS knockout cell (Lonza Biologics, Inc.). The CHO FUT8 knockout cell is, for example, the Potelligent® CHOK1 SV (Lonza Biologics, Inc.).

63. The method of any of paragraphs 1-61, wherein the recombinant host cell is a CHO-GSKO cell, a CHOXceed cell CHO GS knock-out cell (e.g., GS-CHO cell) is, for example, a CHO-K1SV GS knockout cell (Lonza Biologics, Inc.). The CHO FUT8 knockout cell is, for example, the Potelligent® CHOK1 SV (Lonza Biologics, Inc.).

64. The method of any of paragraphs 1-61, wherein the recombinant host cell is a Hela, HEK293, HT1080, H9, HepG2, MCF7, Jurkat, NIH3T3, PC12, PER.C6, BHK (baby hamster kidney cell), VERO, SP2/0, NS0, YB2/0, Y0, EB66, C127, L cell, COS, e.g., COS1 and COST, QC1-3, CHOK1, CHOK1SV, Potelligent CHOK1SV, CHO GS knockout, CHOK1SV GS-KO, CHOS, CHO DG44, CHO DXB11, and CHOZN, or any cells derived therefrom.

65. A stabilized protein produced by the method of any of paragraphs 1-64.

66. A pharmaceutical composition comprising the stabilized protein of paragraph 65.

67. The pharmaceutical composition of paragraph 66, further comprising a pharmaceutically acceptable carrier, diluent, or excipient.

68. A bioreactor capable of producing a stabilized product, e.g., a stabilized protein, expressed in a recombinant host cell, wherein the bioreactor is capable of maintaining a redox potential difference in the range of −10 mV to −1000 mV, −20 mV to −800 mV, −30 mV to −700 mV, −40 mV to −600 mV, −50 mV to −500 mV, −50 mV to −400 mV, −50 mV to −300 mV, −50 mV to −200 mV, or −50 mV to −150 mV, e.g., −50 mV to −300 mV, from a non-stabilized product to a stabilized product during separation of cells from production culture and collection of a supernatant, wherein separation of cells from a production culture and collection of supernatant is conducted without sparging or sufficiently little sparging that the sparging does not substantially alter the redox potential in the production culture and the supernatant.

69. A bioreactor capable of producing a stabilized product, e.g., a stabilized protein, expressed in a recombinant host cell, wherein the bioreactor is capable of:

providing, e.g., establishing, a redox potential difference in the range of −10 mV to −1000 mV, −20 mV to −800 mV, −30 mV to −700 mV, −40 mV to −600 mV, −50 mV to −500 mV, −50 mV to −400 mV, −50 mV to −300 mV, −50 mV to −200 mV, or −50 mV to −150 mV, e.g., −50 mV to −300 mV, from a non-stabilized product to a stabilized product in a post-exponential growth culture phase of a production culture, and maintaining a redox potential difference in the range of −10 mV to −1000 mV, −20 mV to −800 mV, −30 mV to −700 mV, −40 mV to −600 mV, −50 mV to −500 mV, −50 mV to −400 mV, −50 mV to −300 mV, −50 mV to −200 mV, or −50 mV to −150 mV, e.g., −50 mV to −300 mV, from a non-stabilized product to a stabilized product during separation of cells from production culture and collection of a supernatant, wherein separation of cells from a production culture and collection of supernatant is conducted without sparging or sufficiently little sparging that the sparging does not substantially alter the redox potential in the production culture and the supernatant.

70. The bioreactor of either of paragraphs 68 or 69, wherein the bioreactor is capable of establishing a dissolved oxygen tension (DOT) in the range of greater than 10, 20, 30, 40, 50, or 60% to less than or equal to 70, 80, 90, 100, 150, 200, 250, 300, 350, 400, 450, or 500% air saturation, e.g., greater than 40% to less than or equal to 500% air saturation, during separation of cells from production culture.

71. A bioreactor capable of producing a stabilized product, e.g., a stabilized protein, expressed in a recombinant host cell, wherein the bioreactor is capable of:

providing, e.g., establishing a redox potential difference in the range of −10 mV to −1000 mV, −20 mV to −800 mV, −30 mV to −700 mV, −40 mV to −600 mV, −50 mV to −500 mV, −50 mV to −400 mV, −50 mV to −300 mV, −50 mV to −200 mV, or −50 mV to −150 mV, e.g., −50 mV to −300 mV, from a non-stabilized product to a stabilized product in a post-exponential growth culture phase of the production culture, wherein dissolved oxygen tension (DOT) from start of the production phase to the end of the production phase is in a range of greater than 40% to 70% air saturation;

cooling the production culture at the end of production phase to a $T_{harvest}$ temperature, which is a temperature that is below the temperature at which the cell line was or is normally cultured;

increasing the DOT to a range of greater than 10, 20, 30, 40, 50, or 60% to less than or equal to 70, 80, 90, 100, 150, 200, 250, 300, 350, 400, 450, or 500% air saturation, e.g., greater than 40% to less than or equal to 500% air saturation, by sparging air or $O_2$ gas into the production culture until removal of the production culture from the bioreactor; and maintaining a redox potential difference in the range of −10 mV to −1000 mV, −20 mV to −800 mV, −30 mV to −700 mV, −40 mV to −600 mV, −50 mV to −500 mV, −50 mV to −400 mV, −50 mV to −300 mV, −50 mV to −200 mV, or −50 mV to −150 mV, e.g., −50 mV to −300 mV, from a non-stabilized product to a stabilized product during separation of cells from production culture and collection of a supernatant, wherein separation of cells from a production culture and collection of supernatant is conducted without sparging or sufficiently little sparging that the sparging does not substantially alter the redox potential in the production culture and the supernatant.

72. The bioreactor of any of paragraphs 68-71, wherein the bioreactor is further capable of providing, e.g., adding, transition metals in or to the production culture, wherein the transition metals are selected from $Zn^{2+}$, $Mn^{4+}$, $Cu^{2+}$, $Fe^{3+}$, $Co^{2+}$, $Cr^{3+}$, and/or $Ni^{2+}$.

73. The bioreactor of any of paragraphs 68-72, wherein the bioreactor is further capable of maintaining the DOT by one or more actions selected from the group consisting of: inhibiting sparged nitrogen gas flow, inhibiting on demand alkali control if active, inhibiting on demand CO2 gas flow control if active, by inhibiting feed addition if active, activating head space pressure if not active, and activating head space flow of air/$O_2$ if not active.

74. A bioreactor capable of producing a stabilized product, e.g., a stabilized protein, expressed in a recombinant host cell, wherein the bioreactor is capable of:

(i) providing, e.g., establishing, a production culture, e.g., a post-exponential growth culture, comprising a recombinant host cell expressing the product, e.g., a protein, at a redox potential difference in the range of −10 mV to −1000 mV, −20 mV to −800 mV, −30 mV to −700 mV, −40 mV to −600 mV, −50 mV to −500 mV, −50 mV to −400 mV, −50 mV to −300 mV, −50 mV to −200 mV, or −50 mV to −150 mV, e.g., −50 mV to −300 mV, from a non-stabilized product to a stabilized product;

(ii) maintaining a redox potential difference in the range of −10 mV to −1000 mV, −20 mV to −800 mV, −30 mV to −700 mV, −40 mV to −600 mV, −50 mV to −500 mV, −50 mV to −400 mV, −50 mV to −300 mV, −50 mV to −200 mV, or −50 mV to −150 mV, e.g., −50 mV to −300 mV, from a non-stabilized product to a stabilized product in a post-growth culture phase; and (iii) maintaining a redox potential difference in the range of −10 mV to −1000 mV, −20 mV to −800 mV, −30 mV to −700 mV, −40 mV to −600 mV, −50 mV to −500 mV, −50 mV to −400 mV, −50 mV to −300 mV, −50 mV to −200 mV, or −50 mV to −150 mV, e.g., −50 mV to −300 mV, from a non-stabilized product to a stabilized product during separation of cells from production culture and collection of a supernatant, wherein separation of cells from a production culture and collection of supernatant is conducted without sparging or sufficiently little sparging that the sparging does not substantially alter the redox potential in the production culture and the supernatant, wherein the bioreactor is further capable of:

a. cooling the production culture after exponential growth phase has occurred, to a temperature of 30° C. to 33° C., which is a temperature that is below the temperature at which the cell line was or is normally cultured;

b. oxygenating the production culture, to an dissolved oxygen tension (DOT) greater than 40% to less than or equal to 70% air saturation from start of the production phase to the end of the production phase;

c. providing, e.g., adding, transition metals in or to the production culture, wherein the transition metals are selected from $Zn^{2+}$, $Mn^{4+}$, $Cu^{2+}$, $Fe^{3+}$, $Co^{2+}$, $Cr^{3+}$, and/or $Ni^{2+}$;

d. providing, e.g., adding, dehydroascorbic acid or ascorbic acid, or a dehydroascorbic acid or ascorbic acid modifying component, to the production culture;

e. providing, e.g., adding glutathione, e.g., oxidized and/or reduced glutathione, or a glutathione modifying component, to the production culture; or f. cooling the production culture for separation of cells from production culture and collection of supernatant to a temperature $T_{harvest}$ of 12° C.-18° C., which is a temperature that is below $T_{production}$.

75. The bioreactor of paragraph 74, wherein the bioreactor is capable of a, b, and f.

76. The bioreactor of paragraph 74, wherein the bioreactor is capable of a, c, and f.

77. The bioreactor of paragraph 74, wherein the bioreactor is capable of b and c.

78. The bioreactor of paragraph 74, wherein the bioreactor is capable of a, b, c, and f.

79. The bioreactor of any of paragraphs 68-77, wherein the bioreactor is operably coupled to a harvest vessel.

80. The bioreactor of paragraph 79, wherein the harvest vessel is configured to comprise or provide a head space above the reservoir culture, e.g., wherein the head space comprises a gas, e.g., air or oxygen, or a mixture of gases, e.g., air or air and oxygen.

81. The bioreactor of paragraph 80, wherein the bioreactor is configured to allow circulation of culture into the head space such that the culture travels or cascades down the wall(s) of the harvest vessel.

82. The bioreactor of paragraph 81, wherein culture from the reservoir culture is transmitted onto a surface of the bioreactor, e.g., a wall, in the head space, and flows along the surface, back to the reservoir culture.

83. The bioreactor of paragraph 82, wherein travel or cascade results in an increase in oxygenation level in the culture.

84. The bioreactor of any of paragraphs 79-83, wherein the harvest vessel is capable of maintaining the DOT of the reservoir culture at a range of greater 10, 20, 30, 40, 50, or 60% to less than or equal to 70, 80, 90, 100, 150, 200, 250, 300, 350, 400, 450, or 500% air saturation, e.g., greater than 40% to less than or equal to 500% air saturation, through surface aeration.

85. The bioreactor of any of paragraphs 79-84, wherein the harvest vessel comprises one or more of the components selected from the group consisting of: a cooling device and mechanism to further cool the reservoir culture to a temperature of 5° to 8° C.; a mixer device capable of axial mixing and an pH titrant addition port; at least one head space gas inlet port and at least one gas outlet port; at least one air flow controller and at least one $O_2$ flow controller to provide an air and $O_2$ mix; and sensors that detect DOT, redox, temperature and pH of the supernatant.

86. The bioreactor of paragraph 85, wherein the DOT, redox, temperature and pH sensor output are capable of effecting change in the sparge rates, head space, and feed or supplement addition into the bioreactor production culture prior to separation; and addition of pH titrant into the harvest vessel.

87. The bioreactor of paragraph 85, wherein the DOT, redox, temperature and pH sensor output are capable of effecting addition of pH titrant into the harvest vessel.

88. The bioreactor of any of paragraphs 79-87, wherein the bioreactor is connected to the harvest vessel using a tubing resistant to occlusion.

89. The bioreactor of paragraph 88, wherein the tubing resistant to occlusion is braided.

90. The bioreactor of any of paragraphs 79-88, wherein the flow path between the bioreactor and the harvest vessel comprises installations of DOT and redox sensors/probes.

91. The bioreactor of any of paragraphs 79-90, comprising an element, e.g., a line or nozzle, configured to deliver culture to a surface defining the head space of the harvest vessel.

92. The bioreactor of any of paragraphs 79-91, comprising a second element, e.g., a line or nozzle, configured to deliver culture to a surface defining the head space of the harvest vessel.

93. The bioreactor of any of paragraphs 68-92, wherein the bioreactor is a single use bioreactor, e.g., a bioreactor designed to allow incubation of a cell culture and thereafter being disposed, e.g., as described herein.

94. The bioreactor of any of paragraphs 68-93, wherein the bioreactor comprises a bioprocess container, a shell, at least one agitator, at least one sparger, at least one gas filter inlet port for the sparger(s) and headspace overlay, at least one fill port, at least one harvest port, at least one sample port, and at least one probe.

95. The bioreactor of any of paragraphs 68-92, wherein the bioreactor is a self-supporting biocompatible tank having a volume of at least 4000 L and at least one top impeller and at least one bottom impeller, and wherein the at least one top impeller is a hydrofoil impeller, and wherein an impeller spacing ($D_s$) between the top impeller and the bottom impeller is at least 1.229× the diameter of the bottom impeller ($D_{bottom}$) and at most $2 \times D_{bottom}$, wherein a liquid height above the top impeller ($D_o$) is at least 0.3× the diameter of the top impeller ($D_{top}$) and at most $2.5 \times D_{top}$, and wherein a bottom clearance ($D_c$) between the tank bottom and the center-line of the bottom impeller is at least 0.35× $D_{bottom}$.

96. The method of any of paragraphs 1-64 or the bioreactor of any of paragraphs 68-95, wherein the product comprises a bi-specific antibody.

97. The method of any of paragraphs 1-64 or the bioreactor of any of paragraphs 68-95, wherein the product is a protein listed in Table 1, Table 2, Table 3, or Table 4.

98. The method of any of paragraphs 1-64 or the bioreactor of any of paragraphs 68-95, wherein the product is an antibody, e.g., a monoclonal antibody, e.g., an IgG1 antibody.

99. The method of any of paragraphs 1-64 or the bioreactor of any of paragraphs 68-95, wherein the recombinant host cell is derived from a mammalian cell, e.g., a mouse, rat, Chinese hamster ovary cell (CHO) cell, Syrian hamster, monkey, ape, dog, horse, ferret, or cat cell.

100. The method of any of paragraphs 1-64 or the bioreactor of any of paragraphs 68-95, wherein the recombinant host cell is derived from a non-mammalian cell, e.g., a cell from a duck, parrot, fish, insect, plant, fungus, yeast, bacteria. e.g., *E. coli*, e.g., an Archaebacteria, or an Actinobacteria.

101. The method of any of paragraphs 1-64 or the bioreactor of any of paragraphs 68-95, wherein the recombinant host cell is a stem cell.

102. The method of any of paragraphs 1-64 or the bioreactor of any of paragraphs 68-95, wherein the recombinant host cell is a differentiated form of any of the cells described herein.

103. The method of any of paragraphs 1-64 or the bioreactor of any of paragraphs 68-95, wherein the recombinant host cell is a cell derived from any primary cell in culture.

104. The method of any of paragraphs 1-64 or the bioreactor of any of paragraphs 68-95, wherein the recombinant host cell is a CHOK1SV, GS-KO, or DUX-B11 cell.

EXAMPLES

The invention is further described in detail by reference to the following examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples specifically point out various aspects of the present invention, and are not to be construed as limiting in any way the remainder of the disclosure.

Example 1. Cooling Cells Mitigates Harvest and Storage-Associated Anoxia of Cell Samples Oxygen depletion is an identified and documented route cause of dissociation. Rates of depletion decrease with temperature. FIG. 1 shows that $O_2$ solubility increases inversely with temperature (compare 37° C., 15° C., and 5° C.). Also shown is the change of three other oxygen-associated parameters at these three temperatures. It was therefore postulated that cooling bioreactors/samples can similarly help prevent dissociation.

Figure 2:
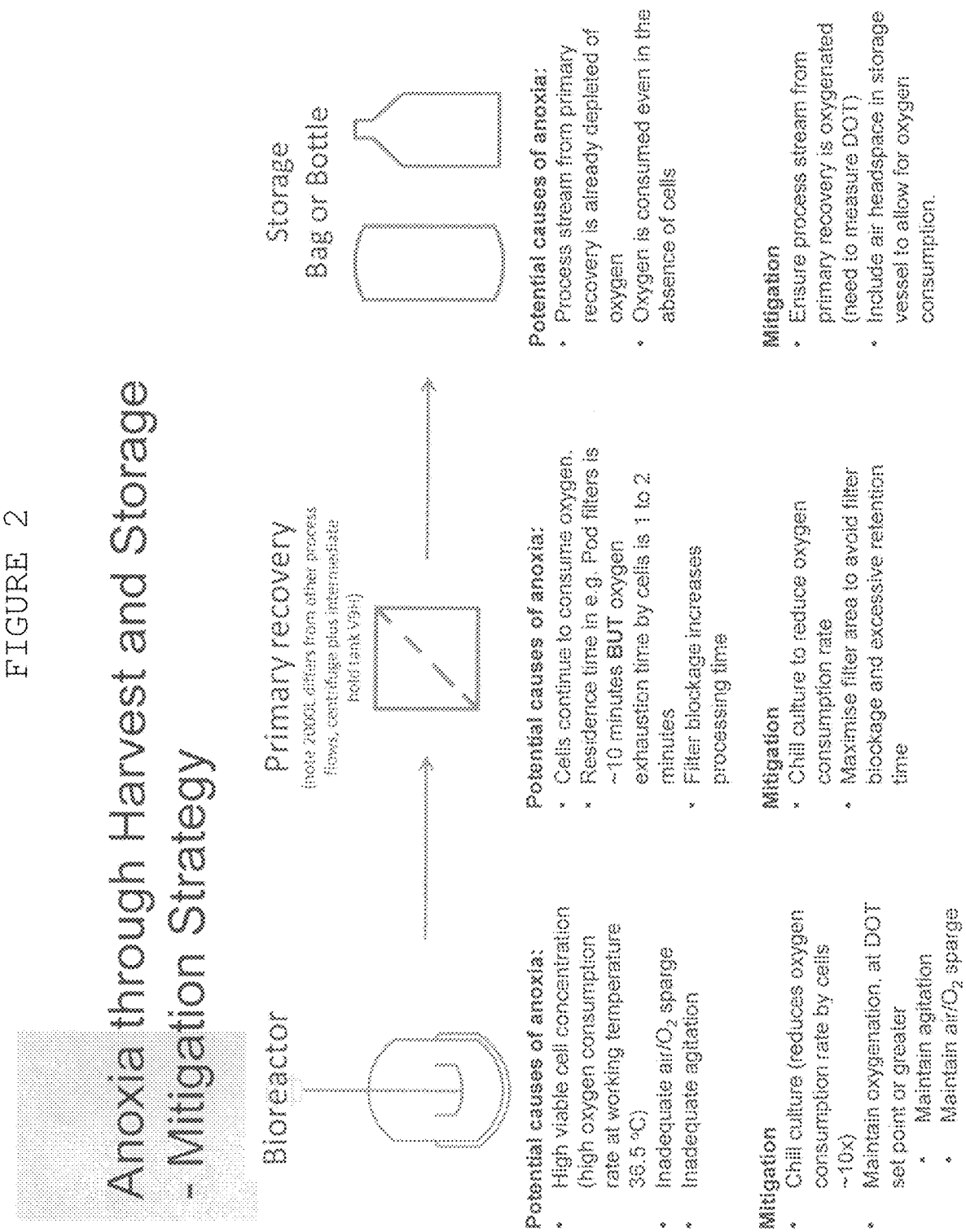
FIG. 2 is a schematic representation of mitigation schemes for minimizing polypeptide dissociation in a bioreactor, a primary recovery enclosure, and a storage device.

Mitigation strategies that include cell cooling are shown in FIG. 2 for bioreactor, primary storage chambers, and storage bags or bottles.

Figure 3:
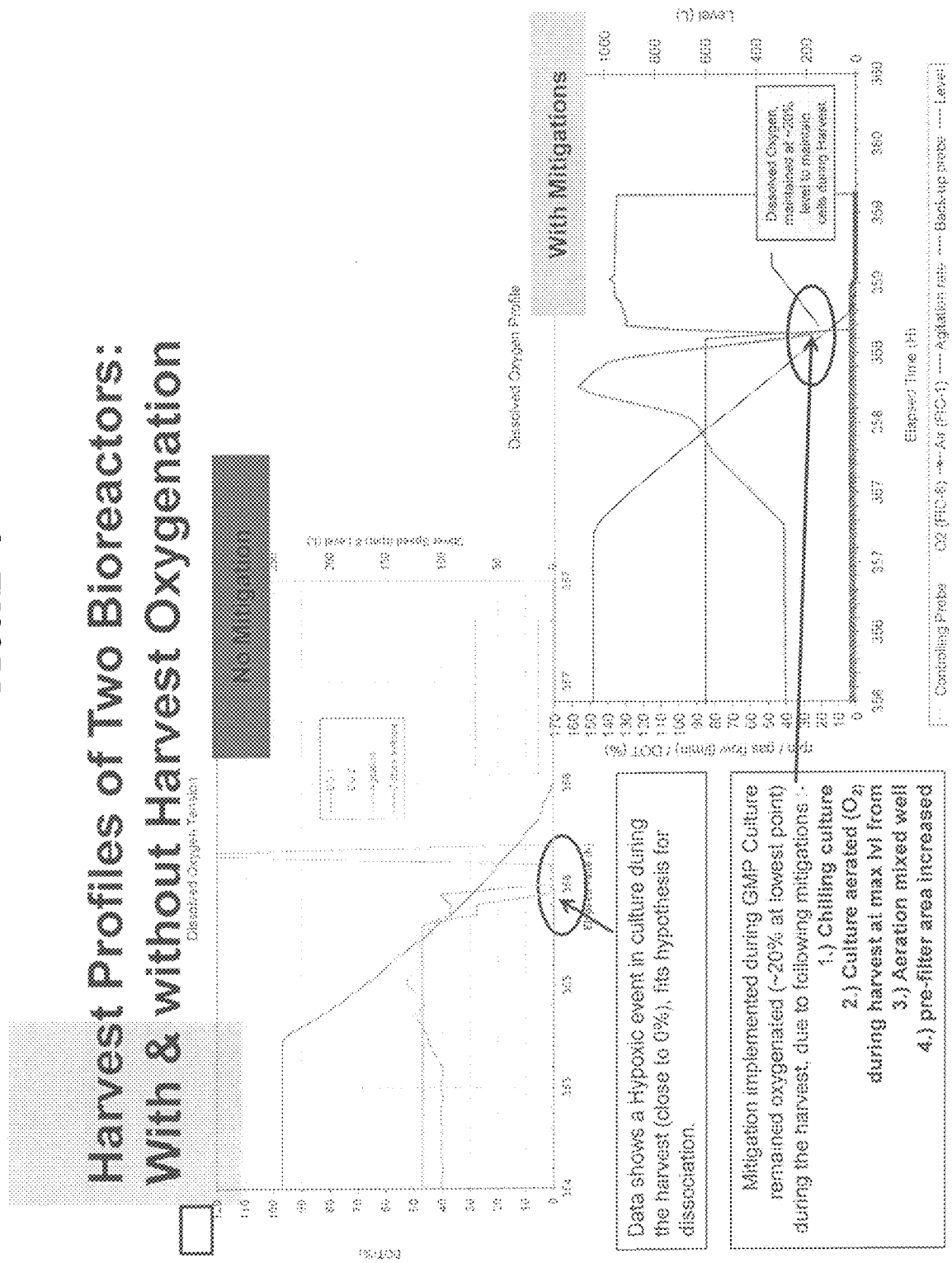
FIG. 3 shows the harvest profiles of two bioreactors with and without harvest oxygenation in the absence of mitigation and with mitigation that includes cooling the cells.

Example 2. Harvest Profiles of Two Bioreactors with and without Harvest Oxygenation Harvest profiles of two bioreactors with and without harvest oxygenation are shown in FIG. 3. The data show a hypoxic event in culture during the harvest (close to 0%), fits a hypothesis for dissociation. In contrast, a profile is shown for a culture that remained oxygenated (~20% at lowest point) during the harvest by performing mitigation strategies as shown.

Example 3. Non-Reduced SDS Polyacrylamide Gel with and without Mitigation

FIG. 4 is a representation of non-reduced SDS polyacrylamide gel samples prepared without mitigation (left panel) and with mitigation (right panel) for an IgG1 monoclonal antibody. For samples prepared without mitigation multiple bands are observed, indicative of dissociated polypeptide species. In contrast, a single high molecular weight band with no evidence of dissociation is detected for samples subjected to the mitigation strategies shown in FIG. 2. These results demonstrate that mitigation strategies that include cooling the cells inhibit protein dissociation.

No simple trend was observed between a single growth characteristic (Max viable cell concentration, harvest viable cell concentration, IVC, viability at harvest) and dissociation. The absence of a trend does not rule out the possibility of an interplay between a growth parameter(s) and another parameter(s) that together trends with dissociation.

Example 4: Redox Management

While not wishing to be bound by theory, the below table represents how air flow, oxygen flow, oxygen content of gas, and DOT relate in the methods and bioreactors of the disclosure.

| | Air flow (Lpm) | | | | | | | | | |
|---|---|---|---|---|---|---|---|---|---|---|
| | 10 | 9 | 8 | 7 | 6 | 5 | 4 | 3 | 2 | 0 |
| Oxygen Flow (Lpm) | 0 | 1 | 2 | 3 | 4 | 5 | 6 | 7 | 8 | 10 |
| Oxygen content in gas (% v/v) | 21% | 29% | 37% | 45% | 53% | 61% | 68% | 76% | 84% | 100% |
| Maximum Dissolved Oxygen Tension at equilibrium under 1 atm pressure, DOT (% of air saturation) | 100 | 138 | 175 | 213 | 250 | 288 | 326 | 363 | 401 | 476 |

Figure 5:
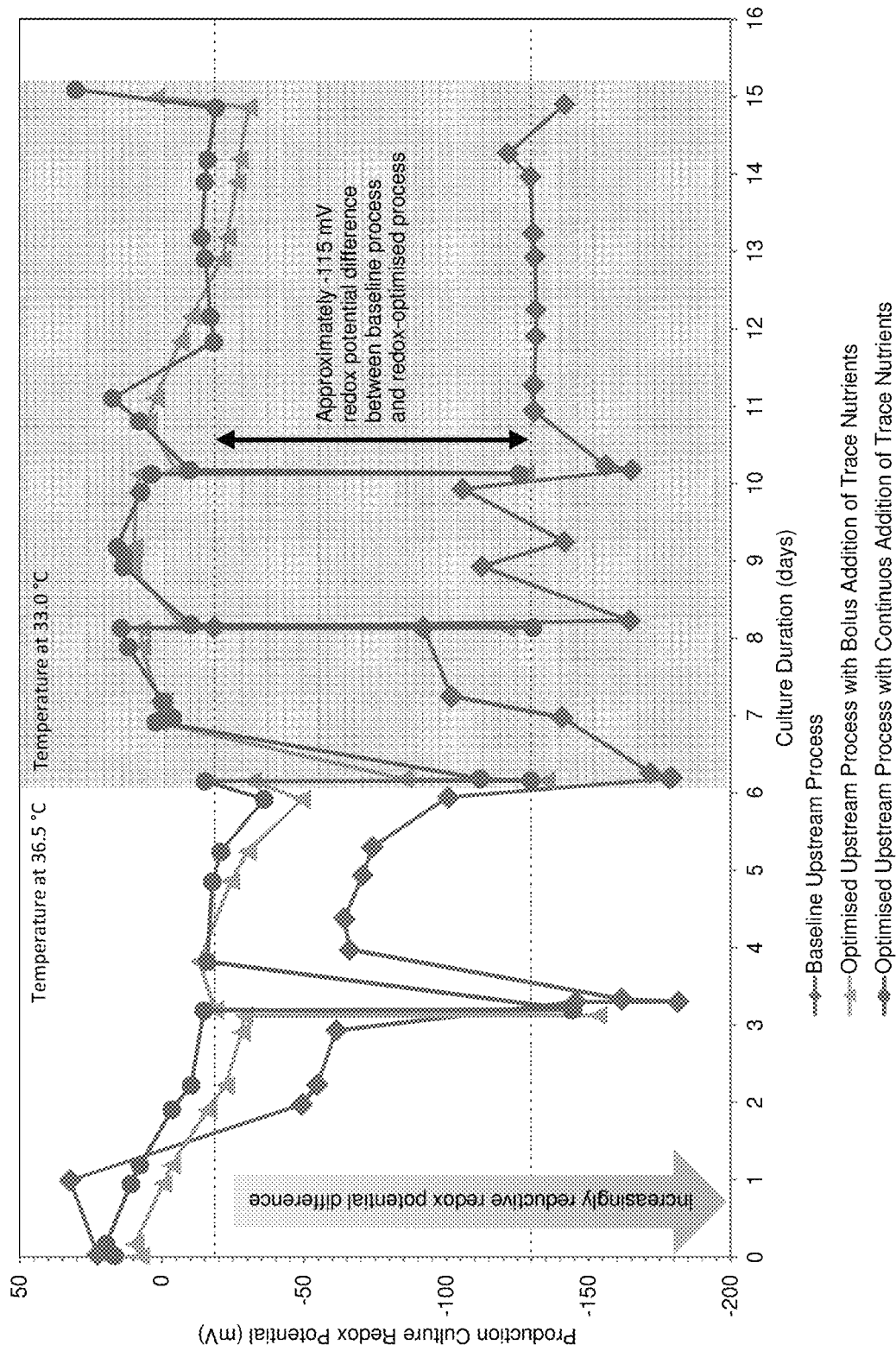
FIG. 5 shows a graph of production culture redox potential over culture duration for baseline upstream process and for optimized upstream process employing bolus addition of trace nutrients or continuous addition of trace nutrients.

FIG. 5 shows the production culture redox potential difference profiles of a baseline upstream process and an optimized upstream process employing a combination of higher process control of dissolved oxygen tension, DOT of 60% air saturation, a process temperature shift after the cell growth phase (typically day 6) from a control point of 36.5° C. to a control point of 33.0° C. Additionally, the production culture was fed with bolus feeds with elevated levels of trace nutrients such as copper, manganese and zinc salts intermittently from day 3 of culture up to day 10 of culture. In another variant of the optimized upstream process the trace nutrients were fed continuously from day 3 of culture until it was harvested on day 15 of culture. The, increased application of pro-oxidant trace nutrients from day 3 onwards confers a favorable redox potential difference of approximately −50 mV which is further improved following the temperature shift to 33.0° C. and the continued application of pro-oxidant trace nutrients to approximately −115 mV. The product produced in the baseline process displayed greater instability behavior following baseline cell clarification procedure. However the product made with redox potential difference-optimised process produced product that was more resilient to baseline cell clarification procedure where the culture may become exposed to hypoxic or anoxic environment during the harvest steps. The instability behavior for the products made using these upstream processes were:

- Increased abundance of product fragments following elution of product from a Protein A resin chromatography or after low pH treatment for virus inactivation.
- Increased product aggregation following an exposure to low pH hold typically used to inactivate viruses in manufacturing processes.

Whilst the benefits of a more oxidative redox potential difference during the production of product is beneficial it is postulated that ensuring a similar oxidative redox potential difference during the harvesting step and storage of supernatant may be equally beneficial.

It is further expected that other pro-oxidant cell culture nutrients and cellular metabolites (e.g Iron III salts, cystine/cysteine, Dehydroascorbic acid/ascorbic acid, and glutathione/glutathione-SH) might behave in a similar manner to those tested in the above example.

Example 5: Temperature Management

FIG. 6 shows the temperature profile of production culture when it is cooled to ahead of the harvest operation and the on-demand air and oxygen flow sparge rate to meet the cellular oxygen uptake by the production culture. In the event the sparge rate fall below a process specific threshold these sparge rate are fixed for the duration of harvest operation. These fixed sparge rates may be:
  Constant flow of oxygen from a minimum of 0 to a maximum flow used just prior to start of cooling of culture.
  Constant flow of air from a minimum flow equal to flow just prior to start of cooling of culture to a maximum flow to achieve an oxygen mass transfer coefficient, kLa similar to that applied just prior to cooling with both air and oxygen on demand flows.

Example 6: Oxygen Management

Figure 7A:
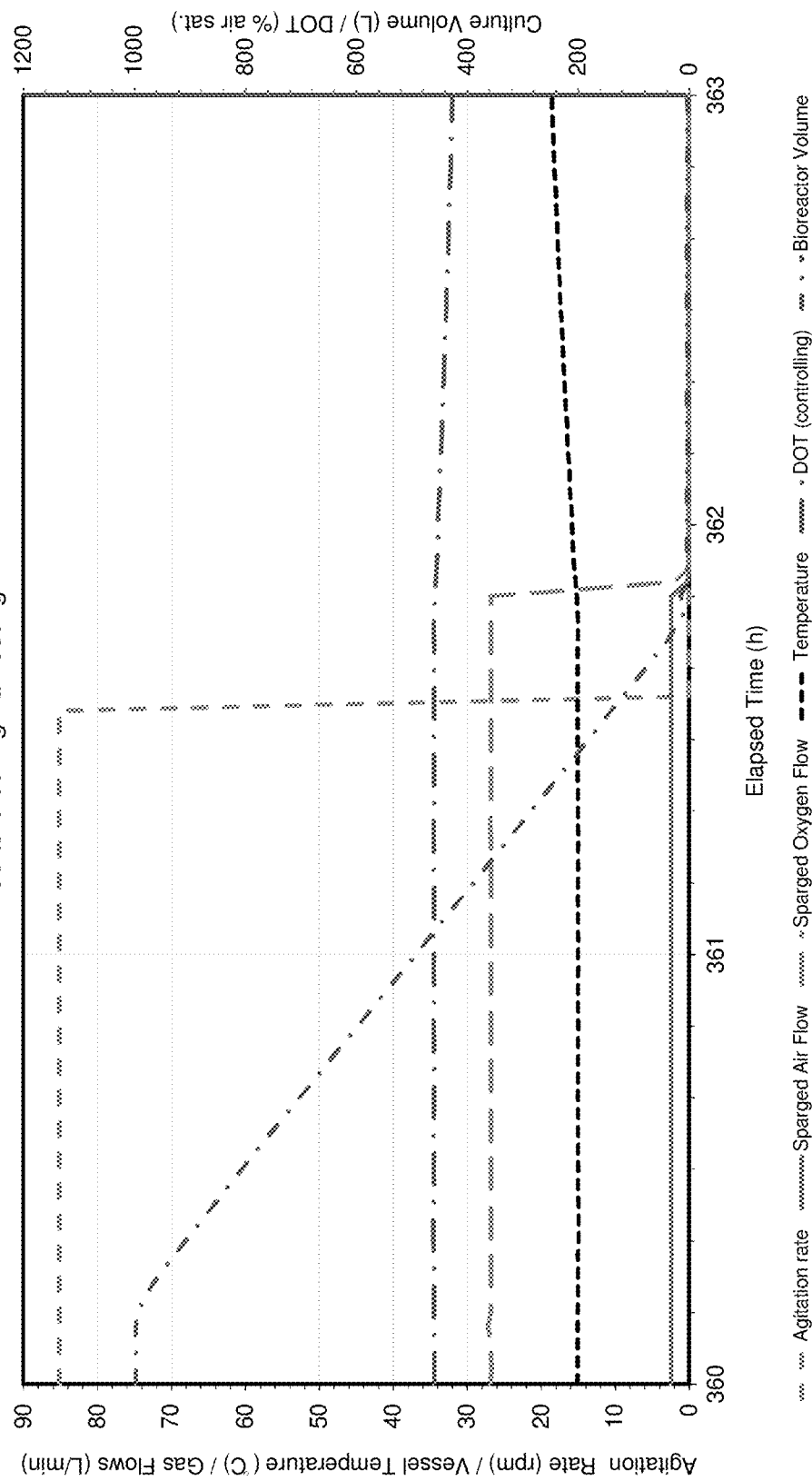
Figure 8A:
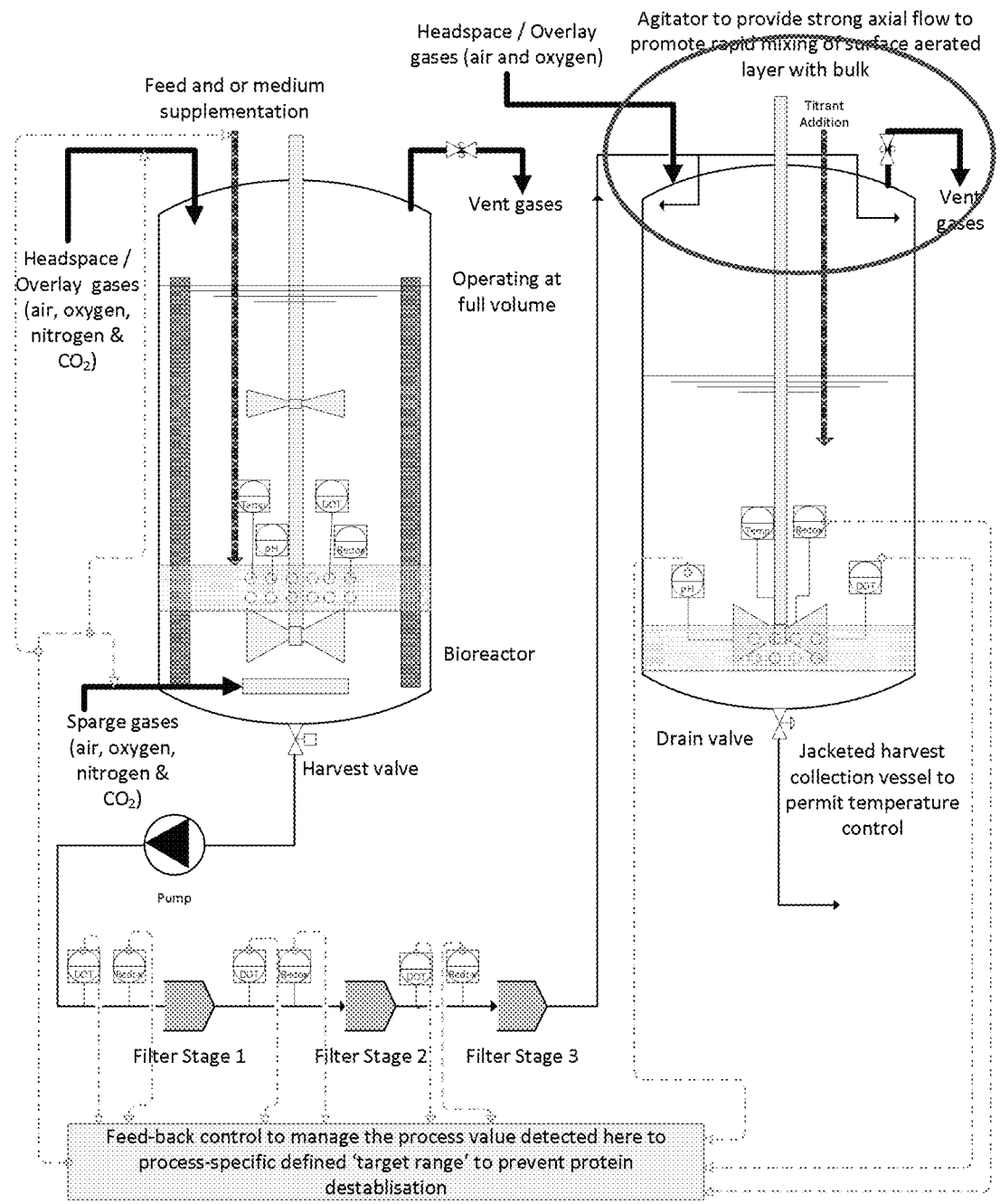
FIGS. 8A and 8B show diagrams of an exemplary bioreactor and harvest vessel with culture flow, parts, and functions labelled (FIG. 8A) and a zoomed in labelled schematic of the circled head space region of the harvest vessel of FIG. 8A (FIG. 8B).
Figure 8B:
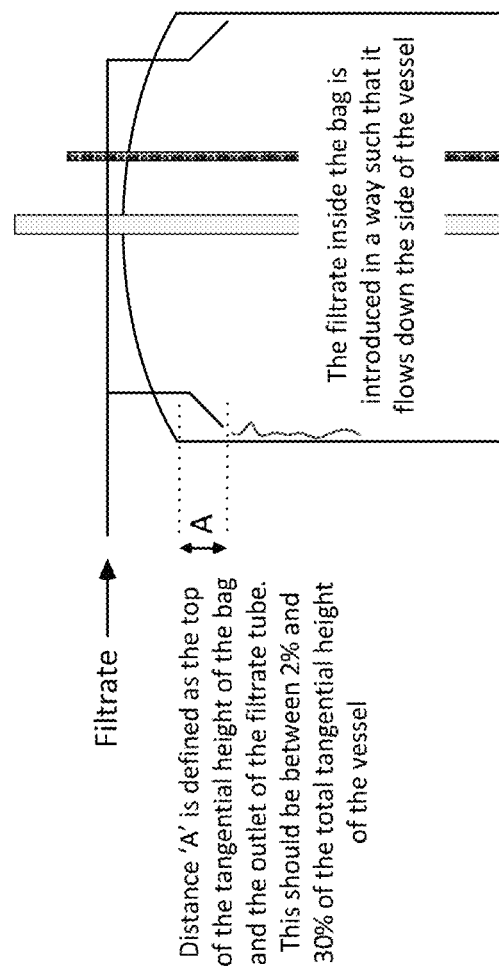
Figure 9:
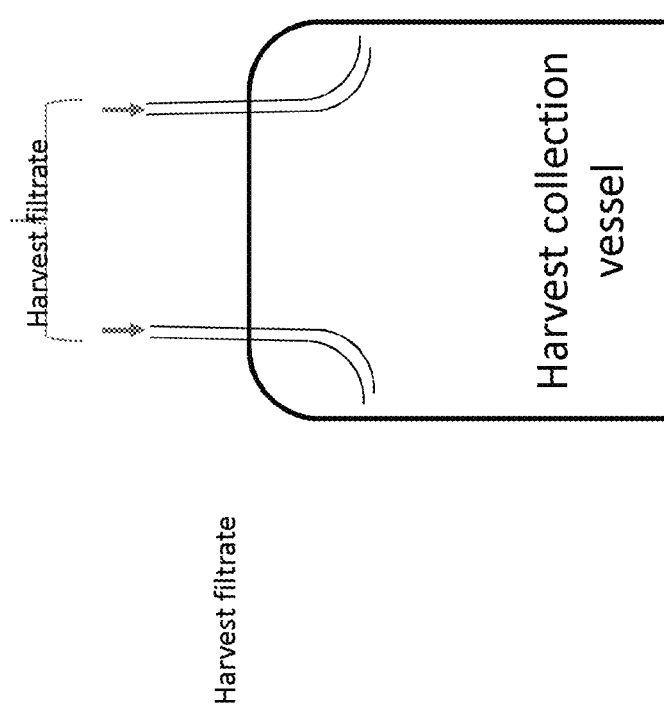
FIG. 9 shows a diagram of an exemplary harvest vessel.

FIG. 7a shows an example of key process parameter in the production culture during its harvest from a 1000 L single use bioreactor using disposable POD depth filters for clarification of the cell culture. In this instance the production culture was mixed and aerated with same agitation (mixing) and aeration rates as applied to the production culture to meet the cellular oxygen demand. The cooling of the production culture stopped the cellular demand as previously described in FIG. 1. However the continued application of similar mixing and aeration rates ensures the culture DOT continues to increase to a level limited by the proportion of oxygen enrichment of the sparged gas. Note air will saturate the dissolved oxygen in culture to a maximum of 100% air saturation. Pure oxygen will saturate the dissolved oxygen in culture to a maximum of ~500% air saturation. Therefore for any given harvest the production culture may be aerated with air or oxygen or a blend of air and oxygen. Depending on the ratio of air and oxygen used the dissolved oxygen in the culture may be variable and specific to a particular product or process, or production facility and equipment used to harvest the production culture (such as filter type, filter area, flow paths between bioreactor and filter housing and between the filter housing and the supernatant collection vessels, e.g., harvest vessels) and forward-processing operating patterns (e.g. duration the supernatant is held before purification process is initiated) used within the facility. Although in this example described headspace pressure is not used it is expected where the vessel can operate with higher than atmospheric headspace pressure, This parameter may also be used to increase the dissolved oxygen in the culture beyond 100% air saturation. However it would be expected that the culture would degas as it exits the high pressure environment within the bioreactor and the DOT of the culture decrease to equilibrate to the new pressure.

FIG. 7b shows an example of key process parameter in the production culture during its harvest from a 50 L single use bioreactor using disposable POD depth filters for clarification of the cell culture. In this instance the production culture was mixed with same agitation (mixing) as applied to the production culture. However the aeration rate was adjusted to achieve a similar oxygen mass transfer coefficient, kLa ($h^{-1}$) as needed for the production culture just before it is chilled in readiness to harvest. The composition of oxygen in the sparged gas is also increased to (in this example to 40% enrichment) to achieve a maximum culture DOT of ~200% air saturation.

An additional feature of the production culture oxygenation while harvesting may be defined by the duration under which the culture is held at high DOT before harvest proceeds. This may be defined as within <1 h of reaching the target temperature for harvest or it can be up to 24 h of reaching the target temperature for harvest.

Example 7: Bioreactor Characteristics

During the harvest of the 1000 L cGMP production culture, the sparged air and oxygen flow rate dependent on the scale of operation, in this case a 1000 L SUB. Upon review of the performance of the harvest operation, the dissolved oxygen tension (DOT) of the production culture started to decline during the late phase of the harvest when approximately ~400 L culture still remains within the SUB. An extrapolation of the DOT decline rate would suggest the culture DOT fall to hypoxic levels (DOT at 0% air saturation) within a 5 min period. The hypoxic culture subsequently enters the depth filter housing when further oxygenation is not possible. Therefore it is expected that cell culture that enter the filter housing and previously retained cells from the earlier phase of the filter clarification will become anoxic. There is evidence for this cell culture process and product that occurrence of hypoxia during harvest can lead to the product appearing as 'dissociated' when analysed, after the first chromatography step using the protein A, by non-reduced SDS electrophoresis assay see FIG. 4.

The underlying mechanism is believed to be release of cellular factors, from cell damage occurring in clarification filters during the harvest operation, which catalyse the reduction of disulphide bonds holding and folding the product subunits (IgG heavy and light chains) together. These released cellular factors are typically active (and potentially damaging to product) in their reductive state. However through continued oxygenation of the production culture while it is being harvested with adequate sparge rate in the bioreactor, sufficient oxygen needs to be made available to be carried into the depth filter and carried through into the clarified supernatant. The dissolved oxygen that is carried by the clarified supernatant prevents the activation of the cellular factors to their reduced active state and thereby avoiding catalytically driven dissociation reaction of the protein disulphide bonds. However currently there is no direct way to detect the DOT of the culture once the culture operating level falls below the DOT sensor in the bioreactor and of the culture while it is residing in the POD filter housing or when clarified supernatant is collected in the bags. Due to this limitation, a surrogate approach is applied where the sparged air and oxygen gases are applied at a continuous flow to ensure the culture whiling harvesting never displays a declining DOT trend which indicates that the cultures cellular oxygen uptake rate is greater than the bioreactor's capacity to transfer oxygen into the cell culture and if this imbalance in the oxygen transfer into the culture and dissolved oxygen loss from the culture (indicated by the declining DOT trend) continues then insufficient oxygen will be available in the clarified supernatant to prevent the activation of the cellular factors and product dissociation will ensue.

It is therefore proposed that the sparged air and oxygen flow rate that were fixed at lower flowrate are increased.

Under the revised sparge conditions the oxygen composition of the sparge gas and the volumetric flowrate can saturate the culture to a higher DOT air saturation. Additionally the total volumetric sparge gas flow rate (combined flow of air and oxygen) delivers increased oxygen mass transfer coefficient, kLa equivalent to that demanded by the production culture to maintaining culture DOT at process set point of at least 40% air saturation just before the production culture was further chilled in preparation for harvest.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention encompasses all variations, combinations, and permutations in which one or more limitations, elements, clauses, and descriptive terms from one or more of the listed claims are introduced into another claim. Where elements are presented as lists, e.g., in Markush group format or as an alternative, each subgroup of the elements is also disclosed, and any element(s) can be removed from the group.

It should it be understood that, in general, where the invention, or aspects of the invention, is/are referred to as comprising particular elements and/or features, certain embodiments of the invention or aspects of the invention consist, or consist essentially of, such elements and/or features. It is also noted that the terms "comprising" and "containing" are intended to be open and permit the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

What is claimed is:

1. A method of producing a stabilized product expressed in a recombinant host cell, comprising:
    providing a redox potential difference in the range of −50m V to −300m V from a non-stabilized product to the stabilized product in a post-exponential growth culture phase of a production culture,
    cooling the production culture at the end of a production phase to a $T_{harvest}$ temperature which is a temperature that is below the temperature at which the recombinant host cell was or is normally cultured; and
    maintaining the redox potential difference during separation of the recombinant host cell from the production culture and collection of a supernatant,
    thereby producing the stabilized product.

2. The method of claim 1, further comprising monitoring the redox potential of cells within the culture and while isolating the product for the purpose of maintaining the redox potential.

3. The method of claim 2, wherein monitoring the redox potential comprises using in-line monitoring probes.

4. The method of claim 1 further comprising recovering and purifying the stabilized product.

5. The method of claim 4, wherein the purification step uses chromatography.

6. A method of producing a stabilized product expressed in a recombinant host cell, comprising:
    providing a redox potential difference in the range of −50 mV to −300 mV from a non-stabilized product to the stabilized product in a post-exponential growth culture phase of a production culture, wherein dissolved oxygen tension (DOT) from a start of a production phase to an end of the production phase is in a range of greater than 40% air saturation;
    cooling the production culture at the end of the production phase to a $T_{harvest}$ temperature, which is a temperature that is below the temperature at which the cell was or is normally cultured;
    increasing the DOT to a range of greater than 40% to less than 500% air saturation by sparging air or $O_2$ gas into the production culture until separation of cells from the production culture and collection of supernatant; and
    maintaining the redox potential difference during separation of the recombinant host cell cells from the production culture and collection of a supernatant,
    thereby producing the stabilized product.

7. The method of claim 6, wherein $T_{harvest}$ is sufficiently low to inhibit dissociation of the disulfide bond.

8. The method of claim 6, comprising separating the recombinant host cell from the production culture at $T_{harvest}$.

9. The method of claim 6, wherein the recombinant host cell line is cultured at a first temperature, $T_{culture}$, and is harvested at $T_{harvest}$.

10. The method of claim 9, wherein $T_{harvest}$ is at least 19° to 25° C. below $T_{culture}$.

11. The method of claim 9, wherein $T_{culture}$ is 30° C. to 38° C.

12. The method of claim 6, wherein $T_{harvest}$ is 12° C. to 18° C.

13. The method of claim 6, wherein the stabilized product is applied to a filter at $T_{harvest}$.

14. The method of claim 6, wherein the recombinant host cell is cultured in a bioreactor.

15. The method of claim 14, wherein the contents of the bioreactor are cooled to $T_{harvest}$ after production phase.

16. The method of claim 14, wherein the cell culture is cooled by contact with a member comprising a fluid at a temperature suitable for bringing the cell culture to $T_{harvest}$.

17. The method of claim 14, wherein the bioreactor has a volume of 50 liters to 800 liters.

18. The method of claim 14, wherein the bioreactor is a single use bioreactor.

19. The method of claim 14, wherein the bioreactor comprises a bioprocess container, a shell, at least one agitator, at least one sparger, at least one gas filter inlet port for the sparger(s) and headspace overlay, at least one fill port, at least one harvest port, at least one sample port, and at least one probe.

20. The method of claim 14, wherein the bioreactor comprises processes and probes for monitoring and maintaining one or more of pH, dissolved oxygen tension (DOT), or temperature.

21. The method of claim 14, wherein the bioreactor is a self-supporting biocompatible tank having a volume of at least 4000 L and at least one top impeller and at least one bottom impeller, and wherein the at least one top impeller is a hydrofoil impeller, and wherein an impeller spacing ($D_s$) between the top impeller and the bottom impeller is at least $1.229 \times$ the diameter of the bottom impeller ($D_{bottom}$) and at most $2 \times D_{bottom}$, wherein a liquid height above the top impeller ($D_o$) is at least $0.3 \times$ the diameter of the top impeller ($D_{top}$) and at most $2.5 \times D_{top}$, and wherein a bottom clearance ($D_o$) between the tank bottom and the center-line of the bottom impeller is at least $0.35 \times D_{bottom}$.

22. The method of claim 14, wherein the bioreactor is operably coupled to a harvest vessel.

23. The method of claim 22, wherein the harvest vessel is configured to comprise or provide a head space above the reservoir culture, wherein the head space comprises a gas or a mixture of gases.

24. The method of claim 23, wherein the harvest vessel is configured to allow collection of supernatant though a J-tube port into the head space such that the supernatant travels or cascades down the wall(s) of the harvest vessel.

25. The method of claim 24, wherein the supernatant is transmitted onto a surface of the harvest vessel in the head space, and flows along the surface, back to the reservoir culture.

26. The method of claim 25, wherein supernatant travel or cascade in the harvest vessel results in an increase in oxygenation level of the supernatant.

27. The method of claim 22, wherein the DOT of the supernatant is maintained at a range of greater than 40% to less than 500% air saturation in the harvest vessel through surface aeration.

28. The method of claim 22, wherein the harvest vessel comprises a cooling device and mechanism to further cool the reservoir culture to a temperature of 5° to 8° C.

29. The method of claim 22, wherein the harvest vessel comprises a mixer device capable of axial mixing and an pH titrant addition port.

30. The method of claim 22, wherein the harvest vessel comprises at least one head space gas inlet port and at least one gas outlet port.

31. The method of claim 22, wherein the harvest vessel further comprises at least one air flow controller and at least one $O_2$ flow controller to provide an air and $O_2$ mix.

32. The method of claim 22, wherein the harvest vessel comprises sensors that detect DOT, redox, temperature and pH of the supernatant.

33. The method of claim 32, wherein the DOT, redox, temperature and pH sensor output are used to effect change in the sparge rates, head space, and feed or supplement addition into the bioreactor production culture prior to separation; and addition of pH titrant into the harvest vessel.

34. The method of claim 32, wherein the DOT, redox, temperature and pH sensor output are used to effect change addition of pH titrant into the harvest vessel.

35. The method of claim 22, wherein the bioreactor is connected to the harvest vessel using a tubing resistant to occlusion.

36. The method of claim 35, wherein the tubing resistant to occlusion is braided.

37. The method of claim 22, wherein the flow path between the bioreactor and the harvest vessel comprises installations of DOT and redox sensors/probes.

38. The method of claim 37, wherein the DOT and redox sensors/probes output is used to effect change in the sparge rates, head space, and feed or supplement addition into the bioreactor production culture prior to harvest.

39. The method of claim 22, wherein the bioreactor comprises an element configured to deliver culture to a surface defining the headspace of the bioreactor.

40. The method of claim 22, wherein the bioreactor comprises a second element configured to deliver culture to a surface defining the headspace of the bioreactor.

41. The method of claim 40, wherein monitoring the redox potential comprises evaluating redox status of the cellular factors that impact product stability wherein the cellular factors may compromise an enzyme or metabolic cofactor of the glutathione/reduced glutathione pathway, thioredoxin/reduced thioredoxin pathway, or pentose phosphate pathways selected from glutathione reductase, thioredoxin, glucose-6-phosphate, NADPH, NADP+, 6-phosphonoglucolactone, 6-phosphogluconate, or ribulose-5-phosphate.

42. The method of claim 6 further comprising recovering and purifying the stabilized product.

43. The method of claim 42, wherein the purification step uses chromatography.

44. A method of producing a stabilized product, expressed in a recombinant host cell, comprising:
(i) providing a post-exponential growth culture, comprising a recombinant host cell expressing the product at a redox potential difference in the range of −50 mV to −300 mV from a non-stabilized product to a stabilized product;
(ii) maintaining the redox potential difference in a post-growth culture phase; and
(iii) maintaining the redox potential during separation of cells from production culture and collection of a supernatant,
wherein the method comprises:
a. cooling the production culture after exponential growth phase has occurred, to a temperature $T_{production}$ of 30° C. to 33° C., which is a temperature that is below the temperature at which the recombinant host cell was or is normally cultured; and one or more of the following steps:
b. oxygenating the production culture, to a dissolved oxygen tension (DOT) greater than 40% to less than or equal to 70% air saturation from start of the production phase to the end of the production phase;
c. providing transition metals in or to the production culture, wherein the transition metals comprise $Zn^{2+}$, $Mn^{4+}$, $Cu^{2+}$, $Fe^{3+}$, $Co^{2+}$, $Cr^{3+}$, and/or $Ni^{2+}$;
d. providing dehydroascorbic acid or ascorbic acid, or a dehydroascorbic acid or ascorbic acid modifying component, to the production culture;
e. providing glutathione, e.g., oxidized and/or reduced glutathione, or a glutathione modifying component, to the production culture; or
f. cooling the production culture for separation of cells from production culture and collection of supernatant to a temperature $T_{harvest}$ of 12° C.–18° C., which is a temperature that is below $T_{production}$,
thereby producing a stabilized product.

45. The method of claim 44, wherein the method comprises steps a, b, and f.

46. The method of claim 44, wherein the method comprises steps a, c, and f.

47. The method of claim 44, wherein the method comprises steps a, b and c.

48. The method of claim 44, wherein the method comprises steps a, b, c, and f.

* * * * *

UNITED STATES PATENT AND TRADEMARK OFFICE
CERTIFICATE OF CORRECTION

| | | |
|---|---|---|
| PATENT NO. | : 10,975,409 B2 | Page 1 of 1 |
| APPLICATION NO. | : 15/619876 | |
| DATED | : April 13, 2021 | |
| INVENTOR(S) | : Khan et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 701 days.

Signed and Sealed this
Tenth Day of January, 2023

Katherine Kelly Vidal
*Director of the United States Patent and Trademark Office*